United States Patent
Ying et al.

(10) Patent No.: US 8,188,075 B2
(45) Date of Patent: May 29, 2012

(54) TRIAZOLE COMPOUNDS THAT MODULATE HSP90 ACTIVITY

(75) Inventors: Weiwen Ying, Groton, MA (US); Kevin Foley, Waltham, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 408 days.

(21) Appl. No.: 12/310,150

(22) PCT Filed: Aug. 14, 2007

(86) PCT No.: PCT/US2007/017996
§ 371 (c)(1),
(2), (4) Date: Dec. 23, 2009

(87) PCT Pub. No.: WO2008/021364
PCT Pub. Date: Feb. 21, 2008

(65) Prior Publication Data
US 2010/0093717 A1 Apr. 15, 2010

Related U.S. Application Data

(60) Provisional application No. 60/838,306, filed on Aug. 17, 2006.

(51) Int. Cl.
*A61K 31/4196* (2006.01)
*A61K 31/5377* (2006.01)
*A61K 31/519* (2006.01)
*A61K 31/538* (2006.01)
*A61K 31/428* (2006.01)

(52) U.S. Cl. ............... 514/230.5; 514/236.2; 514/263.2; 514/367; 514/384

(58) Field of Classification Search ............... 514/236.2, 514/253.2, 367, 384
See application file for complete search history.

(56) References Cited

FOREIGN PATENT DOCUMENTS

| | | |
|---|---|---|
| DE | 10 2005 007304 | 8/2006 |
| EP | 1857446 | 11/2007 |
| WO | WO 2004/089367 | 10/2004 |
| WO | WO 2005/000300 | 1/2005 |
| WO | WO 2006/055760 | 5/2006 |
| WO | WO 2006/091246 | 8/2006 |
| WO | WO 2006/095783 | 9/2006 |
| WO | WO 2007/094819 | 8/2007 |
| WO | WO 2007/134678 | 11/2007 |
| WO | WO 2007/139951 | 12/2007 |
| WO | WO 2007/139952 | 12/2007 |
| WO | WO 2007/139955 | 12/2007 |
| WO | WO 2007/139960 | 12/2007 |
| WO | WO 2007/139967 | 12/2007 |
| WO | WO 2007/140002 | 12/2007 |

OTHER PUBLICATIONS

International Search Report and Written Opinion—(PCT/US2007/017996) Date of Mailing Feb. 5, 2008.

*Primary Examiner* — Raymond Henley, III
(74) *Attorney, Agent, or Firm* — McCarter & English LLP

(57) ABSTRACT

The present invention relates to substituted triazole compounds and compositions comprising substituted triazole compounds. The invention further relates to methods of treating or inhibiting angiogenesis in a subject in need thereof and methods for blocking, occluding, or otherwise disrupting blood flow in neo vasculature, in a subject in need thereof comprising administering to the subject a substituted triazole compound of the invention, or a composition comprising such a compound.

46 Claims, 5 Drawing Sheets

TRIAZOLE COMPOUNDS THAT MODULATE HSP90 ACTIVITY

RELATED APPLICATIONS

This application is the U.S. National Stage of International Application No. PCT/US2007/017996, filed Aug. 14, 2007, published in English, and claims the benefit of U.S. Provisional Application No. 60/838,306, filed Aug. 17, 2006, the entire teachings of which are incorporated herein by reference.

BACKGROUND OF THE INVENTION

Heat shock proteins (HSPs) are a class of chaperone proteins that are up-regulated in response to elevated temperature and other environmental stresses, such as ultraviolet light, nutrient deprivation, and oxygen deprivation. HSPs act as chaperones to other cellular proteins (called client proteins) and facilitate their proper folding and repair, and aid in the refolding of misfolded client proteins. There are several known families of HSPs, each having its own set of client proteins. The Hsp90 family is one of the most abundant HSP families, accounting for about 1-2% of proteins in a cell that is not under stress and increasing to about 4-6% in a cell under stress. Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer.

Hsp90 has been shown by mutational analysis to be necessary for the survival of normal eukaryotic cells. However, Hsp90 is over expressed in many tumor types indicating that it may play a significant role in the survival of cancer cells and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes simultaneous inhibition of a number of oncoproteins, as well as hormone receptors and transcription factors making it an attractive target for an anti-cancer agent. In fact, benzoquinone ansamycins, a family of natural products that inhibit Hsp90, has shown evidence of therapeutic activity in clinical trials.

Angiogenesis is a fundamental process of generating new blood vessels (neovasculature) in tissues or organs. Although angiogenesis is necessary for organ growth and repair, uncontrolled angiogenesis is involved with or associated with many diseases or disorders. (e.g. cancers, macular degeneration, autoimmune diseases, etc.) As such, angiogenesis has become a target for the treatment of these diseases. Ferrara, N., et al., *Nature* 438:15 967-974 (2005).

Angiogenesis is controlled by a number of growth factors and cell-adhesion molecules in endothelial and mural cells. Ferrara, N., et al., *Nature* 438:15 967-974 (2005). Among these, VEGF-A (vascular endothelial growth factor-A) and its receptors have been widely studied and characterized. Ferrara, N., et al., *Nature* 438:15 967-974 (2005). It is believed that Hsp90 chaperones a number of proteins in the angiogenic cascade. Sanderson, S., et al., *Mol Cancer Ther* 5(3) 522-32 (2006). Data has shown that VEGFR-2 (VEGF receptor) and other VEGFRs are Hsp90 client proteins. Sanderson, S., et al., *Mol Cancer Ther* 5(3) 522-32 (2006).

A number of VEGF inhibitors are approved or currently in clinical trials. Carmeliet, P., *Nature* 438:15 932-936 (2005). Clinical trials have shown that the current angiogenesis therapies have a number of limitations, including being ineffective as a monotherapy and anti-angiogenic resistance. Carmeliet, *Nature* 438:15 932-936 (2005). Therefore, a need exists for new therapeutics that reduce or overcome the limitations of currently used anti-angiogenic agents.

SUMMARY OF THE INVENTION

The present invention provides methods of treating or inhibiting (e.g., reducing) angiogenesis. The present invention also provides methods for reducing, blocking, occluding, or otherwise disrupting blood flow in neovasculature. The present invention also provides new uses for previously disclosed compounds.

Triazole compounds that modulate Hsp90 activity have previously been described in copending U.S. Publication No. 20060167070, filed Nov. 17, 2005, which is incorporated by reference herein in its entirety.

The present invention provides compounds having the formula (I):

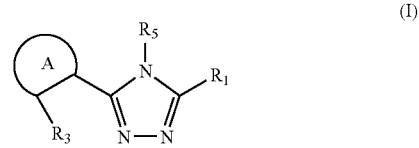

and tautomers, pharmaceutically acceptable salts, solvates, clathrates, and prodrugs thereof. In formula (I), ring A is an aryl or a heteroaryl, wherein the aryl or the heteroaryl are optionally further substituted with one or more substituents in addition to $R_3$;

$R_1$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

$R_3$ is —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)O$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$,

—NR₇C(S)R₇, —OC(S)OR₇, —SC(S)OR₇, —NR₇C(S)OR₇, —OC(S)NR₁₀R₁₁, —SC(S)NR₁₀R₁₁, —NR₇C(S)NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —OP(O)(OR₇)₂, or —SP(O)(OR₇)₂;

R₅ is an optionally substituted heteroaryl or an optionally substituted 8 to 14 membered aryl;

R₇ and R₈, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R₁₀ and R₁₁, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R₁₀ and R₁₁, taken together with the nitrogen to which they are attached, form an optionally substituted heterocyclyl or an optionally substituted heteroaryl;

R₂₆ is a lower alkyl;

p, for each occurrence, is, independently, 1 or 2; and m, for each occurrence, is independently, 1, 2, 3, or 4.

In one embodiment, ring A of the the compounds of formula (I) is not a substituted [1,2,3]triazole, and/or compounds represented by formula (I) do not include 3-(2,4-dihydroxyphenyl)-4-(7-naphthalen-1-yl)-5-mercapto-triazole.

The present invention also provides compounds having the formula (II):

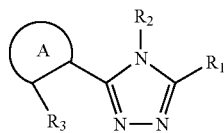

(II)

and tautomers, pharmaceutically acceptable salts, solvates, clathrates, and prodrugs thereof. In formula (II), ring A, R₁, and R₃ are defined as for formula (I); and R₂ is a substituted phenyl, wherein the phenyl group is substituted with:

i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxylalkyl, alkoxyalkyl, guanadino, —NR₁₀R₁₁, —O—R₂₀, —C(O)R₇, —C(O)OR₂₀, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, or ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, —F, —Br, —I, cyano, nitro, guanadino, a haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁; and R₂₀, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

In one embodiment, compounds represented by formula (II) do not include 3-(2,4-dihydroxy-phenyl)-4-(7-naphthalen-1-yl)-5-mercapto-triazole, 3-(2,4-dihydroxyphenyl)-4-(2,5-dimethoxyphenyl)-5-mercapto-triazole, 3-(1-phenyl-5-amino-pyrazol-4-yl)-4-(2,4-dichlorophenyl)-5-mercapto-triazole, or 3-(2-hydroxy-phenyl)-4-(2,4-dimethylphenyl)-5-mercapto-triazole.

The present invention also provides compounds having the formula (III):

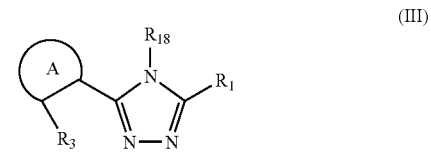

(III)

and tautomers, pharmaceutically acceptable salts, solvates, clathrates, and prodrugs thereof. In formula (III), ring A, R₁, and R₃ are defined as for formula (I); and R₁₈ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, or —SP(O)(OR₇)₂;

In one embodiment, compounds represented by formula (III) do not include compounds in which R₁₈ is not cyclohexyl.

The invention also provides compounds represented by formula (IV) or formula (V):

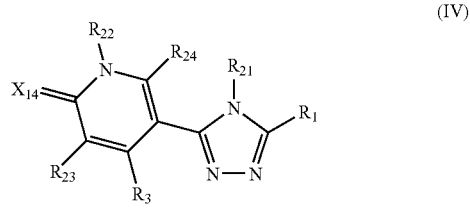

(IV)

-continued

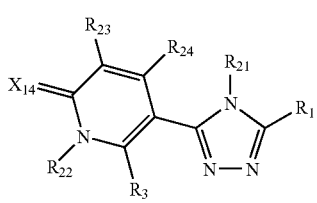

(V)

and tautomers, pharmaceutically acceptable salts, solvates, clathrates, and prodrugs thereof. In formulas (IV) and (V), $R_1$ and $R_3$ are defined as for formula (I); and $X_{14}$ is O, S, or $NR_7$;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{22}$, for each occurrence, is independently —H or is selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —C(O)R$_7$, —C(O)OR$_7$, —OC(O)R$_7$, —C(O)NR$_{10}$R$_{11}$, —NR$_8$C(O)R$_7$, —S(O)$_p$R$_7$, —S(O)$_p$OR$_7$, or —S(O)$_p$NR$_{10}$R$_{11}$; and $R_{23}$ and $R_{24}$, for each occurrence, are independently —H or are selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$.

The present invention also provides compounds represented by formula (VI):

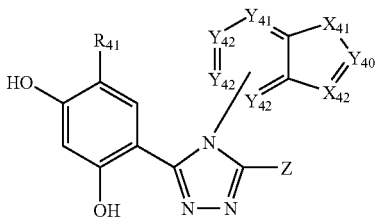

(VI)

and tautomers, pharmaceutically acceptable salts, solvates, clathrates, and prodrugs thereof, wherein:

$X_{41}$ is O, S, or $NR_{42}$;
$X_{42}$ is $CR_{44}$ or N;
$Y_{40}$ is N or $CR_{43}$;
$Y_{41}$ is N or $CR_{45}$;
$Y_{42}$, for each occurrence, is independently N, C or $CR_{46}$;
Z is OH, SH, or $NHR_7$;

$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —C(O)R$_7$, —(CH$_2$)$_m$C(O)OR$_7$, —C(O)OR$_7$, —OC(O)R$_7$, —C(O)NR$_{10}$R$_{11}$, —S(O)$_p$R$_7$, —S(O)$_p$OR$_7$, or —S(O)$_p$NR$_{10}$R$_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, —S(O)$_p$NR$_{10}$R$_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, or —NR$_7$C(NR$_8$)N$_{10}$R$_{11}$;

$R_{46}$, for each occurrence, is independently selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_7$, $R_8$, $R_{10}$, $R_{11}$, $R_{26}$, p, and m are defined as above.

The present invention also provides compounds represented by formula (VII):

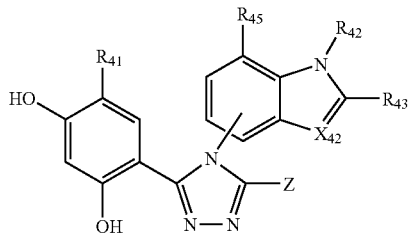

(VII)

and tautomers, pharmaceutically acceptable salts, solvates, clathrates, and prodrugs, wherein:

$Z_1$ is —OH or —SH; and $X_{42}$, $R_{41}$, $R_{42}$, $R_{43}$, and $R_{45}$ are defined as above.

The present invention also provides compounds having the formula (VIII):

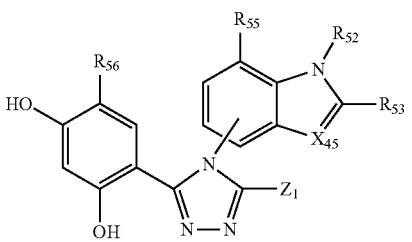

(VIII)

and tautomers, pharmaceutically acceptable salts, solvtes, clathrates, and prodrugs thereof, wherein:

$X_{45}$ is $CR_{54}$ or N;

$Z_1$ is —OH or —SH;

$R_{52}$ is selected from the group consisting of —H, methyl, ethyl, n-propyl, isopropyl, n-butyl, n-pentyl, n-hexyl, —$(CH_2)_2OCH_3$, —$CH_2C(O)OH$, and —$C(O)N(CH_3)_2$;

$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring;

$R_{55}$ is selected from the group consisting of —H, —OH, —$OCH_3$, and —$OCH_2CH_3$; and $R_{56}$ is selected from the group consisting of —H, methyl, ethyl, isopropyl, and cyclopropyl.

The present invention also provides compounds having the formula (IX):

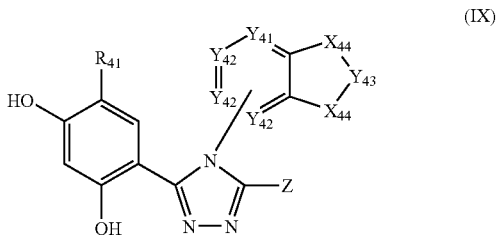

(IX)

and tautomers, pharmaceutically acceptable salts, solvates, clathrates, and prodrugs thereof, wherein, $X_{44}$, for each occurrence, is independently, O, S, $NR_{42}$ or $C(R_{46})_2$;

$Y_{43}$ is $NR_{42}$, $C(R_{46})_2$, $C(R_{46})_2$—$C(R_{46})_2$, C(O), C(S), $C(R_{46})_2C(O)$, or $C(R_{46})_2C(S)$;

$Y_{41}$, $Y_{42}$, Z, $R_{41}$, $R_{42}$, and $R_{46}$ are defined as above.

In one embodiment, in formula (IX), $R_{41}$ is selected from the group consisting of —H, lower alkyl, lower alkoxy, lower cycloalkyl, and lower cycloalkoxy.

In another embodiment, in formula (IX), $R_{41}$ is selected from the group consisting of —H, methyl, ethyl, propyl, isopropyl, cyclopropyl, methoxy, ethoxy, propoxy, and cyclopropoxy.

In another embodiment, in formula (IX), $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —$(CH_2)_mC(O)OH$, —$CH_2OCH_3$, —$CH_2CH_2OCH_3$, and —$C(O)N(CH_3)_2$.

In another embodiment, in formula (IX), $Y_{41}$ is $CR_{45}$. Preferably, $R_{45}$ is H, a lower alkoxy, or —OH.

In another embodiment, in formula (IX), $Y_{42}$ is CH.

In another embodiment, in formula (IX), $Y_{43}$ is $CH_2$.

In another embodiment, in formula (IX), $Y_{43}$ is $NR_{42}$, wherein $R_{42}$ is H or a lower alkyl.

In another embodiment, in formula (IX), one of $X_{44}$ is $NR_{42}$ and the other is $CH_2$ or $C(R_6)_2$. Preferably, one of $X_{44}$ is $NR_{42}$ and the other is $CH_2$.

In another embodiment, in formula (VI), Z is —OH.

In another embodiment, Z is —SH.

In another embodiment, the compound is selected from the group consisting of:

3-(2,4-dihydroxy-5-isopropyl-phenyl)-4-(1,3-benzodiaxol-5-yl)-5-mercapto-[1,2,4]triazole;

3-(2,4-dihydroxy-5-isopropyl-phenyl)-4-(indan-5-yl)-5-mercapto-[1,2,4]triazole;

4-Ethyl-6-[5-mercapto-4-(1-methyl-2,3-dihydro-1H-indol-5-yl)-4H-[1,2,4]triazol-3-yl]-benzene-1,3-diol;

5-(3-(5-ethyl-2,4-dihydroxyphenyl)-5-mercapto-4H-1,2,4-triazol-4-yl)indolin-2-one;

5-(3-(5-ethyl-2,4-dihydroxyphenyl)-5-mercapto-4H-1,2,4-triazol-4-yl)-1H-benzo[d]imidazol-2(3H)-one;

5-(3-(5-ethyl-2,4-dihydroxyphenyl)-5-mercapto-4H-1,2,4-triazol-4-yl)-1-methylindolin-2-one;

4-isopropyl-6-(5-mercapto-4-(4-propyl-3,4-dihydro-2H-benzo[b][1,4]oxazin-6-yl)-4H-1,2,4-triazol-3-yl)benzene-1,3-diol;

6-(3-(5-ethyl-2,4-dihydroxyphenyl)-5-mercapto-4H-1,2,4-triazol-4-yl)-2H-benzo[b][1,4]oxazin-3(4H)-one;

6-(3-(5-ethyl-2,4-dihydroxyphenyl)-5-mercapto-4H-1,2,4-triazol-4-yl)-3-methylbenzo[d]thiazol-2(3H)-one;

6-(3-(5-ethyl-2,4-dihydroxyphenyl)-5-mercapto-4H-1,2, 4-triazol-4-yl)benzo[d]thiazol-2(3H)-one; and tautomers, pharmaceutically acceptable salts, solvates, clathrates, and prodrugs thereof.

The present invention also provides compounds having the formula (X):

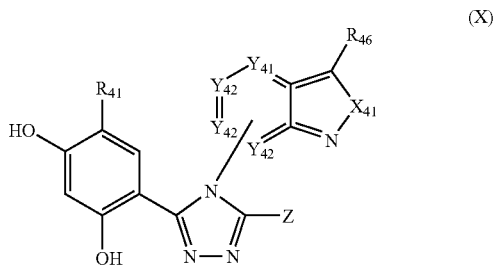

and tautomers, pharmaceutically acceptable salts, solvates, clathrates, and prodrugs thereof, wherein:

$X_{41}$, $Y_{41}$, $Y_{42}$, Z, $R_7$, $R_8$, $R_{10}$, $R_{11}$, $R_{41}$, $R_{46}$ and p are defined as above.

The compounds shown in Table 1 or compounds of any formula herein, or tautomers, pharmaceutically acceptable salts, solvates, clathrates, hydrates, polymorphs or prodrugs thereof, inhibit the activity of Hsp90 and, thereby facilitates the degradation of Hsp90 client proteins. Hsp90 is necessary for the survival of normal eukaryotic cells. The compounds shown in Table 1 or compounds of any formula herein, or tautomers, pharmaceutically acceptable salts, solvates, clathrates, hydrates, polymorphs or prodrugs thereof, are useful for treating, reducing or inhibiting angiogenesis. The compounds shown in Table 1 or compounds of any formula herein, or tautomers, pharmaceutically acceptable salts, solvates, clathrates, hydrates, polymorphs or prodrugs are also useful for reducing, blocking, occluding, or otherwise disrupting blood flow in neovasculature.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
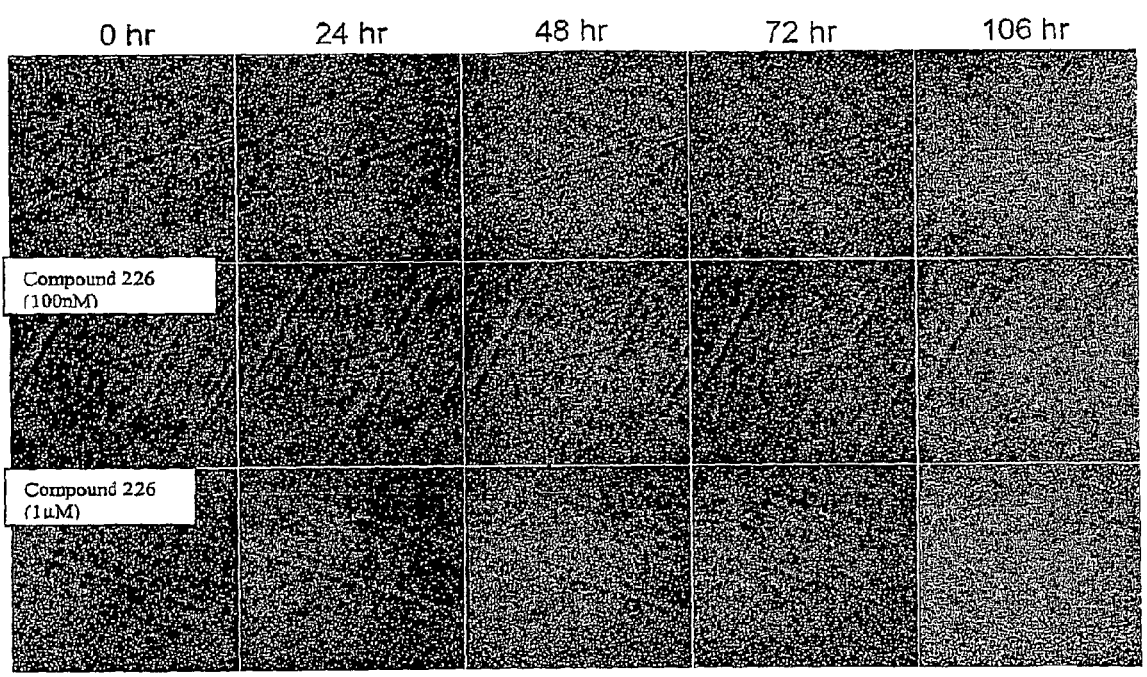
FIG. 1 is an image of the effect of Compound 226 on HUVEC migration at different points in time (0, 24, 48, 72, and 106 hours) and at two concentrations (100 nM and 1 µM) in comparison to DMSO treated cells.

A description of preferred embodiments of the invention follows.

The present invention provides compounds and uses of said compounds. The present invention encompasses the use of the compounds of the invention to treat or inhibit (e.g., reduce) angiogenesis. The present invention also provides methods for reducing, blocking, occluding, or otherwise disrupting blood flow in neovasculature.

In certain embodiments, the compounds of the invention can be used in combination with other therapies. In one aspect, compounds of the invention can be used in combination with other anti-angiogenic agents.

A. Terminology

Unless otherwise specified, the below terms used herein are defined as follows:

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "$(C_1$-$C_6)$alkyl" means a saturated straight chain or branched non-cyclic hydrocarbon having from 1 to 6 carbon atoms. Representative $(C_1$-$C_6)$alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon, having from 2 to 10 carbon atoms and having at least one carbon-carbon double bond. Representative straight chain and branched $(C_2$-$C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydropentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, an "haloalkoxy" is an haloalkyl group which is attached to another moiety via an oxygen linker.

As used herein, the term an "aromatic ring" or "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1$-$C_6)$alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "$(C_1$-$C_6)$alkylene" refers to an alkylene group that has from one to six carbon atoms. Straight chain $(C_1$-$C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or a unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "$(C_5)$heteroaryl" means an aromatic heterocyclic ring of 5 members, wherein at least one carbon atom of the ring is replaced with a heteroatom such as, for example, oxygen, sulfur or nitrogen. Representative $(C_5)$ heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "$(C_6)$heteroaryl" means an aromatic heterocyclic ring of 6 members, wherein at least one carbon atom of the ring is replaced with a heteroatom such as, for example, oxygen, nitrogen or sulfur. Representative $(C_6)$ heteroaryls include pyridyl, pyridazinyl, pyrazinyl, triazinyl, tetrazinyl and the like.

As used herein, the term "heteroaralkyl" means a heteroaryl group that is attached to another group by a $(C_1$-$C_6)$ alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)$NR_{28}R_{29}$, —C(S)$NR_{28}R_{29}$, —C($NR_{32}$)$NR_{28}R_{29}$, —$NR_{30}$C(O)$R_{31}$, —$NR_{30}$C(S)$R_{31}$, —$NR_{30}$C($NR_{32}$)$R_{31}$, halo, —$OR_{30}$, cyano, nitro, haloalkoxy, —C(O)$R_{30}$, —C(S)$R_{30}$, —C($NR_{32}$)$R_{30}$, —$NR_{28}R_{29}$, —C(O)$OR_{30}$, —C(S)$OR_{30}$, —C($NR_{32}$)$OR_{30}$, —OC(O)$R_{30}$, —OC(S)$R_{30}$, —OC($NR_{32}$)$R_{30}$, —$NR_{30}$C(O)$NR_{28}R_{29}$, —$NR_{30}$C(S)$NR_{28}R_{29}$, —$NR_{30}$C $(NR_{32})NR_{28}R_{29}$, $-OC(O)NR_{28}R_{29}$, $-OC(S)NR_{28}R_{29}$, $-OC(NR_{32})NR_{28}R_{29}$, $-NR_{30}C(O)OR_{31}$, $-NR_{30}C(S)OR_{31}$, $-NR_{30}C(NR_{32})OR_{31}$, $-S(O)_hR_{30}$, $-OS(O)_pR_{30}$, $-NR_{30}S(O)_pR_{30}$, $-S(O)_pNR_{28}R_{29}$, $-OS(O)_pNR_{28}R_{29}$, or $-NR_{30}S(O)_pNR_{28}R_{29}$, wherein $R_{28}$ and $R_{29}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{28}$ and $R_{29}$ taken together with the nitrogen to which they are attached is optionally substituted heterocyclyl or optionally substituted heteroaryl;

$R_{30}$ and $R_{31}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; and $R_{32}$, for each occurrence is, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, $-C(O)R_{30}$, $-C(O)NR_{28}R_{29}$, $-S(O)_pR_{30}$, or $-S(O)_pNR_{28}R_{29}$;

p, for each occurrence, is independently, 1 or 2; and h is 0, 1 or 2.

In addition, alkyl, cycloalkyl, alkylene, a heterocyclyl, and any saturated portion of a alkenyl, cycloalkenyl, alkynyl, aralkyl, and heteroaralkyl groups, may also be substituted with $=O$, $=S$, $=N-R_{32}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "lower" refers to a group having up to four atoms. For example, a "lower alkyl" refers to an alkyl radical having from 1 to 4 carbon atoms, "lower alkoxy" refers to "$-O-(C_1-C_4)$alkyl and a "lower alkenyl" or "lower alkynyl" refers to an alkenyl or alkynyl radical having from 2 to 4 carbon atoms, respectively.

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one ore more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxycarbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

As used herein, the term "compound(s) of this invention" and similar terms refers to a compound of formula (I), (II), (III), (IV), (V), (VI), (VII), (VIII), (IX), (X), or Table 1, or a pharmaceutically acceptable salt, solvate, clathrate, hydrate, polymorph or prodrug thereof, and also include protected derivatives thereof.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, he term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I), (II), (III), (IV), (V), (VI), (VII), (VIII), (IX), (X), or Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I), (II), (III), (IV), (V), (VI), (VII), (VIII), (IX), (X), or Table 1 that comprise —NO, —$NO_2$, —ONO, or —$ONO_2$ moieties. Prodrugs can typically be prepared using well-known methods, such as those described by 1 Burger'sMedicinal Chemistry and Drug Discovery (1995) 172-178, 949-982 (Manfred E. Wolff ed., $5^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "Hsp90" includes each member of the family of heat shock proteins having a mass of about 90-kiloDaltons. For example, in humans the highly conserved Hsp90 family includes cytosolic Hsp90α and Hsp90β isoforms, as well as GRP94, which is found in the endoplasmic reticulum, and HSP75/TRAP1, which is found in the mitochondrial matrix.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors, Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 *of Holland Frie Cancer Medicine* 5th Ed., Bast et al. Eds., B.C. Decker Inc. (2000). The entire teachings of the preceding references are incorporated herein by reference.

As used herein the term "multi-drug resistant cancer" refers to a cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

As used herein, the term "pharmaceutically acceptable salt," is a salt formed from, for example, an acid and a basic group of one of the compounds of formula (I), (II), (III), (IV), (V), (VI), (VII), (VIII), (IX), (X), or Table 1. Illustrative salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of formula (I), (II), (III), (IV), (V), (VI), (VII), (VIII), (IX), (X), or Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formula (I), (II), (III), (IV), (V), (VI), (VII), (VIII), (IX), (X), or Table 1 having a basic functional group, such as an amine functional group, and a pharmaceutically acceptable inorganic or organic acid. Suitable acids include, but are not limited to, hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

In one embodiment, compounds of the invention are vascular targeting agents. In one aspect, compounds of the invention are effective for reducing, blocking, occluding, or otherwise disrupting blood flow in "neovasculature." In one aspect, the invention provides a novel treatment for diseases involving the growth of new blood vessels ("neovasculature"), including, but not limited to: cancer; infectious diseases; autoimmune disorders; benign tumors, e.g. hemangiomas, acoustic neuromas, neurofibromas, trachomas, and pyogenic granulomas; artheroscleric plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal neovascularization, uvietis and Pterygia (abnormal blood vessel growth) of the eye; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; HHT; transplant arteriopathy; restinosis; obesity; myocardial angiogenesis; coronary collaterals; cerebral collaterals; arteriovenous malformations; ischemic limb angiogenesis; primary pulmonary hypertension; pulmonary edema; asthma; nasal polyps; inflammatory bowel disease; periodontal disease; ascites; peritoneal adhesions; Osler-Webber Syndrome; plaque neovascularization; telangiectasia; hemophiliac joints; synovitis; osteomyelitis; osteophyte formation; angiofibroma; fibromuscular dysplasia; wound granulation; Crohn's disease; and atherosclerosis.

Vascular targeting can be demonstrated by any method known to those skilled in the art, such as the method described herein in Examples 170 and 171.

As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin discolorations (e.g., hemangioma, nevus flammeus, or nevus simplex); wound healing; hypertrophic scars, i.e., keloids; wound granulation; vascular adhesions; cat scratch disease (Rochele ninalia quintosa); ulcers (*Helicobacter pylori*); keratoconjunctivitis; gingivitis; periodontal disease; epulis; hepatitis; tonsillitis; obesity; rhinitis; laryngitis; tracheitis; bronchitis; bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease.

As used herein, the term "pharmaceutically acceptable solvate," is a solvate formed from the association of one or more pharmaceutically acceptable solvent molecules to one of the compounds of formula (I), (II), (III), (IV), (V), (VI), (VII), (VIII), (IX), (X), or Table 1. The term solvate includes hydrates (e.g., hemihydrate, monohydrate, dihydrate, trihydrate, tetrahydrate, and the like).

A pharmaceutically acceptable carrier may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

As used herein, the term "effective amount" refers to an amount of a compound of this invention which is sufficient to reduce or ameliorate the severity, duration, progression, or onset of an angiogenesis related disorder, prevent the advancement of a an angiogenesis related disorder, cause the regression of an angiogenesis related disorder, prevent the recurrence, development, onset or progression of a symptom associated with an angiogenesis related disorder, or enhance or improve the prophylactic or therapeutic effect(s) of another therapy. In one embodiment, the term refers to the amount of the compound needed to reduce, block, occlude, or otherwise disrupt blood flow in neovasculature. The precise amount of compound administered to a subject will depend on the mode of administration, the type and severity of the disease or condition and on the characteristics of the subject, such as general health, age, sex, body weight and tolerance to drugs. It will also depend on the degree, severity and type of the angiogenesis related, and the mode of administration. The skilled artisan will be able to determine appropriate dosages depending on these and other factors. When co-administered with other agents, e.g., when co-administered with a chemotherapeutic agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

Non-limiting examples of an effective amount of a compound of the invention are provided herein below. In a specific embodiment, the invention provides a method of preventing, treating, managing, or ameliorating an angiogenisis related disorder or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

The dosages of a chemotherapeutic agents other than compounds of the invention, which have been or are currently being used to prevent, treat, manage, or ameliorate a proliferative disorder, or one or more symptoms thereof, can be used in the combination therapies of the invention. Preferably, dosages lower than those which have been or are currently being used to prevent, treat, manage, or ameliorate a proliferative disorder, or one or more symptoms thereof, are used in the combination therapies of the invention. The recommended dosages of agents currently used for the prevention, treatment, management, or amelioration of a proliferative disorder, or one or more symptoms thereof, can obtained from any reference in the art including, but not limited to, Hardman et al., eds., 1996, Goodman & Gilman's The Pharmacological Basis Of Basis Of Therapeutics 9th Ed, McGraw-Hill, New York; Physician's Desk Reference (PDR) 57th Ed., 2003, Medical Economics Co., Inc., Montvale, N.J., which are incorporated herein by reference in its entirety.

As used herein, the terms "treat", "treatment" and "treating" refer to the reduction or amelioration of the progression, severity and/or duration of a disease or disorder, or the amelioration of one or more symptoms (preferably, one or more discernible symptoms) of a disease or disorder resulting from the administration of one or more therapies (e.g., one or more therapeutic agents such as a compound of the invention). In specific embodiments, the terms "treat", "treatment" and "treating" refer to the amelioration of at least one measurable physical parameter of an angiogenesis related disorder, not necessarily discernible by the patient. In other embodiments the terms "treat", "treatment" and "treating" refer to the inhibition (e.g., reduction) of the progression of an angiogenesis related disorder, either physically by, e.g., stabilization of a discernible symptom, physiologically by, e.g., stabilization of a physical parameter, or both. In other embodiments the terms "treat", "treatment" and "treating" refers to reduce, blocking, occluding, or otherwise disrupting blood flow in neovasculature.

As used herein, the terms "prevent", "prevention" and "preventing" refer to the reduction in the risk of acquiring or developing a disease or disorder, or the reduction or inhibition of the recurrence or a disease or disorder. In one embodiment, a compound of the invention is administered as a preventative measure to a patient, preferably a human, having a genetic predisposition to any of the disorders described herein.

As used herein, the terms "therapeutic agent" and "therapeutic agents" refer to any agent(s) which can be used in the treatment, management, or amelioration of a disease or disorder or one or more symptoms thereof. In certain embodiments, the term "therapeutic agent" refers to a compound of the invention. In certain other embodiments, the term "therapeutic agent" refers does not refer to a compound of the invention. Preferably, a therapeutic agent is an agent which is known to be useful for, or has been or is currently being used for the treatment, management, prevention, or amelioration of an angiogenesis related disorder or one or more symptoms thereof.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a proliferative disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a proliferative disorder. In addition, a synergistic effect can result in improved efficacy of agents in the prevention, management or treatment of an angiogenesis related disorder. Finally, a synergistic effect of a combination of therapies (e.g., a combination of prophylactic or therapeutic agents) may avoid or reduce adverse or unwanted side effects associated with the use of either therapy alone.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapies (e.g., one or more prophylactic and/or therapeutic agents). The use of the term "in combination" does not restrict the order in which therapies (e.g., prophylactic and/or therapeutic agents) are administered to a subject with a disease or disorder. A first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject with an angiogenesis related disorder, such as macular degeneration.

As used herein, the terms "therapies" and "therapy" can refer to any protocol(s), method(s), and/or agent(s) that can be used in the prevention, treatment, management, or amelioration of an angiogenesis related disorder or one or more symptoms thereof.

A used herein, a "protocol" includes dosing schedules and dosing regimens. The protocols herein are methods of use and include prophylactic and therapeutic protocols.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to a chiral center in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to a non-human animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of (a) a natural source, such as a plant or cell, preferably bacterial culture, or (b) a synthetic organic chemical reaction mixture. Preferably, the compounds of the invention are purified via conventional techniques. As used herein, "purified" means that when isolated, the isolate contains at least 95%, preferably at least 98%, of a compound of the invention by weight of the isolate either as a mixture of stereoisomers or as a diastereomeric or enantiomeric pure isolate.

As used herein, a composition that is "substantially free" of a compound means that the composition contains less than about 20% by weight, more preferably less than about 10% by weight, even more preferably less than about 5% by weight, and most preferably less than about 3% by weight of the compound.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

B. The Compounds of the Invention

The present invention encompasses compounds having Formulas (I), (II), (III), (IV), (V), (VI), (VII), (VIII), (IX), (X), and those set forth in Table 1 and tautomers, pharmaceutically acceptable salts, solvates, clathrates, hydrates, polymorphs and prodrugs thereof. In one aspect, the invention provides compounds of formula (I) as set forth below:

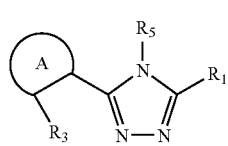
(I)

and tautomers, pharmaceutically acceptable salts, solvates, clathrates, and prodrugs thereof, wherein ring A, $R_1$, $R_3$ and $R_5$ are defined as above.

Compounds of formula (I) inhibit the activity of Hsp90 and are particularly useful for treating or preventing (e.g., reduce the likelihood of developing) angiogenesis related disorders, such as macular degeneration. In addition, compounds of formula (I) are particularly useful in reducing, blocking, occluding, or otherwise disrupting blood flow in neovasculature.

In one embodiment, in the compounds of formula (I), $R_5$ is an optionally substituted naphthyl.

In another embodiment, in the compounds of formula (I), $R_5$ is represented by the following formula:

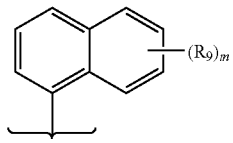

wherein:

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, or —$SP(O)(OR_7)_2$;

or two $R_9$ groups taken together with the carbon atoms to which they are attached form a fused ring; and m is zero or an integer from 1 to 7, wherein $R_7$, $R_8$, $R_{10}$, $R_{11}$, and p are defined as above.

In another embodiment, in the compounds represented by formula (I), $R_5$ is represented by one of the following formulas:

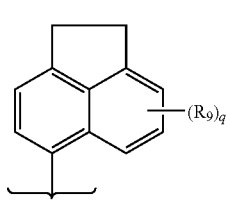 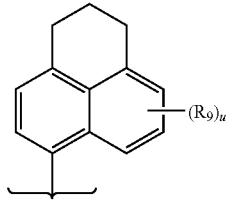

wherein $R_9$ is defined as above;
q is zero or an integer from 1 to 7; and
u is zero or an integer from 1 to 8.

In another embodiment, in the compounds represented by formula (I), $R_5$ is selected from the group consisting of:

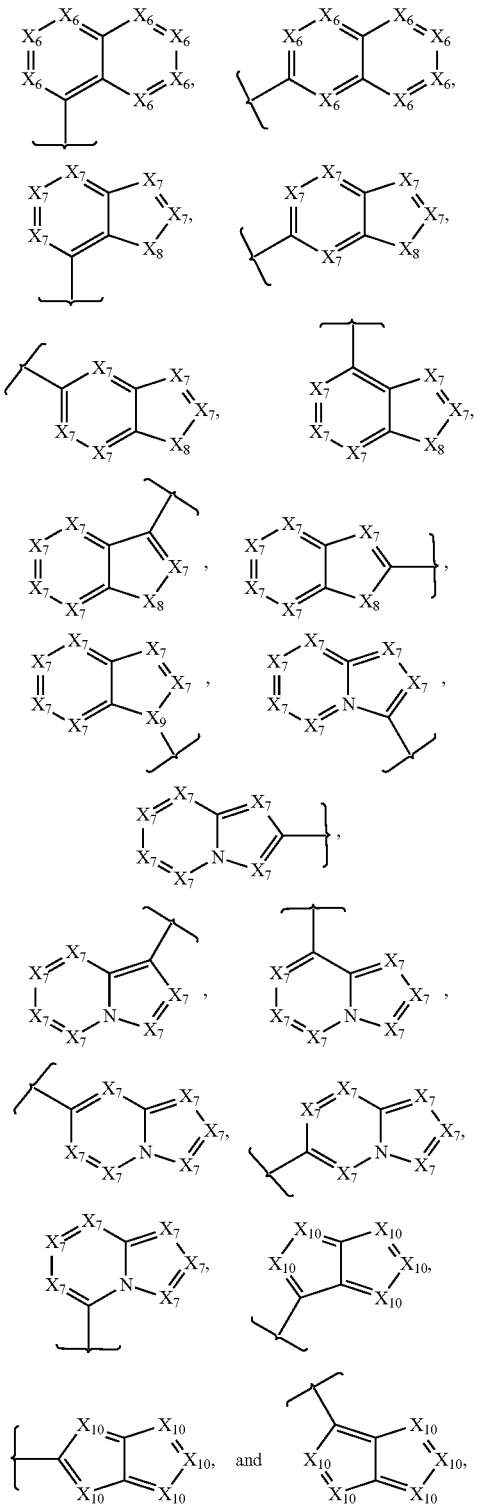

wherein:

$X_6$, for each occurrence, is independently CH, $CR_9$, N, N(O), $N^+(R_{17})$, provided that at least three $X_6$ groups are independently selected from CH and $CR_9$;

$X_7$, for each occurrence, is independently CH, $CR_9$, N, N(O), $N^+(R_{17})$, provided that at least three $X_7$ groups are independently selected from CH and $CR_9$;

$X_8$, for each occurrence, is independently $CH_2$, $CHR_9$, $CR_9R_9$, O, S, S(O)p, $NR_7$, or $NR_{17}$;

$X_9$, for each occurrence, is independently N or CH;

$X_{10}$, for each occurrence, is independently CH, $CR_9$, N, N(O), $N^+(R_{17})$, provided that at least one $X_{10}$ is selected from CH and $CR_9$;

$R_{17}$, for each occurrence, is independently —H, an alkyl, an aralkyl, —C(O)$R_7$, —C(O)O$R_7$, or —C(O)$NR_{10}R_{11}$; wherein $R_7$, $R_9$, $R_{10}$, $R_{11}$ and p are defined as above.

In another embodiment, in the compounds represented by formula (I), $R_5$ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

In another embodiment, in the compounds represented by formula (I), $R_5$ is an optionally substituted indolyl. Preferably, $R_5$ is an indolyl represented by the following structural formula:

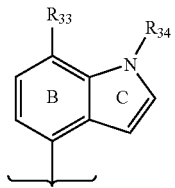

wherein:

$R_{33}$ is a halo, lower alkyl, a lower alkoxy, a lower haloalkyl, a lower haloalkoxy, and lower alkyl sulfanyl;

$R_{34}$ is H, a lower alkyl, or a lower alkylcarbonyl; and

Ring B and Ring C are optionally substituted with one or more substituents.

In another embodiment, in the compounds represented by formula (I), $R_5$ is selected from the group consisting of:

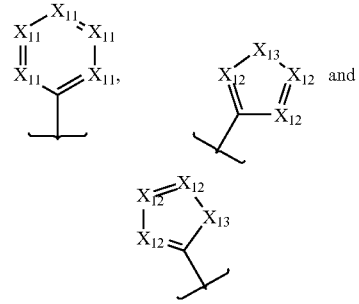

wherein:

$X_{11}$, for each occurrence, is independently CH, $CR_9$, N, N(O), or $N^+(R_{17})$, provided that at least one $X_{11}$ is N, N(O), or $N^+(R_{17})$ and at least two $X_{11}$ groups are independently selected from CH and $CR_9$;

$X_{12}$, for each occurrence, is independently CH, $CR_9$, N, N(O), $N^+(R_{17})$, provided that at least one $X_{12}$ group is independently selected from CH and $CR_9$;

$X_{13}$, for each occurrence, is independently O, S, S(O)p, $NR_7$, or $NR_{17}$; wherein $R_7$, $R_9$ and $R_{17}$ are defined as above.

In another embodiment, in compounds represented by formula (I), or any of the embodiments of formula (I) in which particular groups are disclosed, the compound is represented by the following structural formula:

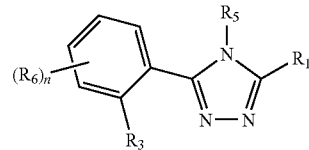

wherein $R_1$, $R_3$, and $R_5$ are defined as above; and $R_6$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —$NR_{10}R_{11}$, —$OR_7$, —C(O)$R_7$, —C(O)O$R_7$, —C(S)$R_7$, —C(O)S$R_7$, —C(S)S$R_7$, —C(S)O$R_7$, —C(S)$NR_{10}R_{11}$, —C($NR_8$)O$R_7$, —C($NR_8$)$R_7$, —C($NR_8$)$NR_{10}R_{11}$, —C($NR_8$)S$R_7$, —OC(O)$R_7$, —OC(O)O$R_7$, —OC(S)O$R_7$, —OC($NR_8$)O$R_7$, —SC(O)$R_7$, —SC(O)O$R_7$, —SC($NR_8$)O$R_7$, —OC(S)$R_7$, —SC(S)$R_7$, —SC(S)O$R_7$, —OC(O)$NR_{10}R_{11}$, —OC(S)$NR_{10}R_{11}$, —OC($NR_8$)$NR_{10}R_{11}$, —SC(O)$NR_{10}R_{11}$, —SC($NR_8$)$NR_{10}R_{11}$, —SC(S)$NR_{10}R_{11}$, —OC($NR_8$)$R_7$, —SC($NR_8$)$R_7$, —C(O)$NR_{10}R_{11}$, —$NR_7$C(O)$R_7$, —$NR_7$C(S)$R_7$, —$NR_7$C(S)O$R_7$, —$NR_7$C($NR_8$)$R_7$, —$NR_7$C(O)O$R_7$, —$NR_7$C($NR_8$)O$R_7$, —$NR_7$C(O)$NR_{10}R_{11}$, —$NR_7$C(S)$NR_{10}R_{11}$, —$NR_7$C($NR_8$)$NR_{10}R_{11}$, —$SR_7$, —S(O)$_pR_7$, —OS(O)$_pR_7$, —OS(O)$_pOR_7$, —OS(O)$_pNR_{10}R_{11}$, —S(O)$_pOR_7$, —$NR_8$S(O)$_pR_7$, —$NR_7$S (O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$; and n is zero of an integer from 1 to 4, wherein R$_7$, R$_8$, R$_{10}$, R$_{11}$, and p are defined as above.

In another embodiment, in compounds represented by formula (I), or any of the embodiments of formula (I) in which particular groups are disclosed, the compound is represented by the following structural formula:

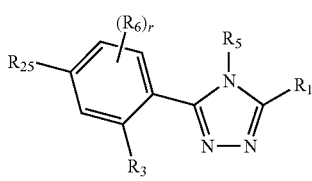

wherein R$_1$, R$_3$, R$_5$, and R$_6$ are defined as above; and

R$_{25}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$;

k is 1, 2, 3, or 4; and r is zero or an integer from 1 to 3, wherein R$_7$, R$_8$, R$_{10}$, R$_{11}$, and p are defined as above.

In another embodiment of the compound represented by the above formula, R$_1$, R$_3$ and R$_{25}$ are each independently —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$.

In another embodiment of the compound represented by the above formula, R$_1$ and R$_3$ are each, independently, —OH, —SH, or —NHR$_7$. In this case, R$_6$ can be an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$.

In another embodiment of the above compound, R$_1$ is —SH or —OH; R$_3$ and R$_{25}$ are —OH; R$_6$ is a lower alkyl, C3-C6 cycloalkyl, lower alkoxy, a lower alkyl sulfanyl, or —NR$_{10}$R$_{11}$; and R$_9$, for each occurrence, is independently selected from the group consisting of —OH, —SH, halo, a lower haloalkyl, cyano, a lower alkyl, a lower alkoxy, and a lower alkyl sulfanyl.

In another embodiment, in compounds represented by formula (I), or any of the embodiments of formula (I) in which particular groups are disclosed, R$_1$ and R$_3$ are each, independently, —OH, —SH, or —NHR$_7$.

In another embodiment, in compounds represented by formula (I), or any of the embodiments of formula (I) in which particular groups are disclosed, the compound is represented by the following structural formula:

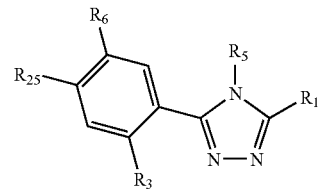

wherein R$_1$, R$_3$, R$_5$, and R$_{25}$ are defined as above; and

R$_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$, wherein R$_7$, R$_8$, R$_{10}$, R$_{11}$, and p are defined as above. In a preferred embodiment, R$_1$ is —SH or —OH; R$_3$ and R$_{25}$ are —OH; R$_{12}$ is a lower alkyl, lower alkoxy, a lower alkyl sulfanyl, or —NR$_{10}$R$_{11}$; and R$_9$, for each occurrence, is independently selected from the group consisting of —OH, —SH, halo, a lower haloalkyl, cyano, a lower alkyl, a lower alkoxy, and a lower alkyl sulfanyl.

In another embodiment, in compounds represented by formula (I), or any of the embodiments of formula (I) in which particular groups are disclosed, the compound is represented by one of the following structural formulas:

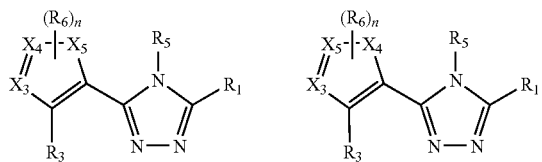

wherein R$_1$, R$_3$, R$_5$, R$_6$ and n are as defined above; and

X$_3$ and X$_4$ are each, independently, N, N(O), N$^+$(R$_{17}$), CH or CR$_6$; and X$_5$ is O, S, NR$_{17}$, CH═CH, CH═CR$_6$, CR$_6$═CH, CR$_6$═CR$_6$, CH═N, CR$_6$═N, CH═N(O), CR$_6$═N(O), N═CH, N═CR$_6$, N(O)═CH, N(O)═CR$_6$, N$^+$(R$_{17}$)═CH, N$^+$(R$_{17}$)═CR$_6$, CH═N$^+$(R$_{17}$), CR$_6$═N$^+$(R$_{17}$), or N═N; wherein R$_{17}$ is defined as above.

In another embodiment, in compounds represented by formula (I), or any of the embodiments of formula (I) in which particular groups are disclosed, the compound is selected from the group consisting of:

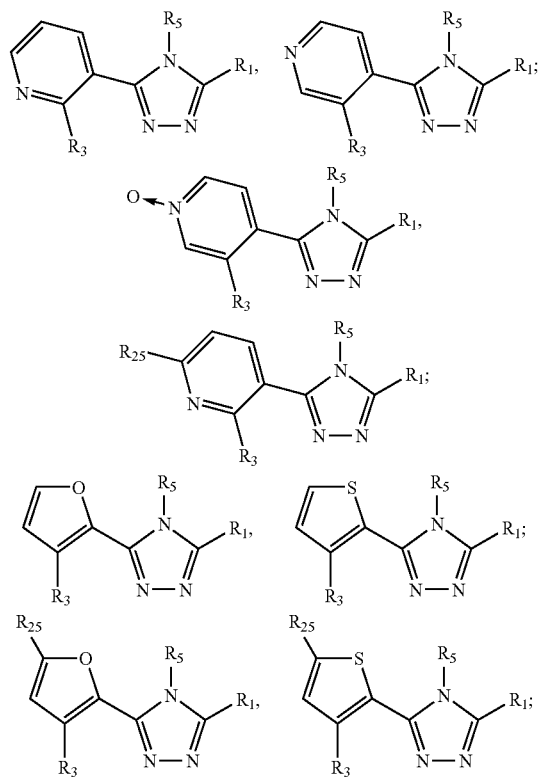

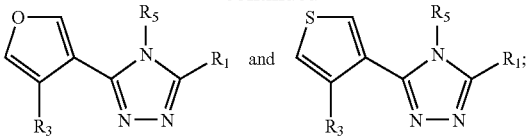

wherein R$_1$, R$_3$, R$_5$, and R$_{25}$ are defined as above.

In another aspect, the invention provides compounds of formula (II) as set forth below:

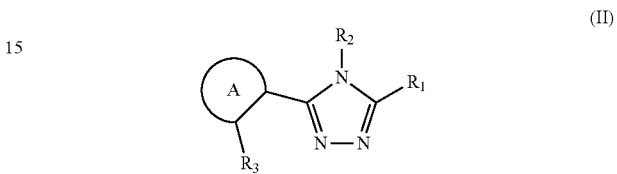

and tautomers, pharmaceutically acceptable salts, solvates, clathrates, and prodrugs thereof, wherein ring A, R$_1$ and R$_3$ are defined as above; and R$_2$ is a substituted phenyl, wherein the phenyl group is substituted with:
  i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxylalkyl, alkoxyalkyl, guanadino, —NR$_{10}$R$_{11}$, —O—R$_{20}$, —C(O)R$_7$, —C(O)OR$_{20}$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, or
  ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, —F, —Br, —I, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

R$_{20}$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

p, for each occurrence, is, independently, 1 or 2.

Compounds of formula (II) inhibit the activity of Hsp90 and are particularly useful for treating or preventing (e.g., reducing the likelihood of developing) angiogenesis related disorders, such as macular degeneration. In addition, compounds of formula (II) are particularly useful in reducing, blocking, occluding, or otherwise disrupting blood flow in neovasculature.

In one embodiment, the compounds represented by formula (II) do not include 3-(2,4-dihydroxy-phenyl)-4-(7-naphthalen-1-yl)-5-mercapto-triazole, 3-(2,4-dihydroxyphenyl)-4-(2,5-dimethoxyphenyl)-5-mercapto-triazole, 3-(1-phenyl-5-amino-pyrazol-4-yl)-4-(2,4-dichloropheny)-5-mercapto-triazole, and 3-(2-hydroxy-phenyl)4-(2,4-dimethylphenyl)-5-mercapto-triazole.

In another embodiment, in compounds represented by formula (II), or any of the embodiments of formula (II) in which particular groups are disclosed, the compound is represented by the following structural formula:

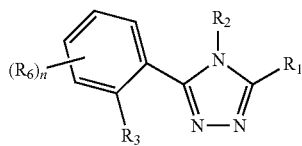

wherein $R_1$, $R_2$, $R_3$, $R_6$, and n are defined as above.

In another embodiment, in compounds represented by formula (II), or any of the embodiments of formula (II) in which particular groups are disclosed, the compound is represented by the following structural formula:

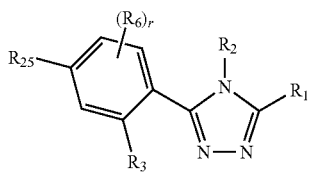

wherein $R_1$, $R_2$, $R_3$, $R_6$, $R_{25}$ and r are defined as above.

In another embodiment, in compounds represented by formula (II), or any of the embodiments of formula (II) in which particular groups are disclosed, $R_1$ and $R_3$ are each, independently, —OH, —SH, or —NHR$_7$.

In another embodiment, in compounds represented by formula (II), or any of the embodiments of formula (II) in which particular groups are disclosed, the compound is represented by the following structural formula:

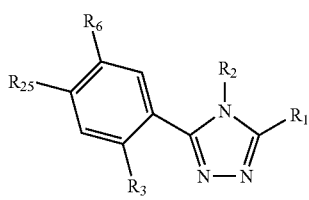

wherein $R_1$, $R_2$, $R_3$, $R_6$ and $R_{25}$ are defined as above. In a preferred embodiment, $R_1$ is —SH or —OH; $R_3$ and $R_{25}$ are —OH; $R_{12}$ is a lower alkyl, lower alkoxy, a lower alkyl sulfanyl, or —NR$_{10}$R$_{11}$; and $R_9$, for each occurrence, is independently selected from the group consisting of —OH, —SH, halo, a lower haloalkyl, cyano, a lower alkyl, a lower alkoxy, and a lower alkyl sulfanyl.

In another embodiment, in compounds represented by formula (II), or any of the embodiments of formula (II) in which particular groups are disclosed, the compound is represented by one of the following structural formulas:

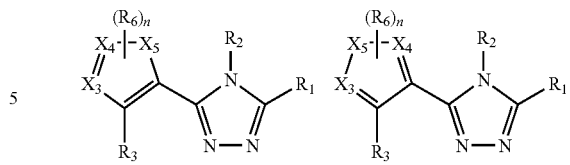

wherein $R_1$, $R_2$, $R_3$, $R_6$, $X_3$, $X_4$, $X_5$ and n are defined as above.

In another embodiment, in compounds represented by formula (II), or any of the embodiments of formula (II) in which particular groups are disclosed, the compound is selected from the group consisting of:

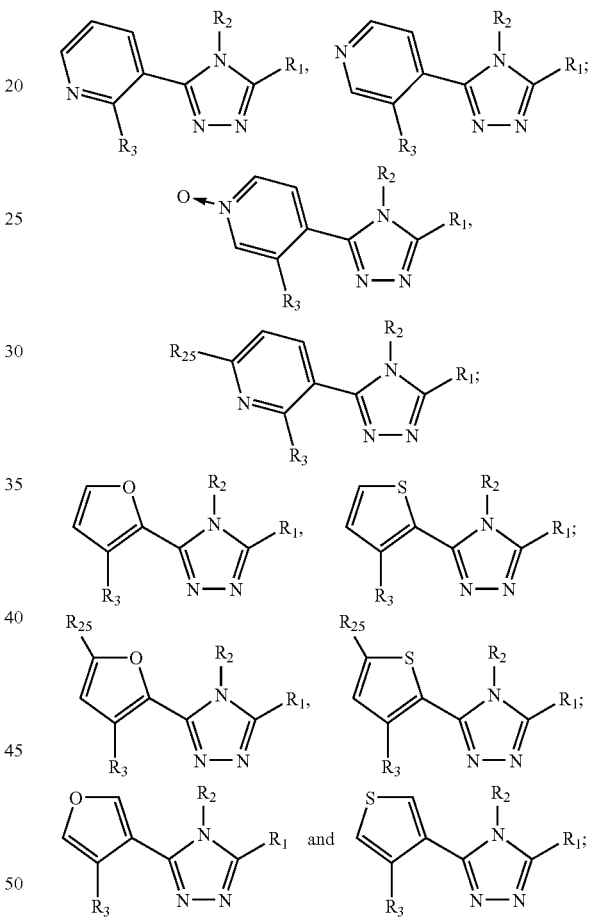

wherein $R_1$, $R_2$, $R_3$, and $R_{25}$ are defined as above.

In another aspect, the invention provides compounds of formula (III) as set forth below:

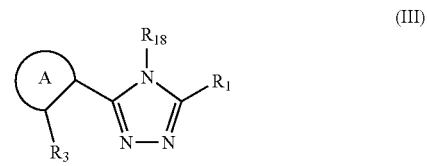

and tautomers, pharmaceutically acceptable salts, solvates, clathrates, and prodrugs. In formula (III), ring A, $R_1$, and $R_3$ are defined as above; and $R_{18}$ is an optionally substituted cycloalkyl, and optionally substituted cycloalkenyl, or a substituted alkyl, wherein the alkyl group is substituted with one or more substituents independently selected from the group consisting of an optionally substituted alkynyl, an optionally substituted cycloalkyl, an optionally substituted cycloalkenyl, an optionally substituted heteroaryl, an optionally substituted aralkyl, an optionally substituted heteraralkyl, halo, cyano, nitro, guanadino, a haloalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, wherein $R_7$, $R_8$, $R_{10}$, $R_{11}$, and p are defined as above.

Compounds of formula (III) inhibit the activity of Hsp90 and are particularly useful for treating or preventing (e.g., reducing the likelihood of developing) angiogenesis related disorders, such as macular degeneration. In addition, compounds of formula (III) are particularly useful in reducing, blocking, occluding, or otherwise disrupting blood flow in neovasculature. In one embodiment, in formula (III) $R_{18}$ is not cyclohexyl.

In another embodiment, in formula (III) $R_{18}$ is an optionally substituted cycloalkyl or an optionally substituted cycloalkenyl.

In another embodiment, in formula (III) $R_{18}$ is a substituted alkyl.

In another embodiment, in compounds represented by formula (III), or any of the embodiments of formula (III) in which particular groups are disclosed, the compound is represented by the following structural formula:

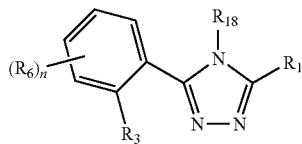

wherein $R_1$, $R_3$, $R_6$, $R_{18}$, and n are defined as above.

In another embodiment, in compounds represented by formula (III), or any of the embodiments of formula (III) in which particular groups are disclosed, the compound is represented by the following structural formula:

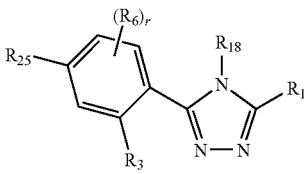

wherein $R_1$, $R_3$, $R_6$, $R_{18}$, $R_{25}$ and r are defined as above.

In another embodiment, in compounds represented by formula (III), or any of the embodiments of formula (III) in which particular groups are disclosed, $R_1$ and $R_3$ are each, independently, —OH, —SH, or —$NHR_7$.

In another embodiment, in compounds represented by formula (III), or any of the embodiments of formula (III) in which particular groups are disclosed, the compound is represented by the following structural formula:

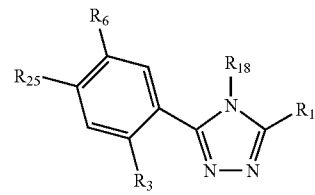

wherein $R_1$, $R_3$, $R_6$, $R_{18}$, and $R_{25}$ are defined as above. In a preferred embodiment, $R_1$ is —SH or —OH; $R_3$ and $R_{25}$ are —OH; and $R_{12}$ is a lower alkyl, lower alkoxy, a lower alkyl sulfanyl, or —$NR_{10}R_{11}$.

In another embodiment, in compounds represented by formula (III), or any of the embodiments of formula (III) in which particular groups are disclosed, the compound is represented by one of the following structural formulas:

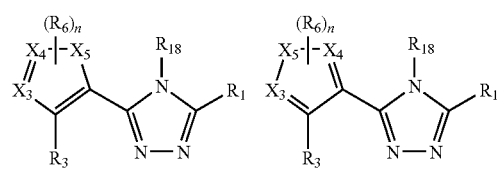

wherein $R_1$, $R_3$, $R_6$, $R_{18}$, $X_3$, $X_4$, $X_5$, and n are defined as above.

In another embodiment, in compounds represented by formula (III), or any of the embodiments of formula (III) in which particular groups are disclosed, the compound is selected from the group consisting of:

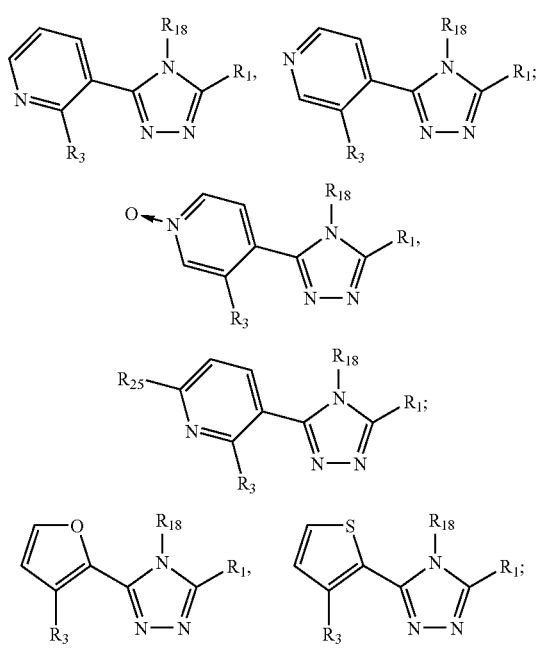

-continued

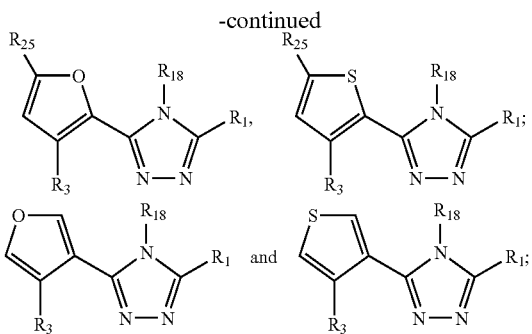

wherein $R_1$, $R_3$, $R_{18}$, and $R_{25}$ are defined as above.

In another aspect, the invention provides compounds of formula (IV) or (V) as set forth below:

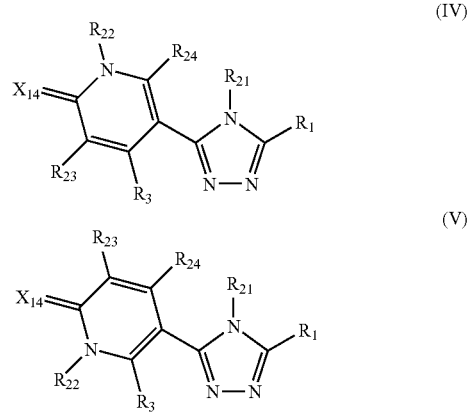

and tautomers, pharmaceutically acceptable salts, solvates, clathrates, and prodrugs thereof. In formulas (IV) and (V), $R_1$ and $R_3$ are as defined above; and $X_{14}$ is O, S, or $NR_7$;

$R_{21}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{22}$, for each occurrence, is independently an —H or is selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a haloalkyl, —C(O)$R_7$, —C(O)O$R_7$, —OC(O)$R_7$, —C(O)N$R_{10}R_{11}$, —N$R_8$C(O)$R_7$, —S(O)$_p R_7$, —S(O)$_p$O$R_7$, or —S(O)$_p$N$R_{10}R_{11}$; and $R_{23}$ and $R_{24}$, for each occurrence, are independently —H or are selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, halo, cyano, nitro, guanadino, a haloalkyl, a heteroalkyl, —N$R_{10}R_{11}$, —O$R_7$, —C(O)$R_7$, —C(O)O$R_7$, —OC(O)$R_7$, —C(O)N$R_{10}R_{11}$, —N$R_8$C(O)$R_7$, —S$R_7$, —S(O)$_p R_7$, —OS(O)$_p R_7$, —S(O)$_p$O$R_7$, —N$R_8$S(O)$_p R_7$, or —S(O)$_p$N$R_{10}R_{11}$;

wherein $R_7$, $R_8$, $R_{10}$, $R_{11}$ and p are defined as above.

In one embodiment, in formulas (IV) and (V), $R_{21}$ is an optionally substituted alkyl, an optionally substituted cycloalkyl, an optionally substituted aryl or an optionally substituted heteroaryl.

In another embodiment, in the formulas (IV) and (V), $R_1$ is —OH, —SH, or —NH$R_7$.

In another embodiment, in the formulas (IV) and (V), $R_{22}$ is —H, an alkyl, an aralkyl, —C(O)$R_7$, or —C(O)N$R_{10}R_{11}$.

In another embodiment, in the formulas (IV) and (V), $X_{14}$ is O.

Compounds of formula (IV) or (V) inhibit the activity of Hsp90 and are particularly useful for treating or preventing (e.g., reducing the likelihood of developing) angiogenesis related disorders, such as macular degeneration. In addition, compounds of formula (IV) or (V) are particularly useful in reducing, blocking, occluding, or otherwise disrupting blood flow in neovasculature.

In another aspect, the invention provides compounds represented by formula (VI):

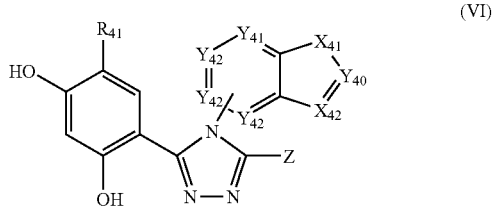

and tautomers, pharmaceutically acceptable salts, solvates, clathrates, and prodrugs thereof, wherein:

$X_{41}$ is O, S, or N$R_{42}$;

$X_{42}$ is C$R_{44}$ or N;

$Y_{40}$ is N or C$R_{43}$;

$Y_{41}$ is N or C$R_{45}$;

$Y_{42}$, for each occurrence, is independently N, C or C$R_{46}$;

Z is OH, SH, or NH$R_7$;

$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —N$R_{10}R_{11}$, —O$R_7$, —C(O)$R_7$, —C(O)O$R_7$, —C(S)$R_7$, —C(O)S$R_7$, —C(S)S$R_7$, —C(S)O$R_7$, —C(S)N$R_{10}R_{11}$, —C(N$R_8$)O$R_7$, —C(N$R_8$)$R_7$, —C(N$R_8$)N$R_{10}R_{11}$, —C(N$R_8$)S$R_7$, —OC(O)$R_7$, —OC(O)O$R_7$, —OC(S)O$R_7$, —OC(N$R_8$)O$R_7$, —SC(O)$R_7$, —SC(O)O$R_7$, —SC(N$R_8$)O$R_7$, —OC(S)$R_7$, —SC(S)$R_7$, —SC(S)O$R_7$, —OC(O)N$R_{10}R_{11}$, —OC(S)N$R_{10}R_{11}$, —OC(N$R_8$)N$R_{10}R_{11}$, —SC(O)N$R_{10}R_{11}$, —SC(N$R_8$)N$R_{10}R_{11}$, —SC(S)N$R_{10}R_{11}$, —OC(N$R_8$)$R_7$, —SC(N$R_8$)$R_7$, —C(O)N$R_{10}R_{11}$, —N$R_8$C(O)$R_7$, —N$R_7$C(S)$R_7$, —N$R_7$C(S)O$R_7$, —N$R_7$C(N$R_8$)$R_7$, —N$R_7$C(O)O$R_7$, —N$R_7$C(N$R_8$)O$R_7$, —N$R_7$C(O)N$R_{10}R_{11}$, —N$R_7$C(S)N$R_{10}R_{11}$, —N$R_7$C(N$R_8$)N$R_{10}R_{11}$, —S$R_7$, —S(O)$_p R_7$, —OS(O)$_p R_7$, —OS(O)$_p$O$R_7$, —OS(O)$_p$N$R_{10}R_{11}$, —S(O)$_p$O$R_7$, —N$R_8$S(O)$_p R_7$, —N$R_7$S(O)$_p$N$R_{10}R_{11}$, —N$R_7$S(O)$_p$O$R_7$, —S(O)$_p$N$R_{10}R_{11}$, —SS(O)$_p R_7$, —SS(O)$_p$O$R_7$, —SS(O)$_p$N$R_{10}R_{11}$, —OP(O)(O$R_7$)$_2$, or —SP(O)(O$R_7$)$_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —C(O)R$_7$, —(CH$_2$)$_m$C(O)OR$_7$, —C(O)OR$_7$, —OC(O)R$_7$, —C(O)NR$_{10}$R$_{11}$, —S(O)$_p$R$_7$, —S(O)$_p$OR$_7$, or —S(O)$_p$NR$_{10}$R$_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, —S(O)$_p$NR$_{10}$R$_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, or —NR$_7$C(NR$_8$)NR$_{10}$R$_{11}$;

$R_{46}$, for each occurrence, is independently selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

$R_7$, $R_8$, $R_{10}$, $R_{11}$, $R_{26}$, p, and m are defined as above.

In one embodiment, in formula (VI), $X_{41}$ is NR$_{42}$ and $X_{42}$ is CR$_{44}$.

In another embodiment, in formula (VI), $X_{41}$ is NR$_{42}$ and $X_{42}$ is N.

In another embodiment, in formula (VI), $R_{41}$ is selected from the group consisting of —H, lower alkyl, lower alkoxy, lower cycloalkyl, and lower cycloalkoxy.

In another embodiment, in formula (VI), $R_{41}$ is selected from the group consisting of —H, methyl, ethyl, propyl, isopropyl, cyclopropyl, methoxy, ethoxy, propoxy, and cyclopropoxy.

In another embodiment, in formula (VI), $X_{41}$ is NR$_{42}$, and $R_{42}$ is selected from the group consisting of —H, a lower alkyl, a lower cycloalkyl, —C(O)N(R$_{27}$)$_2$, and —C(O)OH, wherein R$_{27}$ is —H or a lower alkyl.

In another embodiment, in formula (VI), $X_{41}$ is NR$_{42}$, and $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In one embodiment, $Y_{40}$ is CR$_{43}$. Preferably, $Y_{40}$ is CR$_{43}$ and $R_{43}$ is H or a lower alkyl.

In another embodiment, in formula (VI), $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment, in formula (VI), $X_{42}$ is CR$_{44}$; Y is CR$_{43}$; and $R_{43}$ and $R_{44}$ together with the carbon atoms to which they are attached form a cycloalkenyl, an aryl, heterocyclyl, or heteroaryl ring. In one aspect of this embodiment, $R_{43}$ and $R_{44}$ together with the carbon atoms to which they are attached form a C$_5$-C$_8$ cycloalkenyl or a C$_5$-C$_8$ aryl.

In another embodiment, in formula (VI), $R_{45}$ is selected from the group consisting of —H, —OH, —SH, —NH$_2$, a lower alkoxy, a lower alkyl amino, and a lower dialkyl amino.

In another embodiment, in formula (VI), $R_{45}$ is selected from the group consisting of —H, —OH, methoxy and ethoxy.

In another embodiment, in formula (VI), $X_{41}$ is O.

In another embodiment, the compound is selected from the group consisting of:

3-(2,4-dihydroxy-5-ethyl-phenyl)-4-(2-methyl-7-methoxy-benzofuran-4-yl)-5-mercapto-[1,2,4]triazole, 3-(2,4-dihydroxy-5-ethyl-phenyl)-4-(benzofuran-5-yl)-5-mercapto-[1,2,4]triazole, 3-(2,4-dihydroxy-5-ethyl-phenyl)-4-(2-methyl-1,3-benzoxaz-5-yl)-5-mercapto-[1,2,4]triazole, and tautomers, pharmaceutically acceptable salts, solvates, clathrates, and prodrugs thereof.

In another embodiment, in formula (VI), Z is —OH.

In another embodiment, the compound is selected from the group consisting of:

3-(2,4-dihydroxy-5-ethyl-phenyl)-4-(1,3-dimethyl-indol-5-yl)-5-hydroxy-[1,2,4]triazole, 3-(2,4-dihydroxy-5-isopropyl-phenyl)-4-(1,3-dimethyl-indol-5-yl)-5-hydroxy-[1,2,4]triazole, 3-(2,4-dihydroxy-5-isopropyl-phenyl)-4-(1-methyl-indol-5-yl)-5-hydroxy-[1,2,4]triazole, 3-(2,4-dihydroxy-5-isopropyl-phenyl)-4-(1-isopropyl-indol-4-yl)-5-hydroxy-[1,2,4]triazole, and tautomers, pharmaceutically acceptable salts, solvates, clathrates, and prodrugs thereof.

In another embodiment, Z is —SH.

In another embodiment, the compound is selected from the group consisting of:

3-(2,4-dihydroxy-5-isopropyl-phenyl)-4-(1-methyl-indazol-5-yl)-5-mercapto-[1,2,4]triazole, 3-(2,4-dihydroxy-5-isopropyl-phenyl)-4-(1-methyl-indazol-6-yl)-5-mercapto-[1,2,4]triazole, and tautomers, pharmaceutically acceptable salts, solvates, clathrates, and prodrugs thereof.

Compounds of formula (VI) inhibit the activity of Hsp90 and are particularly useful for treating or preventing (e.g., reducing the likelihood of developing) angiogenesis related disorders, such as macular degeneration. In addition, compounds of formula (VI) are particularly useful in reducing, blocking, occluding, or otherwise disrupting blood flow in neovasculature.

In another aspect, the invention provides compounds represented by formula (VII):

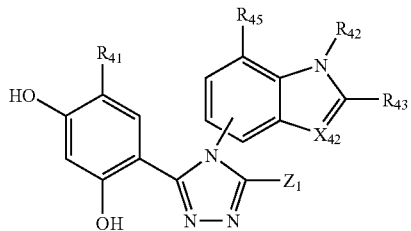

and tautomers, pharmaceutically acceptable salts, solvates, clathrates, and prodrugs thereof, wherein:

$Z_1$ is —OH or —SH;

$X_{42}$, $R_{41}$, $R_{42}$, $R_{43}$, and $R_{45}$ are defined as above.

In one embodiment, in formula (VII), $Z_1$ is —OH.

In another embodiment, in formula (VII), $Z_1$ is —SH.

In another embodiment, in formula (VII), $R_{41}$ is selected from the group consisting of —H, lower alkyl, lower alkoxy, lower cycloalkyl, and lower cycloalkoxy.

In another embodiment, in formula (VII), $R_{41}$ is selected from the group consisting of —H, methyl, ethyl, propyl, isopropyl, cyclopropyl, methoxy, ethoxy, propoxy, and cyclopropoxy.

In another embodiment, in formula (VII), $R_{42}$ is selected from the group consisting of lower alkyl, lower cycloalkyl, —C(O)N($R_{27}$)$_2$, or —C(O)OH, wherein $R_{27}$ is —H or a lower alkyl.

In another embodiment, in formula (VII), $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment, $R_{43}$ is H or a lower alkyl.

In another embodiment, in formula (VII), $X_{42}$ is C$R_{44}$, and $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment, in formula (VII), $X_{42}$ is C$R_{44}$, and $R_{43}$ and $R_{44}$, taken together with the carbon atoms to which they are attached, form a cycloalkenyl, aryl, heterocyclyl, or heteroaryl ring. Preferably, in this embodiment, $R_{43}$ and $R_{44}$, taken together with the carbon atoms to which they are attached, form a $C_5$-$C_8$ cycloalkenyl or a $C_5$-$C_8$ aryl.

In another embodiment, in formula (VII), $R_{45}$ is selected from the group consisting of —H, —OH, —SH, —NH$_2$, a lower alkoxy, a lower alkyl amino, and a lower dialkyl amino.

In another embodiment, in formula (VII), $R_{45}$ is selected from the group consisting of —H, —OH, methoxy, and ethoxy.

In another embodiment, in formula (VII), $X_{43}$ is C$R_{44}$.

In another embodiment, the compound is selected from the group consisting of:

3-(2,4-dihydroxyphenyl)-4-(1-ethyl-indol-4-yl)-5-mercapto-[1,2,4]triazole, 3-(2,4-dihydroxyphenyl)-4-(1-isopropyl-indol-4-yl)-5-mercapto-[1,2,4]triazole, 3-(2,4-dihydroxyphenyl)-4-(indol-4-yl)-5-mercapto-[1,2,4]triazole, 3-(2,4-dihydroxyphenyl)-4-(1-methoxyethyl-indol-4-yl)-5-mercapto-[1,2,4]triazole, 3-(2,4-dihydroxy-5-ethyl-phenyl)-4-(1-isopropyl-indol-4-yl)-5-mercapto-[1,2,4]triazole, 3-(2,4-dihydroxyphenyl)-4-(1-dimethylcarbamoyl-indol-4-yl)-5-mercapto-[1,2,4]triazole, 3-(2,4-dihydroxy-5-ethyl-phenyl)-4-(1-propyl-indol-4-yl)-5-mercapto-[1,2,4]triazole, 3-(2,4-dihydroxy-5-ethyl-phenyl)-4-(1,2,3-trimethyl-indol-5-yl)-5-mercapto-[1,2,4]triazole, 3-(2,4-dihydroxy-5-ethyl-phenyl)-4-(2,3-dimethyl-indol-5-yl)-5-mercapto-[1,2,4]triazole, 3-(2,4-dihydroxy-5-ethyl-phenyl)-4-(1-acetyl-2,3-dimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole, 3-(2,4-dihydroxy-5-ethyl-phenyl)-4-(1-propyl-2,3-dimethyl-indol-5-yl)-5-mercapto-[1,2,4]triazole, 3-(2,4-dihydroxy-5-ethyl-phenyl)-4-(N-methyl-tetrahydrocarbozol-7-yl)-5-mercapto-[1,2,4]triazole, 3-(2,4-dihydroxy-5-ethyl-phenyl)-4-(N-methyl-cyclononan[a]indol-5-yl)-5-mercapto-[1,2,4]triazole, 3-(2,4-dihydroxy-5-ethyl-phenyl)-4-(1-n-butyl-indol-4-yl)-5-mercapto-[1,2,4]triazole, 3-(2,4-dihydroxy-5-ethyl-phenyl)-4-(1-n-pentyl-indol-4-yl)-5-mercapto-[1,2,4]triazole, 3-(2,4-dihydroxy-5-ethyl-phenyl)-4-(1-n-hexyl-indol-4-yl)-5-mercapto-[1,2,4]triazole, 3-(2,4-dihydroxy-5-cyclopropyl-phenyl)-4-(1-(1-methylcyclopropyl)-indol-4-yl)-5-mercapto-[1,2,4]triazole, 3-(2,4-dihydroxy-5-cyclopropyl-phenyl)-4-(1-isopropyl-7-methoxy-indol-4-yl)-5-mercapto-[1,2,4]triazole, 3-(2,4-dihydroxy-5-cyclopropyl-phenyl)-4-(1,2,3-trimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole disodium salt, 3-(2,4-dihydroxy-5-tert-butyl-phenyl)-4-(1-isopropyl-7-methoxy-indol-4-yl)-5-mercapto-[1,2,4]triazole, 3-(2,4-dihydroxy-5-cyclopropyl-phenyl)-4-(1-propyl-7-methoxy-indol-4-yl)-5-mercapto-[1,2,4]triazole, 3-(2,4-dihydroxy-5-ethyl-phenyl)-4-(1-methyl-3-ethyl-indol-5-yl)-5-mercapto-[1,2,4]triazole, 3-(2,4-dihydroxy-5-ethyl-phenyl)-4-(1,3-dimethyl-indol-5-yl)-5-mercapto-[1,2,4]triazole, 3-(2,4-dihydroxy-5-isopropyl-phenyl)-4-(1-isopropyl-7-methoxy-indol-4-yl)-5-mercapto-[1,2,4]triazole, 3-(2,4-dihydroxy-5-ethyl-phenyl)-4-(1-methyl-3-isopropyl-indol-5-yl)-5-mercapto-[1,2,4]triazole, 3-(2,4-dihydroxy-5-ethyl-phenyl)-4-(N-ethyl-carbozol-7-yl)-5-mercapto-[1,2,4]triazole, 3-(2,4-dihydroxy-5-ethyl-phenyl)-4-(1-isopropyl-7-hydroxy-indol-4-yl)-5-mercapto-[1,2,4]triazole, 3-(2,4-dihydroxy-5-ethyl-phenyl)-4-(1-isopropyl-7-ethoxy-indol-4-yl)-5-mercapto-[1,2,4]triazole, 3-(2,4-dihydroxy-5-ethyl-phenyl)-4-(1,2-dimethyl-indol-5-yl)-5-mercapto-[1,2,4]triazole, 3-(2,4-dihydroxy-5-ethyl-phenyl)-4-(N-methyl-indol-5-yl)-5-mercapto-[1,2,4]triazole, 3-(2,4-dihydroxy-5-isopropyl-phenyl)-4-(1,3-dimethyl-indol-5-yl)-5-mercapto-[1,2,4]triazole, 3-(2,4-dihydroxy-5-cyclopropyl-phenyl)-4-(1,3-dimethyl-indol-5-yl)-5-mercapto-[1,2,4]triazole, 3-(2,4-dihydroxy-5-cyclopropyl-phenyl)-4-(1-methyl-indol-5-yl)-5-mercapto-[1,2,4]triazole, 3-(2,4-dihydroxy-5-isopropyl-phenyl)-4-(1H-indol-5-yl)-5-mercapto-[1,2,4]triazole, 3-(2,4-dihydroxy-5-ethyl-phenyl)-4-(1,2-dimethyl-indol-5-yl)-5-mercapto-[1,2,4]triazole, 3-(2,4-dihydroxy-5-isopropyl-phenyl)-4-(1-ethyl-indol-5-yl)-5-mercapto-[1,2,4]triazole, 3-(2,4-dihydroxy-5-isopropyl-phenyl)-4-(1-propyl-indol-5-yl)-5-mercapto-[1,2,4]triazole, and tautomers, pharmaceutically acceptable salts, solvates, clathrates, and prodrugs thereof.

In another embodiment, in formula (VII), $X_{42}$ is N.

In another embodiment, the compound is selected from the group consisting of 3-(2,4-dihydroxy-5-ethyl-phenyl)-4-(1-ethyl-benzimidazol-4-yl)-5-mercapto-[1,2,4]triazole, 3-(2,4-dihydroxy-5-ethyl-phenyl)-4-(1-ethyl-benzimidazol-4-yl)-5-mercapto-[1,2,4]triazole HCL salt, 3-(2,4-dihydroxy-5-ethyl-phenyl)-4-(2-methyl-3-ethyl-benzimidazol-5-yl)-5-mercapto-[1,2,4]triazole, 3-(2,4-dihydroxy-5-ethyl-phenyl)-4-(1-ethyl-2-methyl-benzimidazol-5-yl)-5-mercapto-[1,2,4]triazole, 3-(2,4-dihydroxy-5-isopropyl-phenyl)-4-(1-methyl-2-trifluoromethyl-benzimidazol-5-yl)-5-mercapto-[1,2,4]triazole, and tautomers, pharmaceutically acceptable salts, solvates, clathrates, and prodrugs thereof.

Compounds of formula (VII) inhibit the activity of Hsp90 and are particularly useful for treating or preventing (e.g., reducing the likelihood of developing) angiogenesis related disorders, such as macular degeneration. In addition, compounds of formula (VII) are particularly useful in reducing, blocking, occluding, or otherwise disrupting blood flow in neovasculature.

In another aspect, the invention provides compounds represented by formula (VIII):

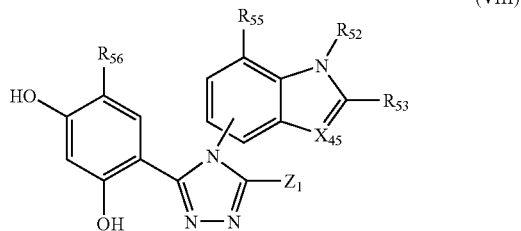

(VIII)

and tautomers, pharmaceutically acceptable salts, solvates, clathrates, and prodrugs thereof, wherein:

$X_{45}$ is $CR_{54}$ or N;

$Z_1$ is —OH or —SH;

$R_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;

$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring;

$R_{55}$ is selected from the group consisting of —H, —OH, —OCH$_3$, and —OCH$_2$CH$_3$; and $R_{56}$ is selected from the group consisting of —H, methyl, ethyl, isopropyl, and cyclopropyl.

In one embodiment, in formula (VIII), $Z_1$ is —OH.

In another embodiment, in formula (VIII), $Z_1$ is —SH.

In another embodiment, in formula (VIII), $R_{53}$ is H or a lower alkyl.

In another embodiment, in formula (VIII), $X_{45}$ is $CR_{54}$. Preferably, $R_{54}$ is H or a lower alkyl.

In another embodiment, $X_{45}$ is N.

In another embodiment, the compound is 3-(2,4-dihydroxy-5-isopropyl-phenyl)-4-(N-methyl-indol-5-yl)-5-mercapto-[1,2,4]triazole.

Compounds of formula (VIII) inhibit the activity of Hsp90 and are particularly useful for treating or preventing (e.g., reducing the likelihood of developing) angiogenesis related disorders, such as macular degeneration. In addition, compounds of formula (VIII) are particularly useful in reducing, blocking, occluding, or otherwise disrupting blood flow in neovasculature.

In another aspect, the invention provides compounds represented by formula (IX):

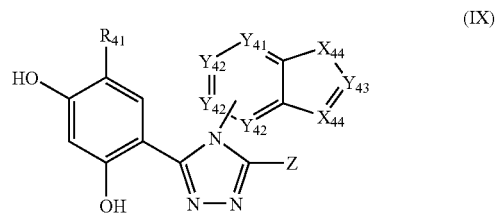

(IX)

and tautomers, pharmaceutically acceptable salts, solvates, clathrates, and prodrugs thereof, wherein, $X_{44}$, for each occurrence, is independently, O, $NR_{42}$ or $C(R_{46})_2$;

$Y_{43}$ is $NR_{42}$ or $C(R_{46})_2$;

$Y_{41}$, $Y_{42}$, Z, $R_{41}$, $R_{42}$, and $R_{46}$ are defined as above.

In one embodiment, in formula (IX), $R_{41}$ is selected from the group consisting of —H, lower alkyl, lower alkoxy, lower cycloalkyl, and lower cycloalkoxy.

In another embodiment, in formula (IX), $R_{41}$ is selected from the group consisting of —H, methyl, ethyl, propyl, isopropyl, cyclopropyl, methoxy, ethoxy, propoxy, and cyclopropoxy.

In another embodiment, in formula (IX), $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment, in formula (IX), $Y_{41}$ is $CR_{45}$. Preferably, $R_{45}$ is H, a lower alkoxy, or —OH.

In another embodiment, in formula (IX), $Y_{42}$ is CH.

In another embodiment, in formula (IX), $Y_{43}$ is CH$_2$.

In another embodiment, in formula (IX), $Y_{43}$ is $NR_{42}$, wherein $R_{42}$ is H or a lower alkyl.

In another embodiment, in formula (IX), one of $X_{44}$ is $NR_{42}$ and the other is CH$_2$ or $C(R_6)_2$. Preferably, one of $X_{44}$ is $NR_{42}$ and the other is CH$_2$.

In another embodiment, in formula (VI), Z is —OH.

In another embodiment, Z is —SH.

Compounds of formula (IX) inhibit the activity of Hsp90 and are particularly useful for treating or preventing (e.g., reducing the likelihood of developing) angiogenesis related disorders, such as macular degeneration. In addition, compounds of formula (IX) are particularly useful in reducing, blocking, occluding, or otherwise disrupting blood flow in neovasculature.

In another aspect, the invention provides compounds represented by formula (X):

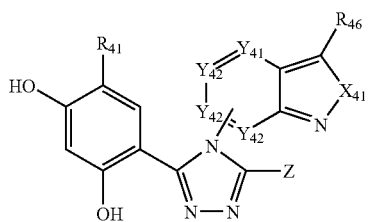

and tautomers, pharmaceutically acceptable salts, solvates, clathrates, and prodrugs thereof, wherein:

$X_{41}$, $Y_{41}$, $Y_{42}$, Z, $R_7$, $R_8$, $R_{10}$, $R_{11}$, $R_{41}$, $R_{46}$, and p are defined as above.

In one embodiment, in formula (X), $R_{41}$ is selected from the group consisting of —H, lower alkyl, lower alkoxy, lower cycloalkyl, and lower cycloalkoxy.

In another embodiment, in formula (X), $R_{41}$ is selected from the group consisting of —H, methyl, ethyl, propyl, isopropyl, cyclopropyl, methoxy, ethoxy, propoxy, and cyclopropoxy.

In another embodiment, in formula (X), $X_{41}$ is $NR_{42}$. Preferably, $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —$(CH_2)_m$C(O)OH, —$CH_2OCH_3$, —$CH_2CH_2OCH_3$, and —C(O)N$(CH_3)_2$. More preferably, $R_{42}$ is H or a lower alkyl.

In another embodiment, in formula (X), $X_{41}$ is O.
In another embodiment, in formula (X), $X_{41}$ is S.
In another embodiment, in formula (X), $Y_{41}$ is $CR_{45}$. Preferably, $R_{45}$ is H, a lower alkoxy, or —OH.
In another embodiment, in formula (X), $Y_{42}$ is CH.
In another embodiment, in formula (X), $R_{46}$ is H or a lower alkyl.

In one embodiment, the compound is 3-(2,4-dihydroxy-5-isopropyl-phenyl)-4-(2-methyl-indazol-6-yl)-5-mercapto-[1,2,4]triazole.

Compounds of formula (X) inhibit the activity of Hsp90 and are particularly useful for treating or preventing (e.g., reducing the likelihood of developing) angiogenesis related disorders, such as macular degeneration. In addition, compounds of formula (X) are particularly useful in reducing, blocking, occluding, or otherwise disrupting blood flow in neovasculature.

i) Exemplary Compounds of the Invention

Exemplary compounds of the invention are depicted in Table 1 below, including tautomers, pharmaceutically acceptable salts, solvates, clathrates, hydrates, polymorphs or prodrugs thereof.

TABLE 1

| No. | Structure | Tautomeric Structure | Name |
|---|---|---|---|
| 1 | 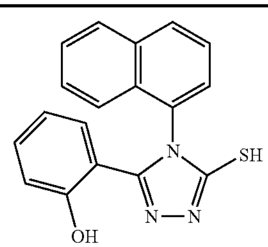 | | 3-(2-Hydroxyphenyl)-4-(naphthalen-1-yl)-5-mercapto-[1,2,4] triazole |
| 2 | 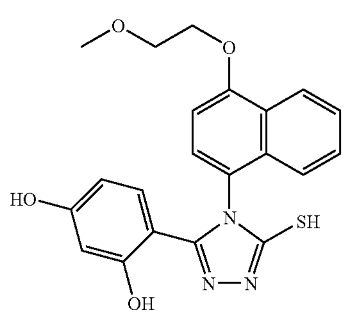 | | 3-(2,4-Dihydroxyphenyl)-4-[4-(2-methoxyethoxy)-naphthalen-1-yl]-5-mercapto-[1,2,4] triazole |
| 3 | 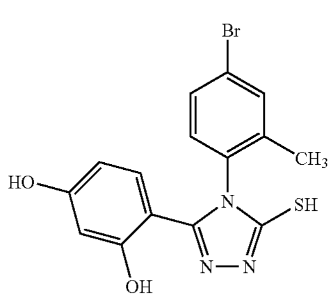 | | 3-(2,4-Dihydroxyphenyl)-4-(2-methyl-4-bromophenyl)-5-mercapto-[1,2,4] triazole |

TABLE 1-continued

| No. | Structure | Tautomeric Structure | Name |
|---|---|---|---|
| 4 | 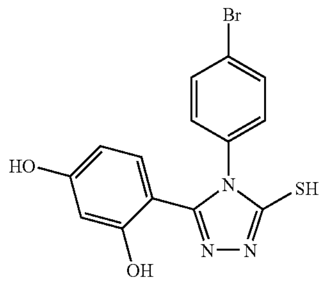 | | 3-(2,4-Dihydroxyphenyl)-4-(4-bromophenyl)-5-mercapto-[1,2,4]triazole |
| 5 | 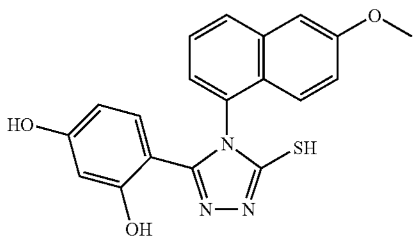 | | 3-(3,4-Dihydroxyphenyl)-4-(6-methoxy-naphthalen-1-yl)-5-mercapto-[1,2,4]triazole |
| 6 | 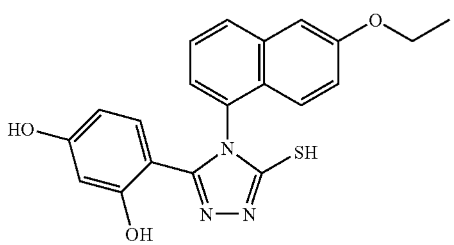 | | 3-(3,4-Dihydroxyphenyl)-4-(6-ethoxy-naphthalen-1-yl)-5-mercapto-[1,2,4]triazole |
| 7 | 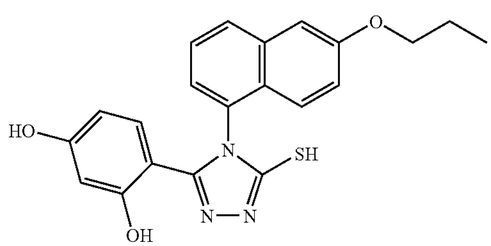 | | 3-(3,4-Dihydroxyphenyl)-4-(6-propoxy-naphthalen-1-yl)-5-mercapto-[1,2,4]triazole |
| 8 | 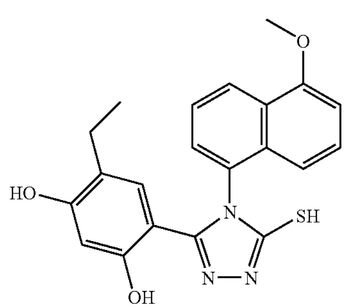 | | 3-(2,4-Dihydroxy-5-ethyl-phenyl)-4-(5-methoxy-naphthalen-1-yl)-5-mercapto-[1,2,4]triazole |
| 9 | 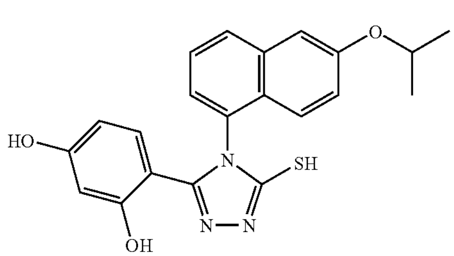 | | 3-(3,4-Dihydroxyphenyl)-4-(6-isopropoxy-naphthalen-1-yl)-5-mercapto-[1,2,4]triazole |

TABLE 1-continued

| No. | Structure | Tautomeric Structure | Name |
|---|---|---|---|
| 10 | 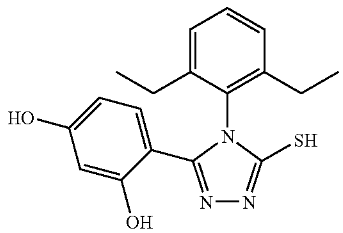 | | 3-(2,4-Dihydroxyphenyl)-4-(2,6-diethylphenyl)-5-mercapto-[1,2,4]triazole |
| 11 | 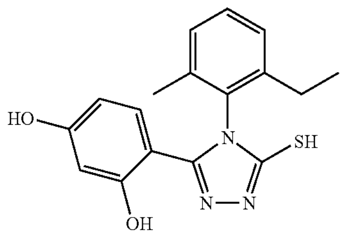 | | 3-(2,4-Dihydroxyphenyl)-4-(2-methyl-6-ethylphenyl)-5-mercapto-[1,2,4]triazole |
| 12 | 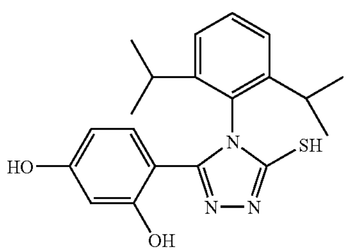 | | 3-(2,4-Dihydroxyphenyl)-4-(2,6-diisopropylphenyl)-5-mercapto-[1,2,4]triazole |
| 13 | 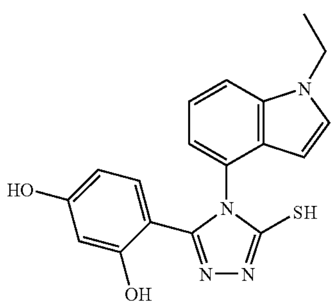 | | 3-(2,4-Dihydroxyphenyl)-4-(1-ethyl-indol-4-yl)-5-mercapto-[1,2,4]triazole |
| 14 | 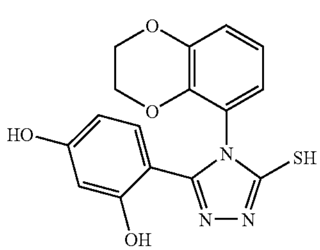 | | 3-(2,4-Dihydroxyphenyl)-4-(2,3-dihydro-benzo[1,4]dioxin-5-yl)-5-mercapto-[1,2,4]triazole |
| 15 | 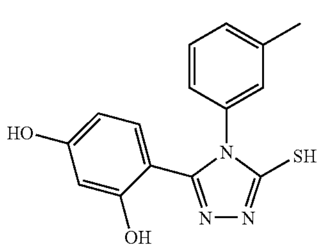 | | 3-(2,4-Dihydroxyphenyl)-4-(3-methylphenyl)-5-mercapto-[1,2,4]triazole |

TABLE 1-continued

| No. | Structure | Tautomeric Structure | Name |
|---|---|---|---|
| 16 | 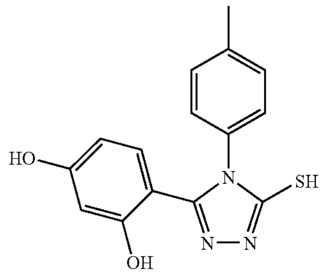 | | 3-(2,4-Dihydroxyphenyl)-4-(4-methylphenyl)-5-mercapto-[1,2,4]triazole |
| 17 | 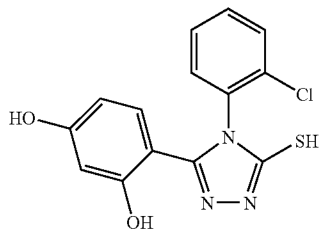 | | 3-(2,4-Dihydroxyphenyl)-4-(2-chlorophenyl)-5-mercapto-[1,2,4]triazole |
| 18 | 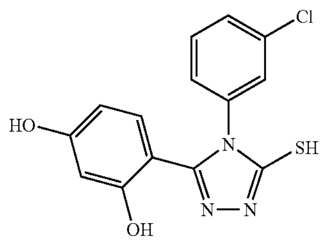 | | 3-(2,4-Dihydroxyphenyl)-4-(3-chlorophenyl)-5-mercapto-[1,2,4]triazole |
| 19 | 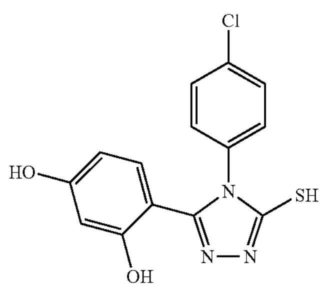 | | 3-(2,4-Dihydroxyphenyl)-4-(4-chlorophenyl)-5-mercapto-[1,2,4]triazole |
| 20 | 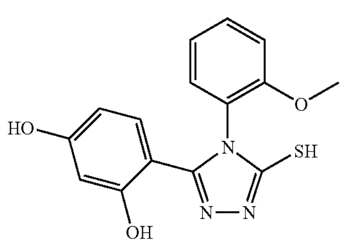 | | 3-(2,4-Dihydroxyphenyl)-4-(2-methoxyphenyl)-5-mercapto-[1,2,4]triazole |
| 21 | 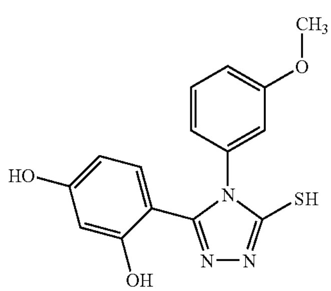 | | 3-(2,4-Dihydroxyphenyl)-4-(3-methoxyphenyl)-5-mercapto-[1,2,4]triazole |

TABLE 1-continued

| No. | Structure | Tautomeric Structure | Name |
|---|---|---|---|
| 22 | 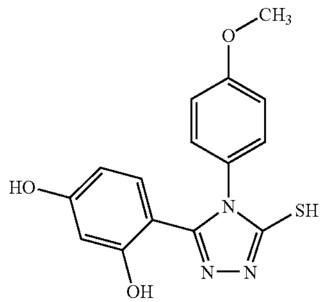 | | 3-(2,4-Dihydroxyphenyl)-4-(4-methoxyphenyl)-5-mercapto-[1,2,4] triazole |
| 23 | 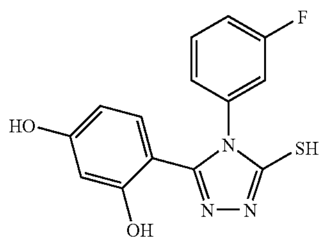 | | 3-(2,4-Dihydroxyphenyl)-4-(3-fluorophenyl)-5-mercapto-[1,2,4] triazole |
| 24 | 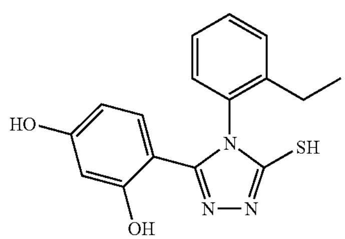 | | 3-(2,4-Dihydroxyphenyl)-4-(2-ethylphenyl)-5-mercapto-[1,2,4] triazole |
| 25 | 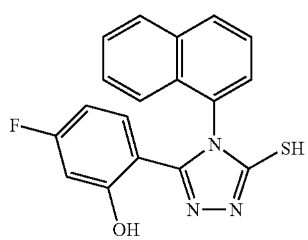 | | 3-(2-Hydroxy-4-fluorophenyl)-4-(naphthalen-1-yl)-5-mercapto-[1,2,4] triazole |
| 26 | 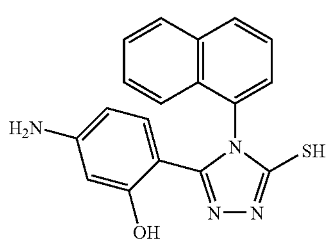 | | 3-(2-Hydroxy-4-aminophenyl)-4-(naphthalen-1-yl)-5-mercapto-[1,2,4] triazole |
| 27 | 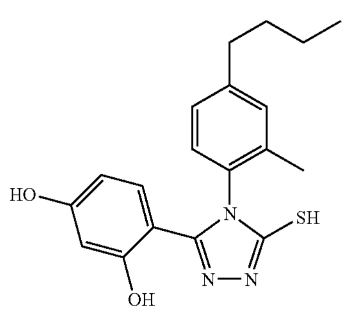 | | 3-(2,4-Dihydroxyphenyl)-4-(2-methyl-4-butyl-phenyl)-5-mercapto-[1,2,4] triazole |

TABLE 1-continued

| No. | Structure | Tautomeric Structure | Name |
|---|---|---|---|
| 28 | 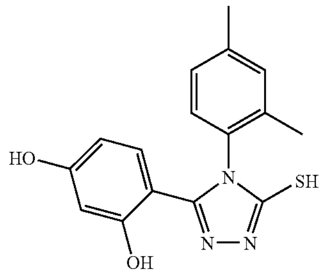 | | 3-(2,4-Dihydroxyphenyl)-4-(2,4-dimethylphenyl)-5-mercapto-[1,2,4]triazole |
| 29 | 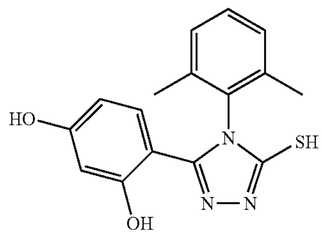 | | 3-(2,4-Dihydroxyphenyl)-4-(2,6-dimethylphenyl)-5-mercapto-[1,2,4]triazole |
| 30 | 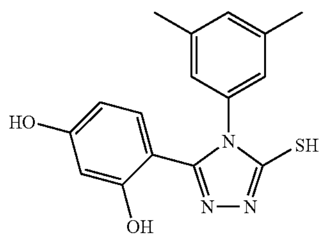 | | 3-(2,4-Dihydroxyphenyl)-4-(2,6-dimethylphenyl)-5-mercapto-[1,2,4]triazole |
| 31 | 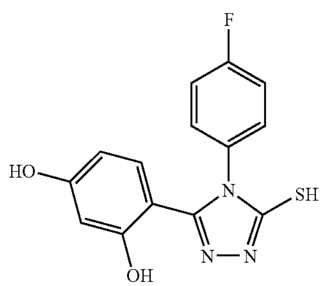 | | 3-(2,4-Dihydroxyphenyl)-4-(4-fluorophenyl)-5-mercapto-[1,2,4]triazole |
| 32 | 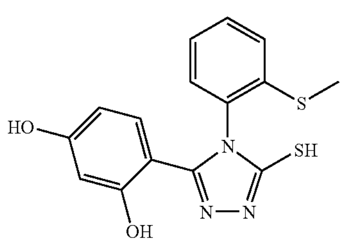 | | 3-(2,4-Dihydroxyphenyl)-4-(2-methylsulfanylphenyl)-5-mercapto-[1,2,4]triazole |
| 33 | 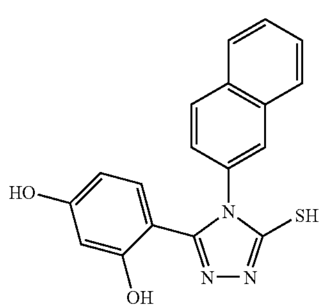 | | 3-(2,4-Dihydroxyphenyl)-4-(naphthalene-2-yl)-5-mercapto-[1,2,4]triazole |

TABLE 1-continued

| No. | Structure | Tautomeric Structure | Name |
|---|---|---|---|
| 34 | 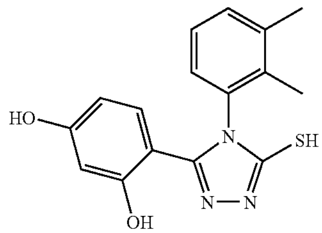 | | 3-(2,4-Dihydroxyphenyl)-4-(2,3-dimethylphenyl)-5-mercapto-[1,2,4] triazole |
| 35 | 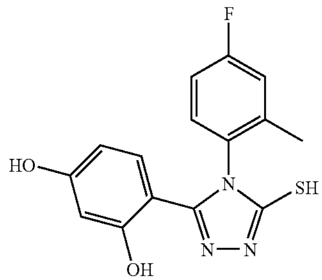 | | 3-(2,4-Dihydroxyphenyl)-4-(2-methyl-4-fluorophenyl)-5-mercapto-[1,2,4] triazole |
| 36 | 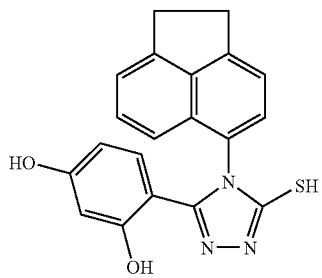 | | 3-(2,4-Dihydroxyphenyl)-4-(acenaphthalen-5-yl)-5-mercapto-[1,2,4] triazole |
| 37 | 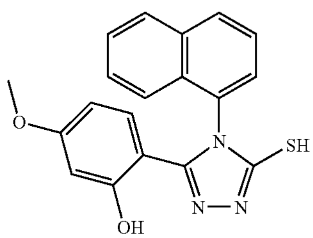 | | 3-(2-Hydroxy-4-methoxy-phenyl)-4-(naphthalen-1-yl)-5-mercapto-[1,2,4] triazole |
| 38 | 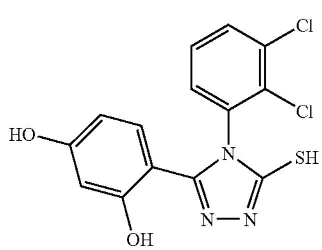 | | 3-(2,4-Dihydroxyphenyl)-4-(2,3-dichlorophenyl)-5-mercapto-[1,2,4] triazole |
| 39 | 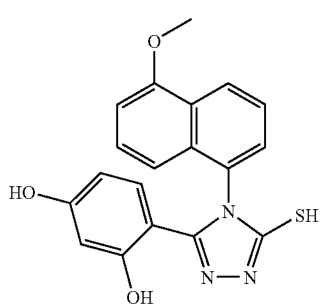 | | 3-(2,4-Dihydroxyphenyl)-4-(5-methoxynaphthalen-1-yl)-5-mercapto-[1,2,4] triazole |

TABLE 1-continued

| No. | Structure | Tautomeric Structure | Name |
|---|---|---|---|
| 40 | 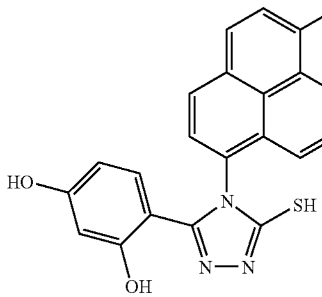 | | 3-(2,4-Dihydroxyphenyl)-4-(pyren-1-yl)-5-mercapto-[1,2,4]triazole |
| 41 | 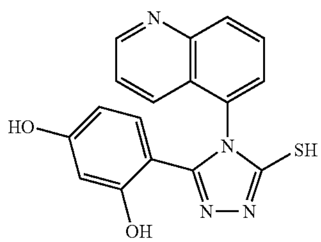 | | 3-(2,4-Dihydroxyphenyl)-4-(quinolin-5-yl)-5-mercapto-[1,2,4]triazole |
| 42 | 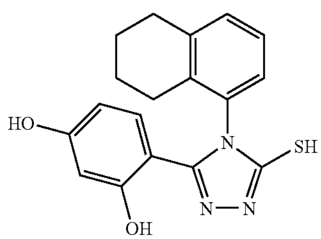 | | 3-(2,4-Dihydroxyphenyl)-4-(1,2,3,4-tetrahydronaphthalen-5-yl)-5-mercapto-[1,2,4]triazole |
| 43 | 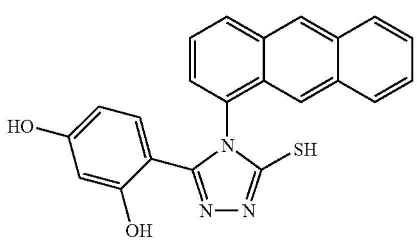 | | 3-(2,4-Dihydroxyphenyl)-4-(anthracen-1-yl)-5-mercapto-[1,2,4]triazole |
| 44 | 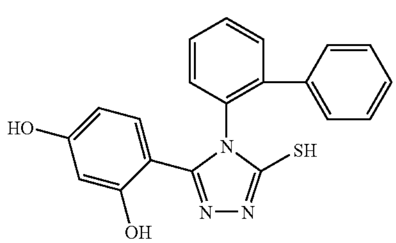 | | 3-(2,4-Dihydroxyphenyl)-4-(biphenyl-2-yl)-5-mercapto-[1,2,4]triazole |
| 45 | 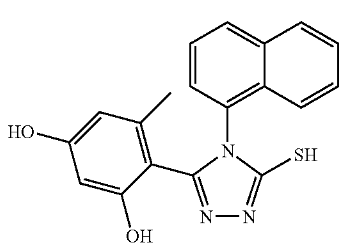 | | 3-(2,4-Dihydroxy-6-methyl-phenyl)-4-(naphthalene-1-yl)-5-mercapto-[1,2,4]triazole |

US 8,188,075 B2

TABLE 1-continued

| No. | Structure | Tautomeric Structure | Name |
|---|---|---|---|
| 46 | 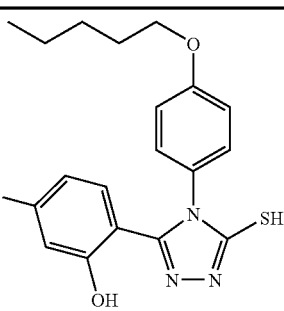 | 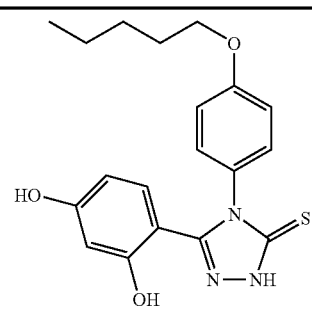 | 3-(2,4-Dihydroxyphenyl)-4-(4-pentyloxyphenyl)-5-mercapto-[1,2,4]triazole |
| 47 | 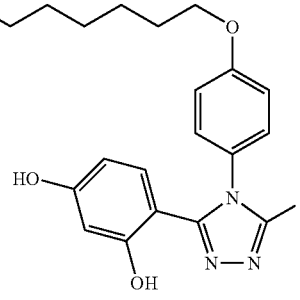 | 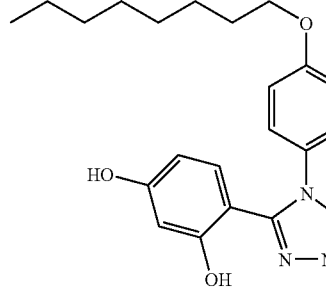 | 3-(2,4-Dihydroxyphenyl)-4-(4-octyloxyphenyl)-5-mercapto-[1,2,4]triazole |
| 48 | 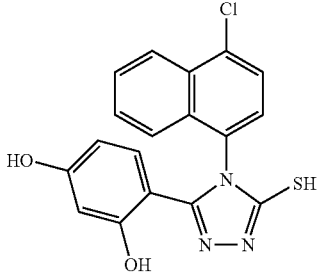 | 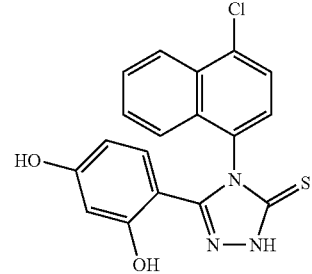 | 3-(2,4-Dihydroxyphenyl)-4-(4-chloronaphthalen-1-yl)-5-mercapto-[1,2,4]triazole |
| 49 | 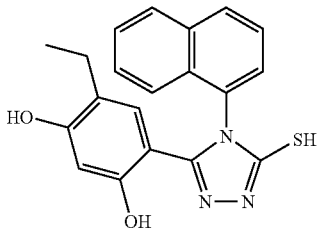 | 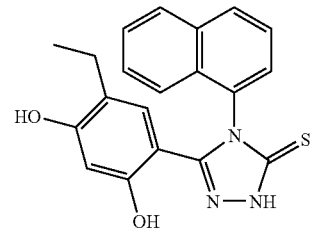 | 3-(2,4-Dihydroxy-5-ethyl-phenyl)-4-(naphthalen-1-yl)-5-mercapto-[1,2,4]triazole |
| 50 | 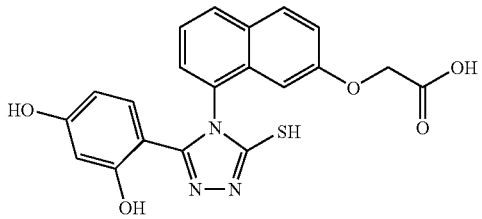 | 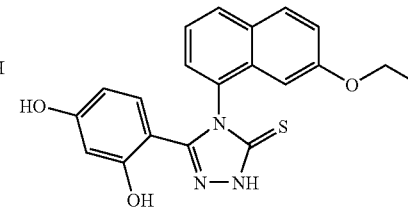 | 3-(2,4-Dihydroxy-5-ethyl-phenyl)-4-(7-carboxymethoxy-naphthalen-1-yl)-5-mercapto-[1,2,4]triazole |
| 51 | 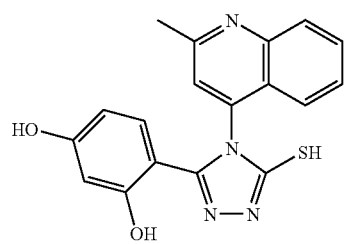 | 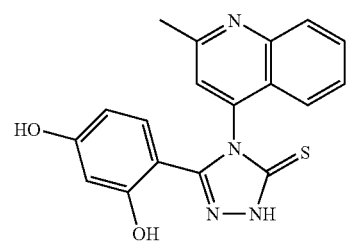 | 3-(2,4-Dihydroxyphenyl)-4-(2-methyl-quinolin-4-yl)-5-mercapto-[1,2,4]triazole |

TABLE 1-continued

| No. | Name |
|---|---|
| 52 | 3-(3-Hydroxypyridin-4-yl)-4-(naphthalen-1-yl)-5-mercapto-[1,2,4]triazole |
| 53 | 3-(2-Hydroxy-4-acetylamino-phenyl)-4-(naphthalen-1-yl)-5-mercapto-[1,2,4]triazole |
| 54 | 3-(2,4-Dihydroxy-phenyl)-4-(1,2,3,4-tetrahydronaphthalen-1-yl)-5-mercapto-[1,2,4]triazole |
| 55 | 3-(2,4-Dihydroxy-phenyl)-4-(2,3-dihydro-benzo[1,4]dioxin-5-yl)-5-mercapto-[1,2,4]triazole |
| 56 | 3-(2,4-Dihydroxy-phenyl)-4-(3,5-dimethoxyphenyl)-5-mercapto-[1,2,4]triazole |
| 57 | 3-(2,4-Dihydroxy-phenyl)-4-(2,3-dimethyl-1H-indol-4-yl)-5-mercapto-[1,2,4]triazole |

TABLE 1-continued

| No. | Name |
|---|---|
| 58 | 3-(2,4-Dihydroxy-3-propyl-phenyl)-4-(naphthalen-1-yl)-5-mercapto-[1,2,4] triazole |
| 59 | 3-(1-ethyl-5-hydroxy-6-oxo-1,6-dihydro-pyridin-3-yl)-4-(naphthalen-1-yl)-5-mercapto-[1,2,4] triazole |
| 60 | 3-(4-hydroxy-6-oxopyridin-3-yl)-4-(naphthalen-1-yl)-5-mercapto-[1,2,4] triazole |
| 61 | 3-(2,4-Dihydroxy-phenyl)-4-(3,5-di-tert-butylphenyl)-5-mercapto-[1,2,4] triazole |
| 62 | 3-(2,6-Dihydroxy5-fluoro-pyridin-3-yl) 4-(naphthalen-1-yl)-5-mercapto-[1,2,4] triazole |
| 63 | 3-(2,4-Dihydroxy-5-methyl-phenyl)-4-(naphthalene-1-yl)-5-mercapto-[1,2,4] triazole |

TABLE 1-continued

| No. | Structure | Tautomeric Structure | Name |
|---|---|---|---|
| 64 | 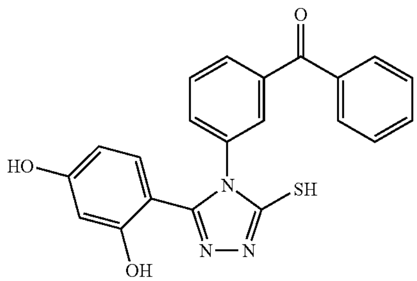 | | 3-[2,4-Dihydroxyphenyl]-4-(3-benzophenyl)-5-mercapto-[1,2,4]triazole |
| 65 | 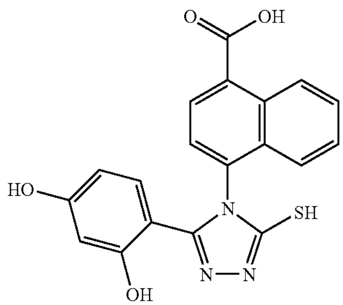 | | 3-(2,4-Dihydroxyphenyl)-4-(4-carboxy-naphthalen-1-yl)-5-mercapto-[1,2,4]triazole |
| 66 | 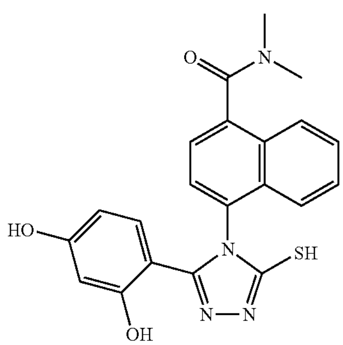 | | 3-(2,4-Dihydroxyphenyl)-4-[4-(N,N-dimethylcarbamoyl)-naphthalen-1-yl]-5-mercapto-[1,2,4]triazole |
| 67 | 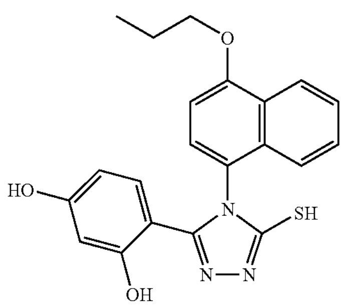 | | 3-(2,4-Dihydroxyphenyl)-4-(4-propoxy-naphthalen-1-yl)-5-mercapto-[1,2,4]triazole |
| 68 | 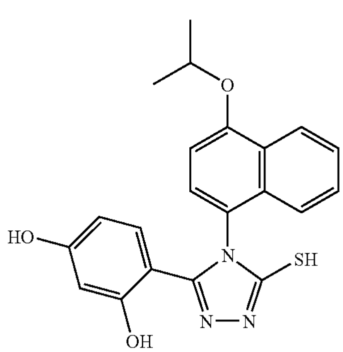 | | 3-(2,4-Dihydroxyphenyl)-4-(4-isopropoxy-naphthalen-1-yl)-5-mercapto-[1,2,4]triazole |

TABLE 1-continued

| No. | Structure | Tautomeric Structure | Name |
|---|---|---|---|
| 69 | 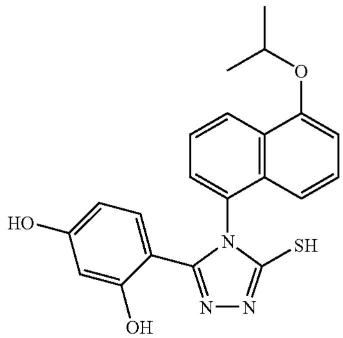 | | 3-(2,4-Dihydroxy-phenyl)-4-(5-isopropoxy-naphthalen-1-yl)-5-mercapto-[1,2,4] triazole |
| 70 | 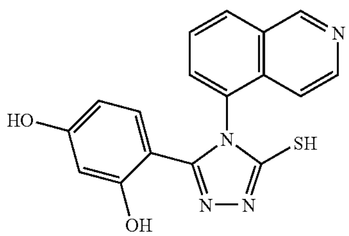 | | 3-(2,4-Dihydroxy-phenyl)-4-(isoquinolin-5-yl)-5-mercapto-[1,2,4] triazole |
| 71 | 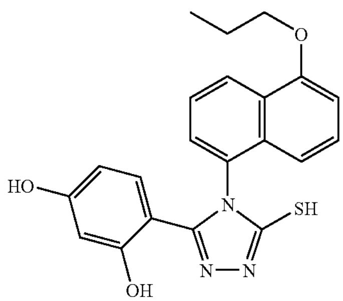 | | 3-(2,4-Dihydroxy-phenyl)-4-(5-propoxy-naphthalen-1-yl)-5-mercapto-[1,2,4] triazole |
| 72 | 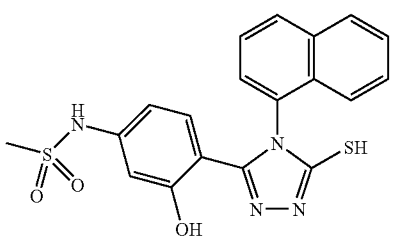 | | 3-(2-Hydroxy-4-methanesulfonamino-phenyl)-4-(naphthalen-1-yl)-5-mercapto-[1,2,4] triazole |
| 73 | 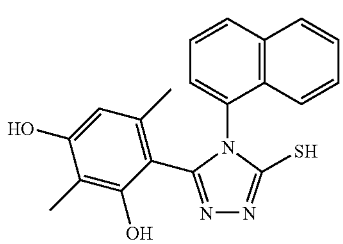 | | 3-(2,4-Dihydroxy-3,6-dimethyl-phenyl)-4-(naphthalen-1-yl)-5-mercapto-[1,2,4] triazole |
| 74 | 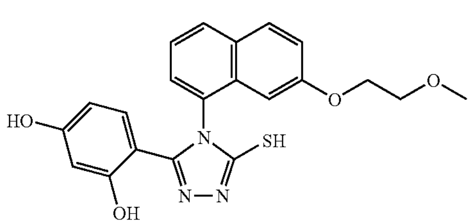 | | 3-(2,4-Dihydroxy-phenyl)-4-[7-(2-methoxyethoxy)-naphthalen-1-yl]-5-mercapto-[1,2,4] triazole |

TABLE 1-continued

| No. | Structure | Tautomeric Structure | Name |
|---|---|---|---|
| 75 | 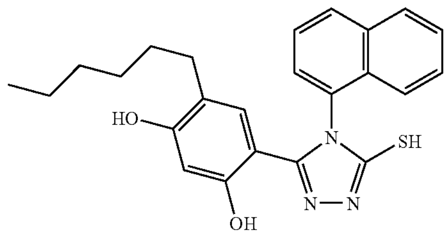 | | 3-(2,4-Dihydroxy-5-hexyl-phenyl)-4-(naphthalen-1-yl)-5-mercapto-[1,2,4]triazole |
| 76 | 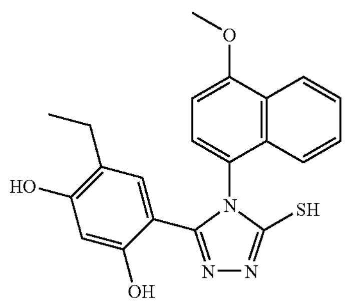 | | 3-(2,4-Dihydroxy-5-ethyl-phenyl)-4-(4-methoxy-naphthalen-1-yl)-5-mercapto-[1,2,4]triazole |
| 77 | 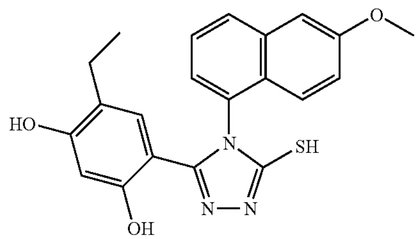 | | 3-(2,4-Dihydroxy-5-ethyl-phenyl)-4-(6-methoxy-naphthalin-1-yl)-5-mercapto-[1,2,4]triazole |
| 78 | 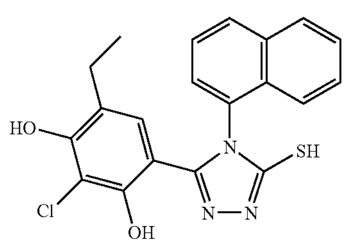 | | 3-(2,4-Dihydroxy-3-chloro-5-ethyl-phenyl)-4-(naphthalen-1-yl)-5-mercapto-[1,2,4]triazole |
| 79 | 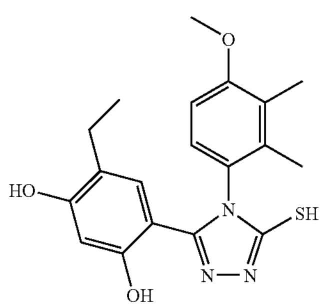 | | 3-(2,4-Dihydroxy-5-ethyl-phenyl)-4-(2,3-dimethy-4-methoxy-phenyl)-5-mercapto-[1,2,4]triazole |
| 80 | 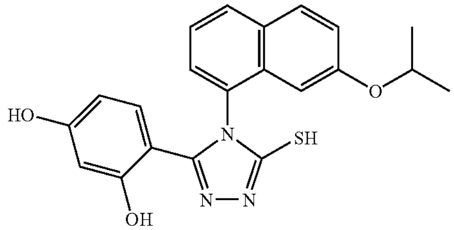 | | 3-(2,4-Dihydroxy-phenyl)-4-(7-isopropoxy-naphthalen-1-yl)-5-mercapto-[1,2,4]triazole |

TABLE 1-continued

| No. | Structure | Tautomeric Structure | Name |
|---|---|---|---|
| 81 | 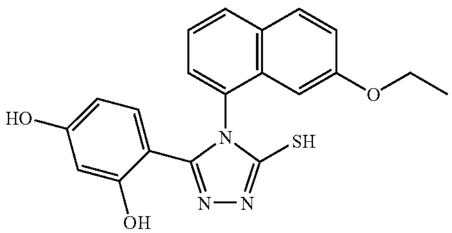 | | 3-(2,4-Dihydroxy-phenyl)-4-(7-ethoxy-naphthalen-1-yl)-5-mercapto-[1,2,4] triazole |
| 82 | 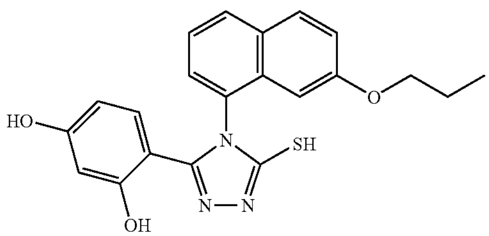 | | 3-(2,4-Dihydroxy-phenyl)-4-(7-propoxy-naphthalen-1-yl)-5-mercapto-[1,2,4] triazole |
| 83 | 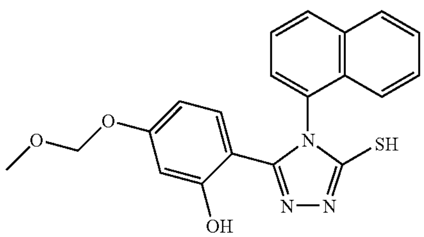 | | 3-(2-Hydroxy-4-methoxymethyoxy-phenyl)-4-(naphthalen-1-yl)-5-mercapto-[1,2,4] triazole |
| 84 | 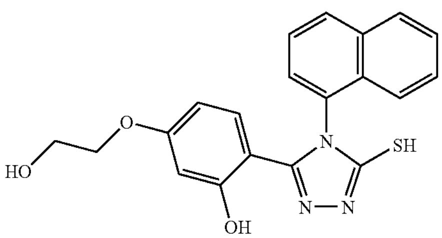 | | 3-[2-Hydroxy-4-(2-hydroxy-ethoxy)-phenyl]-4-(naphthalen-1-yl)-5-mercapto-[1,2,4] triazole |
| 85 | 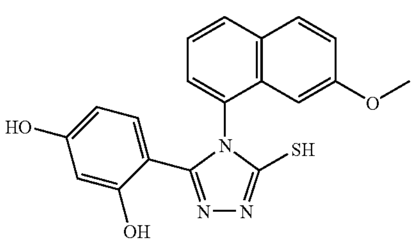 | | 3-(2,4-Dihydroxyphenyl)-4-(7-methoxy-naphthalen-1-yl)-5-mercapto-[1,2,4] triazole |
| 86 | 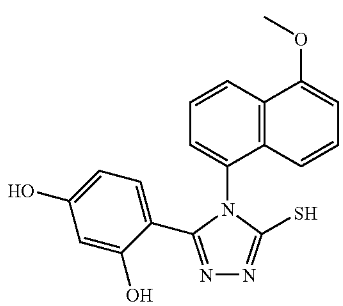 | | 3-(2,4-Dihydroxyphenyl)-4-(5-methoxy-naphthalen-1-yl)-5-mercapto-[1,2,4] triazole |

TABLE 1-continued

| No. | Structure | Tautomeric Structure | Name |
|---|---|---|---|
| 87 | 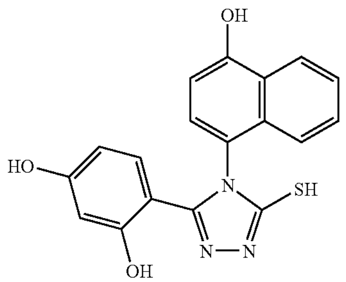 | | 3-(2,4-Dihydroxyphenyl)-4-(4-hydroxy-naphthalen-1-yl)-5-mercapto-[1,2,4]triazole |
| 88 | 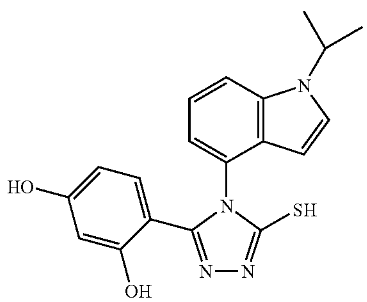 | | 3-(2,4-Dihydroxyphenyl)-4-(1-isopropyl-indol-4-yl)-5-mercapto-[1,2,4]triazole |
| 89 | 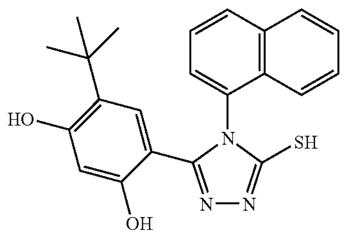 | | 3-(2,4-Dihydroxy-5-tert-butyl-phenyl)-4-(naphthalen-1-yl)-5-mercapto-[1,2,4]triazole |
| 90 | 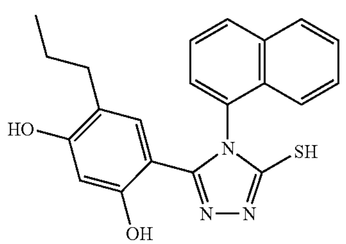 | | 3-(2,4-Dihydroxy-5-propyl-phenyl)-4-(naphthalen-1-yl)-5-mercapto-[1,2,4]triazole |
| 91 | 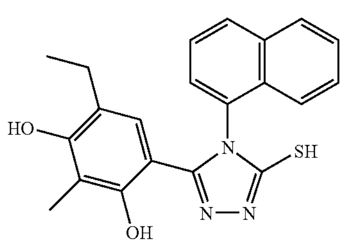 | | 3-(2,4-Dihydroxy-3-methyl-5-ethyl-phenyl)-4-(naphthalen-1-yl)-5-mercapto-[1,2,4]triazole |
| 92 | 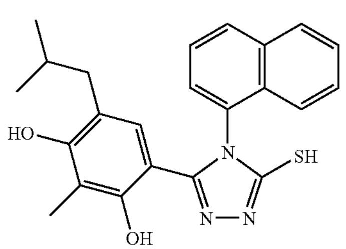 | | 3-(2,4-Dihydroxy-5-isobutyl-phenyl)-4-(naphthalen-1-yl)-5-mercapto-[1,2,4]triazole |

TABLE 1-continued

| No. | Structure | Tautomeric Structure | Name |
|---|---|---|---|
| 93 | 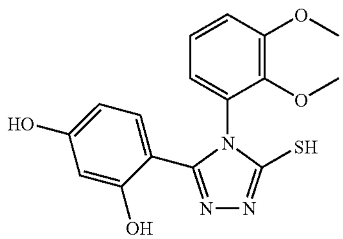 | | 3-(2,4-Dihydroxy-phenyl)-4-(2,3-dimethoxy-phenyl)-5-mercapto-[1,2,4] triazole |
| 94 | 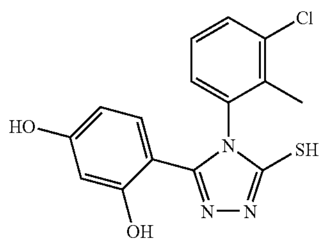 | | 3-(2,4-Dihydroxy-phenyl)-4-(2-methoxy-3-chloro-phenyl)-5-mercapto-[1,2,4] triazole |
| 95 | 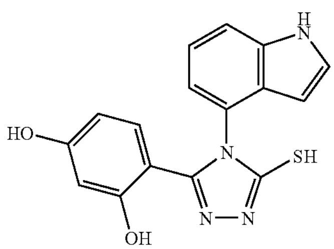 | | 3-(2,4-Dihydroxy-phenyl)-4-(indol-4-yl)-5-mercapto-[1,2,4] triazole |
| 96 | 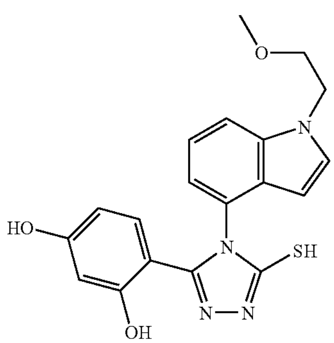 | | 3-(2,4-Dihydroxy-phenyl)-4-[1-(2-methoxyethoxy)-indol-4-yl]-5-mercapto-[1,2,4] triazole |
| 97 | 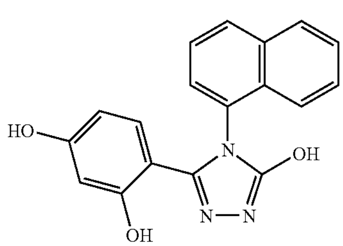 | | 3-(2,4-Dihydroxy-phenyl)-4-(naphthalen-1-yl)-5-hydroxy-[1,2,4] triazole |
| 98 | 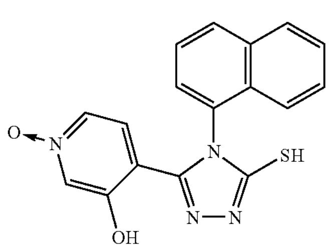 | | 3-(1-Oxo-3-hydroxy-pyridin-4-yl)-4-(naphthalen-1-yl)-5-mercapto-[1,2,4] triazole |

TABLE 1-continued

| No. | Structure | Tautomeric Structure | Name |
|---|---|---|---|
| 99 | 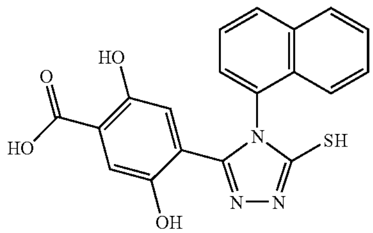 | | 3-(2,5-Dihydroxy-4-carboxy)-4-(naphthalen-1-yl)-5-mercapto-[1,2,4] triazole |
| 100 | 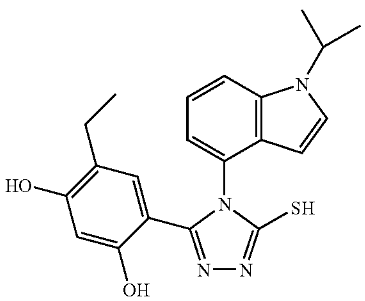 | | 3-(2,4-Dihydroxy-5-ethyl-phenyl)-4-(1-isopropyl-indol-4-yl)-5-mercapto-[1,2,4] triazole |
| 101 | 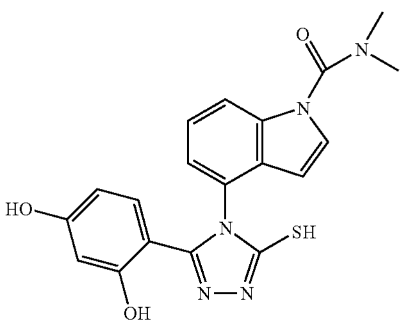 | | 3-(2,4-Dihydroxy-5-ethyl-phenyl)-4-[1-(dimethyl-carbamoyl)-indol-4-yl]-5-mercapto-[1,2,4] triazole |
| 102 | 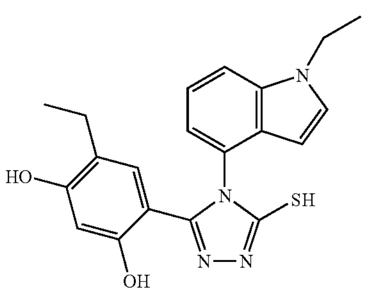 | | 3-(2,4-Dihydroxy-5-ethyl-phenyl)-4-(1-ethyl-benzoimidazol-4-yl)-5-mercapto-[1,2,4] triazole |
| 103 | 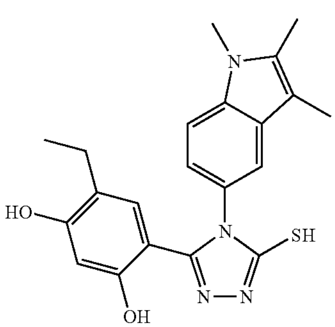 | | 3-(2,4-Dihydroxy-5-ethyl-phenyl)-4-(1,2,3-trimethyl-indol-5-yl)-5-mercapto-[1,2,4] triazole |

TABLE 1-continued

| No. | Structure | Tautomeric Structure | Name |
| --- | --- | --- | --- |
| 104 | 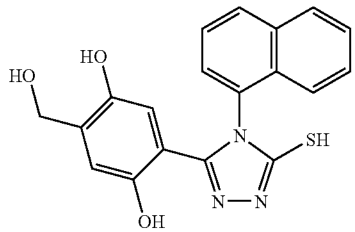 | | 3-(2,4-Dihydroxy-4-hydroxymethyl-phenyl)-4-(naphthalen-1-yl)-5-mercapto-[1,2,4]triazole |
| 105 | 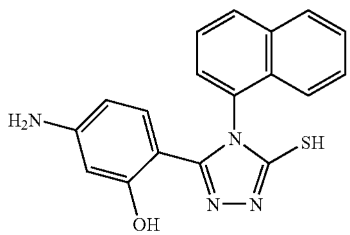 | | 3-(2-Hydroxy-4-amino-phenyl)-4-(naphthalen-1-yl)-5-mercapto-[1,2,4]triazole |
| 106 | 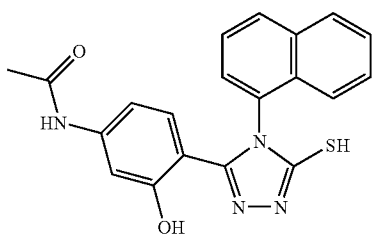 | | 3-(2-Hydroxy-4-acetylamino-phenyl)-4-(naphthalen-1-yl)-5-mercapto-[1,2,4]triazole |
| 107 | 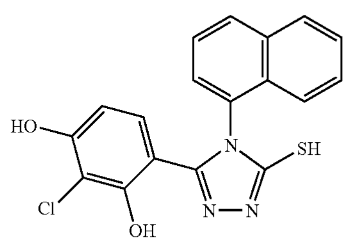 | | 3-(2,4-Dihydroxy-3-chloro-phenyl)-4-(naphthalen-1-yl)-5-mercapto-[1,2,4]triazole |
| 108 | 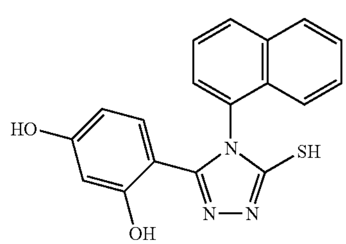 | | 3-(2,4-Dihydroxy-phenyl)-4-(naphthalen-1-yl)-5-mercapto-[1,2,4]triazole |
| 109 | 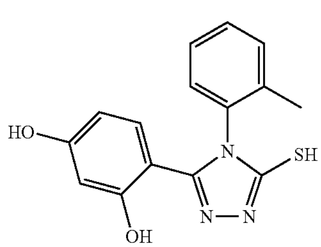 | | 3-(2,4-Dihydroxy-phenyl)-4-(2-methyl-phenyl)-5-mercapto-[1,2,4]triazole |

TABLE 1-continued

| No. | Structure | Tautomeric Structure | Name |
|---|---|---|---|
| 110 | 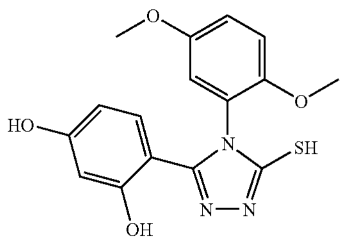 | | 3-(2,4-Dihydroxy-phenyl)-4-(2,5-dimethoxy-phenyl)-5-mercapto-[1,2,4] triazole |
| 111 | 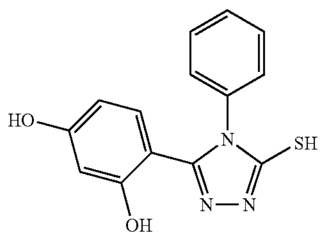 | | 3-(2,4-Dihydroxy-phenyl)-4-phenyl-5-mercapto-[1,2,4] triazole |
| 112 | 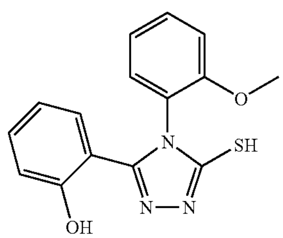 | | 3-(2-Hydroxy-phenyl)-4-(2-methoxy-phenyl)-5-mercapto-[1,2,4] triazole |
| 113 | 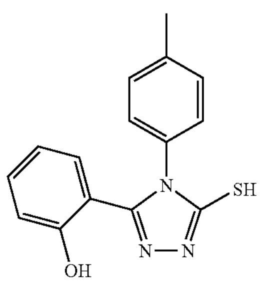 | | 3-(2-Hydroxy-phenyl)-4-(4-methyl-phenyl)-5-mercapto-[1,2,4] triazole |
| 114 | 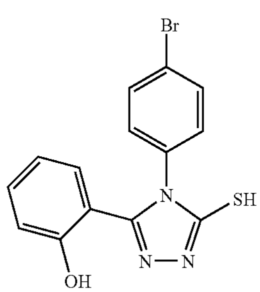 | | 3-(2-Hydroxy-phenyl)-4-(4-bromo-phenyl)-5-mercapto-[1,2,4] triazole |
| 115 | 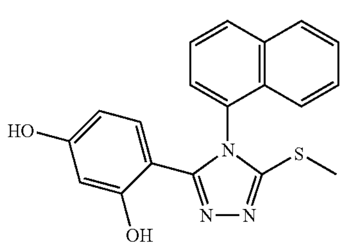 | | 3-(2,4-Dihydroxy-phenyl)-4-(naphthalen-1-yl)-5-(methyl sulfanyl)-[1,2,4] triazole |

TABLE 1-continued

| No. | Structure | Tautomeric Structure | Name |
|---|---|---|---|
| 116 | 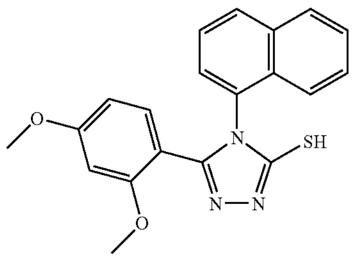 | | 3-(2,4-Dimethoxyphenyl)-4-(naphthalen-1-yl)-5-mercapto-[1,2,4]triazole |
| 117 | 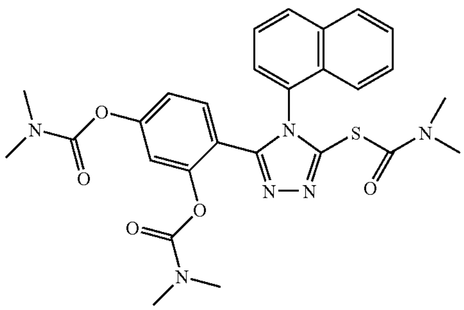 | | 3-[2,4-(dimethylcarbamoyloxy)-phenyl]-4-(naphthalen-1-yl)-5-(dimethylcarbamoylsulfanyl)-[1,2,4]triazole |
| 118 | 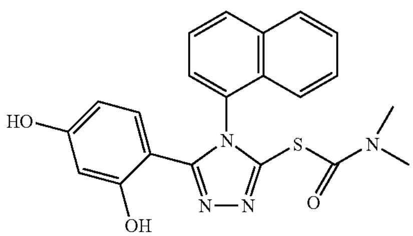 | | 3-(2,4-Dihydroxy-phenyl)-4-(naphthalen-1-yl)-5-(dimethylcarbamoyl-sulfanyl)-[1,2,4]triazole |
| 119 | 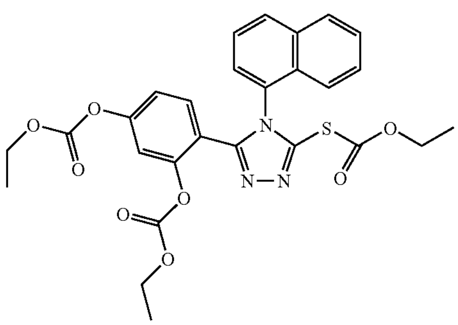 | | 3-(2,4-Diethoxycarbonyloxy-phenyl)-4-(naphthalen-1-yl)-5-(ethoxycarbonylsulfanyl)-[1,2,4]triazole |
| 120 | 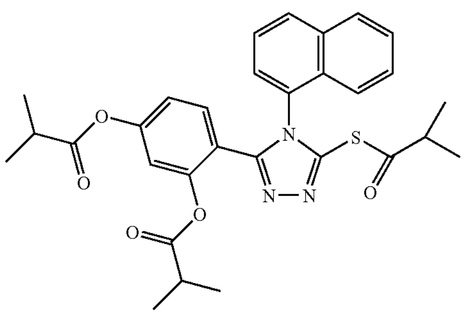 | | 3-(2,4-Di-isobutyryloxyl-phenyl)-4-(naphthalen-1-yl)-5-(isobutyrylsulfanyl)-[1,2,4]triazole |

TABLE 1-continued

| No. | Structure | Tautomeric Structure | Name |
|---|---|---|---|
| 121 | 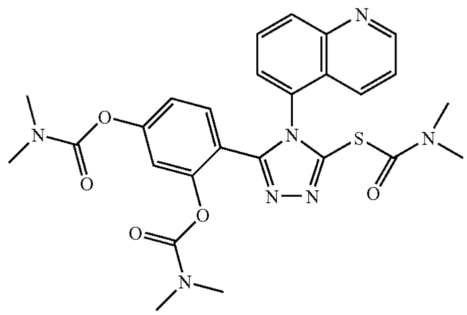 | | 3-[2,4-Di-(dimethyl-carbamoyloxy)-phenyl]-4-(quinolin-5-yl)-5-(dimethyl-carbamoylsulfanyl)-[1,2,4]triazole |
| 122 | 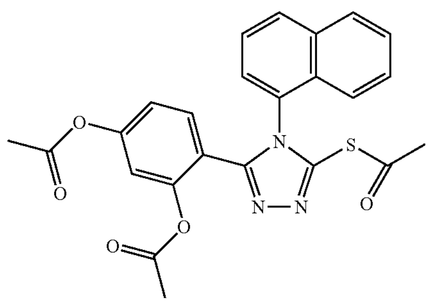 | | 3-[2,4-Diacetoxy-phenyl)-4-(naphthalen-1-yl)-5-(acetylsulfanyl)-[1,2,4]triazole |
| 123 | 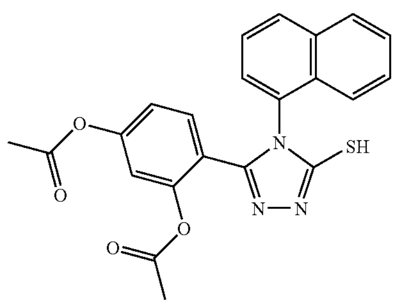 | | 3-(2,4-Diacetoxy-phenyl)-4-(naphthalen-1-yl)-5-mercapto-[1,2,4]triazole |
| 124 | 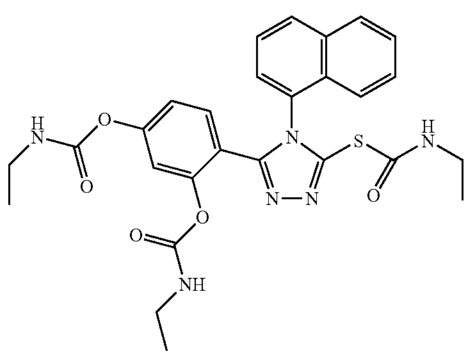 | | 3-(2,4-Diethylcarbamoyloxy-phenyl)-4-(naphthalen-1-yl)-5-(ethylcarbamoyl-sulfanyl)-[1,2,4]triazole |
| 125 | 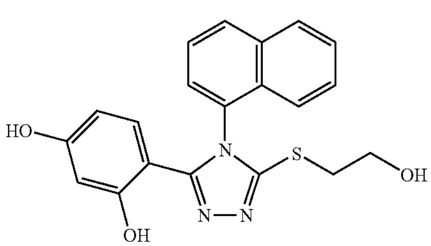 | | 3-(2,4-Dihydroxy-phenyl)-4-(naphthalen-1-yl)-5-(2-hydroxyethyl-sulfanyl)-[1,2,4]triazole |

TABLE 1-continued

| No. | Structure | Tautomeric Structure | Name |
|---|---|---|---|
| 126 | 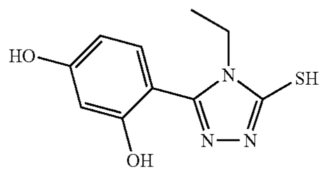 | | 3-(2,4-Dihydroxy-phenyl)-4-ethyl-5-mercapto-[1,2,4]triazole |
| 127 | 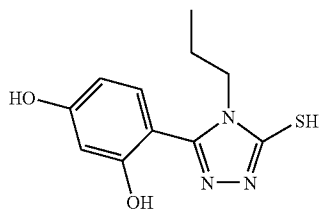 | | 3-(2,4-Dihydroxy-phenyl)-4-propyl-5-mercapto[1,2,4]triazole |
| 128 | 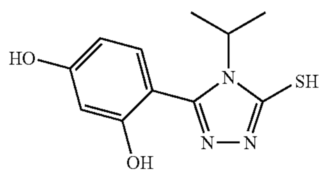 | | 3-(2,4-Dihydroxy-phenyl)-4-isopropyl-5-mercapto-[1,2,4]triazole |
| 129 | 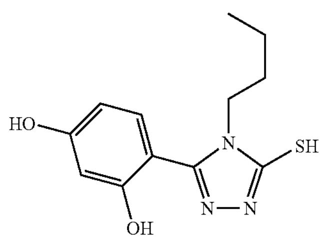 | | 3-(2,4-Dihydroxy-phenyl)-4-butyl-5-mercapto-[1,2,4]triazole |
| 130 | 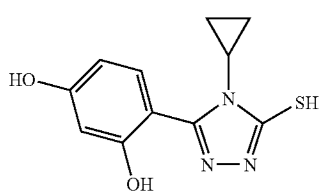 | | 3-(2,4-Dihydroxy-phenyl)-4-cyclopropyl-5-mercapto-[1,2,4]triazole |
| 131 | 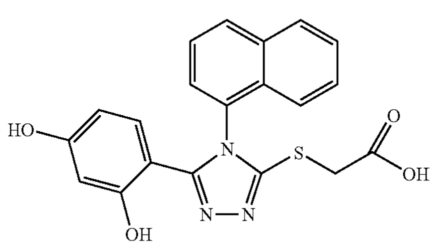 | | 3-(2,4-Dihydroxy-phenyl)-4-(naphthalen-1-yl)-5-(carboxyethysulfanyl-[1,2,4]triazole |
| 132 | 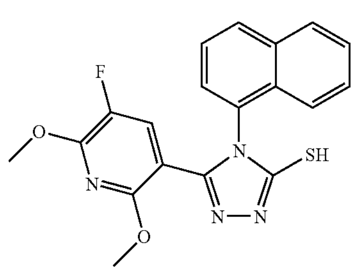 | | 3-(2,6-Dimethoxy-5-fluoro-pyridin-3-yl)-4-(naphthalen-1-yl)-5-mercapto-[1,2,4]triazole |

TABLE 1-continued
| No. | Structure | Tautomeric Structure | Name |
|---|---|---|---|
| 133 | 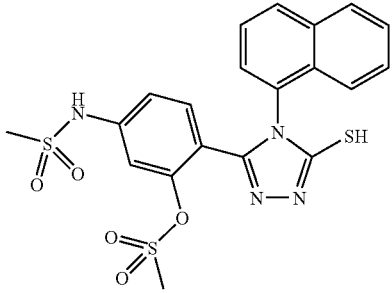 | 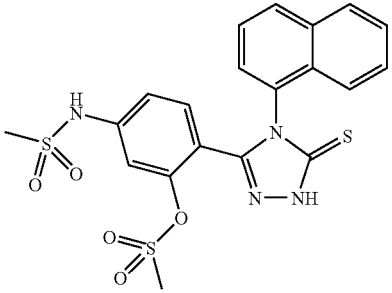 | 3-(2-Methanesulfonyloxy-4-methanesulfonyl-amino-phenyl)-4-(naphthalen-1-yl)-5-mercapto-[1,2,4]triazole |
| 134 | 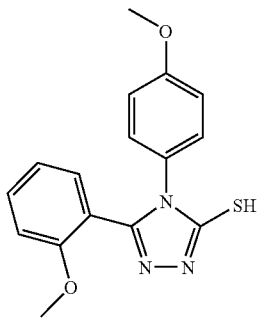 | 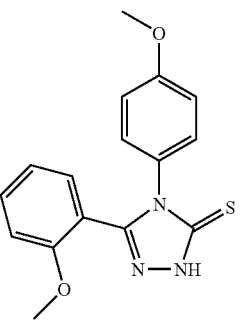 | 3-(2-Methoxy-phenyl)-4-(4-methoxy-phenyl)-5-mercapto-[1,2,4]triazole |
| 135 | 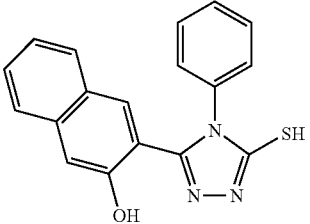 | 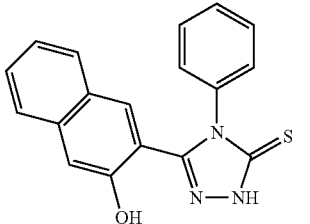 | 3-(3-Hydroxy-naphthalen-2-yl)-4-phenyl-5-mercapto-[1,2,4]triazole |
| 136 | 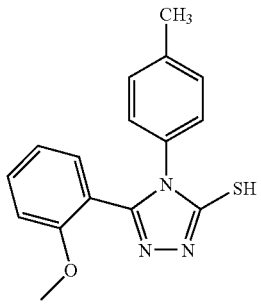 | 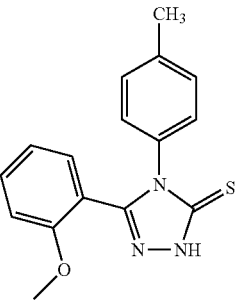 | 3-(2-Methoxy-phenyl)-4-(4-methyl-phenyl)-5-mercapto-[1,2,4]triazole |
| 137 | 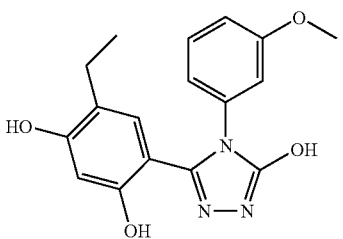 | 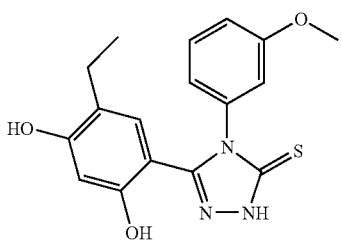 | 3-(2,4-Dihydroxy-5-ethyl-phenyl)-4-(3-methox-phenyl)-5-hydroxy-[1,2,4]triazole |

TABLE 1-continued

| No. | Structure | Tautomeric Structure | Name |
|---|---|---|---|
| 138 | 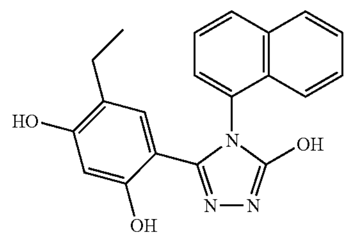 | | 3-(2,4-Dihydroxy-5-ethyl-phenyl)-4-(naphthalen-1-yl)-5-hydroxy-[1,2,4]triazole |
| 139 | 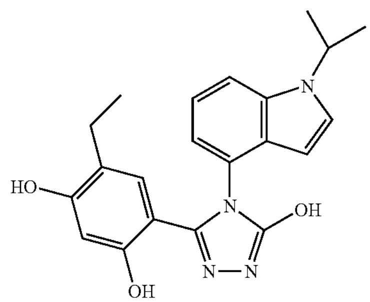 | | 3-(2,4-Dihydroxy-5-ethyl-phenyl)-4-(1-isopropyl-indol-3-yl)-5-hydroxy-[1,2,4]triazole |
| 140 | 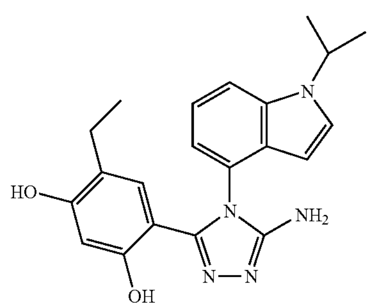 | | 3-(2,4-Dihydroxy-5-ethyl-phenyl)-4-(1-isopropyl-indol-4-yl)-5-amino-[1,2,4]triazole |
| 141 | 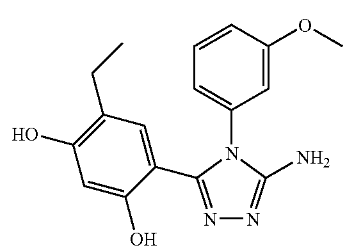 | | 3-(2,4-Dihydroxy-5-ethyl-phenyl)-4-(3-methoxy-phenyl)-5-amino-[1,2,4]triazole |
| 142 | 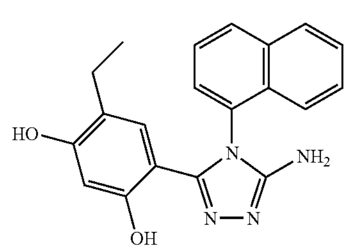 | | 3-(2,4-Dihydroxy-5-ethyl-phenyl)-4-(naphthalen-1-yl)-5-amino-[1,2,4]triazole |
| 143 | 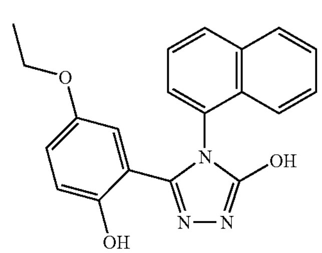 | | 3-(2-Hydroxy-5-ethyloxy-phenyl)-4-(naphthalen-1-yl)-5-hydroxy-[1,2,4]triazole |

TABLE 1-continued

| No. | Structure | Tautomeric Structure | Name |
| --- | --- | --- | --- |
| 144 | 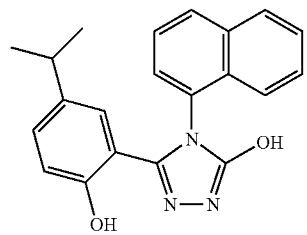 | | 3-(2-Hydroxy-5-isopropyl-phenyl)-4-(naphthalen-1-yl)-5-hydroxy-[1,2,4] triazole |
| 145 | 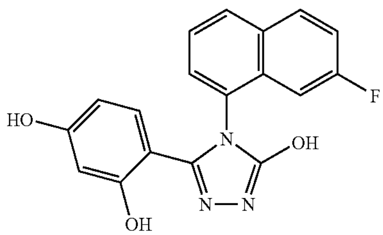 | | 3-(2-Dihydroxy-phenyl)-4-(7-fluoro-naphthalen-1-yl)-5-hydroxy-[1,2,4] triazole |
| 146 | 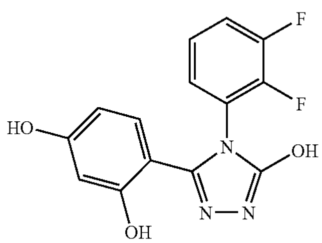 | | 3-(2,4-Dihydroxy-phenyl)-4-(2,3-difluorophenyl)-5-hydroxy-[1,2,4] triazole |
| 147 | 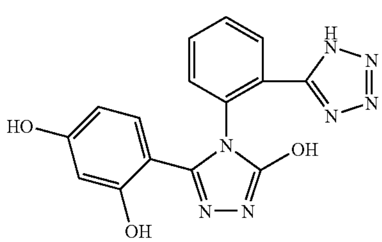 | | 3-(2,4-Dihydroxy-phenyl)-4-[2-(1H-tetrazol-5-yl)-phenyl]-5-hydroxy-[1,2,4] triazole |
| 148 | 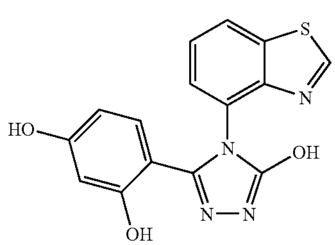 | | 3-(2,4-Dihydroxy-phenyl)-4-(benzothiazol-4-yl)-5-hydroxy-[1,2,4] triazole |
| 149 | 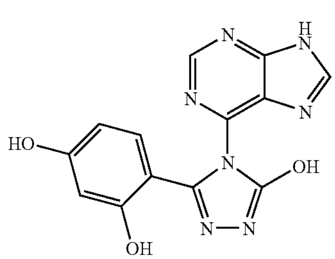 | | 3-(2,4-Dihydroxy-phenyl)-4-(9H-purin-6-yl)-5-hydroxy-[1,2,4] triazole |

TABLE 1-continued

| No. | Structure | Tautomeric Structure | Name |
|---|---|---|---|
| 150 | 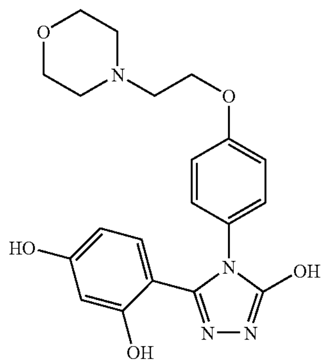 | | 3-(2,4-Dihydroxy-phenyl)-4-{4-[2-(morpholin-1-yl)-ethoxy]-phenyl}-5-hydroxy-[1,2,4]triazole |
| 151 | 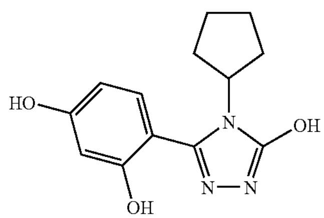 | | 3-(2,4-Dihydroxy-phenyl)-4-cyclopentyl-5-hydroxy-[1,2,4]triazole |
| 152 | 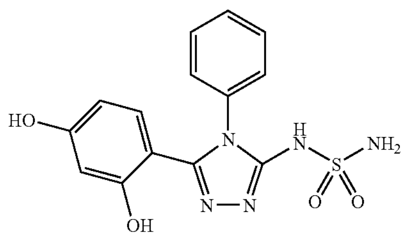 | | 3-(2,4-Dihydroxy-phenyl)-4-phenyl-5-(sulfamoylamino)-[1,2,4]triazole |
| 153 | 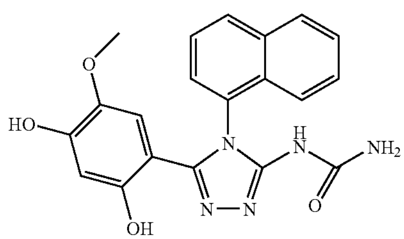 | | 3-(2,4-Dihydroxy-5-methoxy-phenyl)-4-(naphthalene-1-yl)-5-ureido-[1,2,4]triazole |
| 154 | 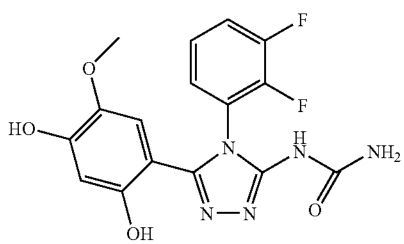 | | 3-(2,4-Dihydroxy-5-methoxy-phenyl)-4-(2,3-difluorophenyl)-5-ureido-[1,2,4]triazole |
| 155 | 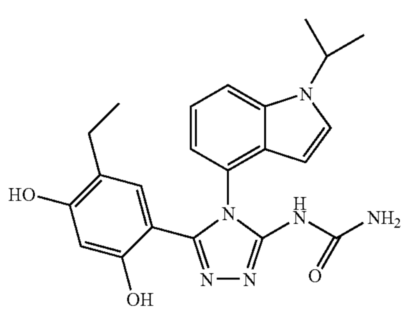 | | 3-(2,4-Dihydroxy-5-ethyl-phenyl)-4-(1-isopropyl-indol-4-yl)-5-ureido-[1,2,4]triazole |

TABLE 1-continued

| No. | Structure | Tautomeric Structure | Name |
|---|---|---|---|
| 156 | 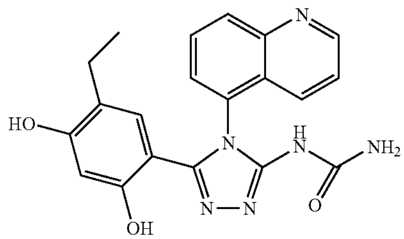 | | 3-(2,4-Dihydroxy-5-ethyl-phenyl)-4-(quinolin-5-yl)-5-ureido-[1,2,4]triazole |
| 157 | 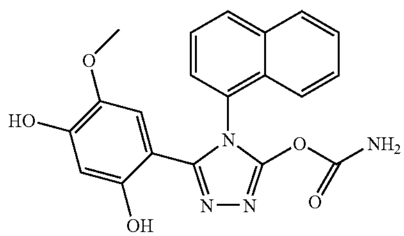 | | 3-(2,4-Dihydroxy-5-methoxy-phenyl)-4-(naphthalene-1-yl)-5-carbamoyloxy-[1,2,4]triazole |
| 158 | 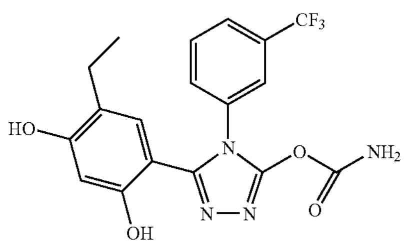 | | 3-(2,4-Dihydroxy-5-ethyl-phenyl)-4-(3-trifluoromethyl-phenyl)-5-carbamoyloxy-[1,2,4]triazole |
| 159 | 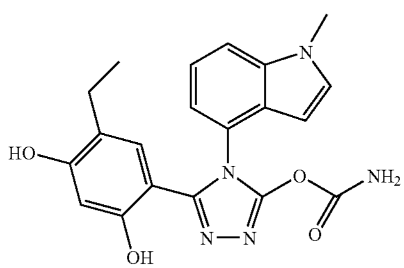 | | 3-(2,4-Dihydroxy-5-ethyl-phenyl)-4-(1-methyl-indol-4-yl)-5-carbamoyloxy-[1,2,4]triazole |
| 160 | 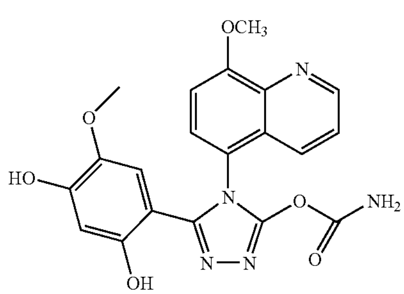 | | 3-(2,4-Dihydroxy-5-methoxy-phenyl)-4-(8-methoxy-quinolin-5-yl)-5-carbamoyloxy-[1,2,4]triazole |
| 161 | 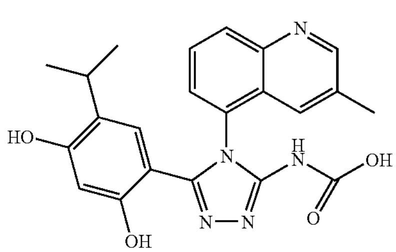 | | 3-(2,4-Dihydroxy-5-isopropyl-phenyl)-4-(3-methyl-quinolin-5-yl)-5-carbamoxyamino-[1,2,4]triazole |

TABLE 1-continued

| No. | Structure | Tautomeric Structure | Name |
|---|---|---|---|
| 162 | 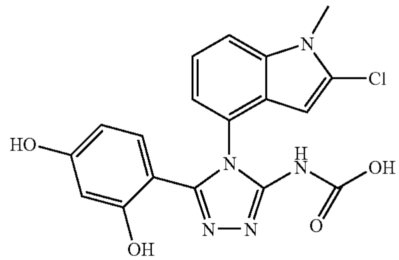 | | 3-(2,4-Dihydroxyphenyl)-4-(1-methyl-2-chloro-indol-4-yl)-5-carbamoyloxy-[1,2,4]triazole |
| 163 | 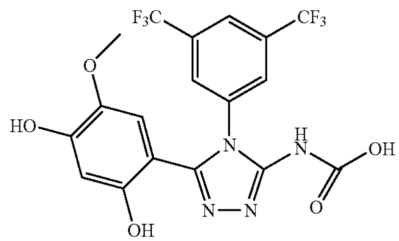 | | 3-(2,4-Dihydroxy-5-methoxy-phenyl)-4-[2,5-di-(trifluoromethyl)-phenyl]-5-carbamoyloxy-[1,2,4]triazole |
| 164 | 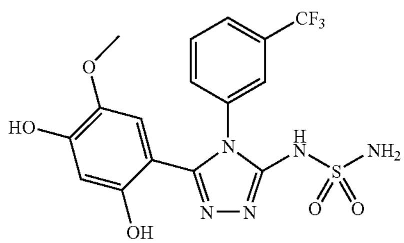 | | 3-(2,4-Dihydroxy-5-methoxy-phenyl)-4-(3-trifluoromethyl-phenyl)-5-(sulfamoylamino)-[1,2,4]triazole |
| 165 | 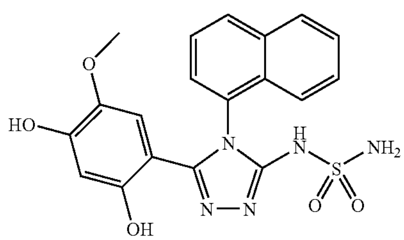 | | 3-(2,4-Dihydroxy-5-methoxy-phenyl)-4-(naphthalene-1-yl)-5-(sulfamoylamino)-[1,2,4]triazole |
| 166 | 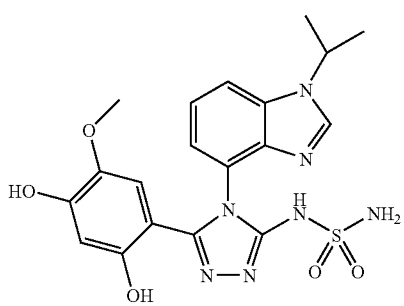 | | 3-(2,4-Dihydroxy-5-methoxy-phenyl)-4-(1-isopropyl-benzoimidazol-4-yl)-5-(sulfamoylamino)-[1,2,4]triazole |
| 167 | 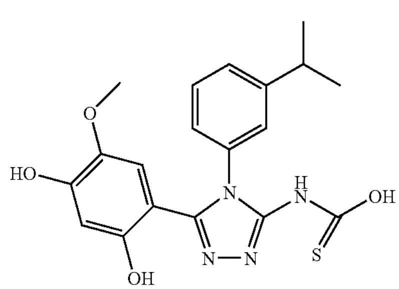 | | 3-(2,4-Dihydroxy-5-methoxy-phenyl)-4-(3-isopropylphenyl)-5-(thiocarboxyamino)-[1,2,4]triazole |

TABLE 1-continued

| No. | Structure | Tautomeric Structure | Name |
|---|---|---|---|
| 168 | 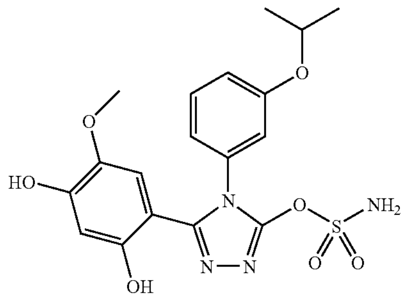 | | 3-(2,4-Dihydroxy-5-methoxy-phenyl)-4-(3-isopropyloxy-phenyl)-5-(sulfamoyloxy)-[1,2,4] triazole |
| 169 | 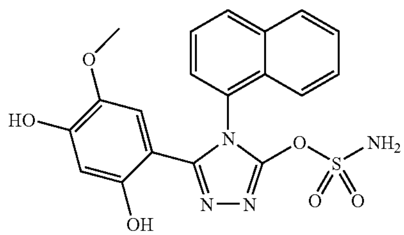 | | 3-(2,4-Dihydroxy-5-methoxy-phenyl)-4-(naphthalene-1-yl)-5-(sulfamoyloxy)-[1,2,4] triazole |
| 170 | 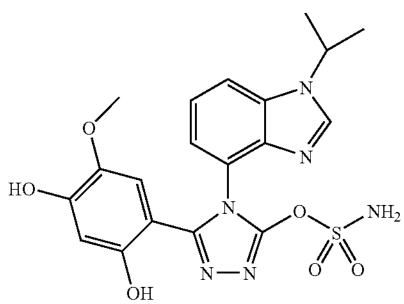 | | 3-(2,4-Dihydroxy-5-methoxy-phenyl)-4-(1-isopropyl-benzoimidazol-4-yl)-5-(sulfamoyloxy)-[1,2,4] triazole |
| 171 | 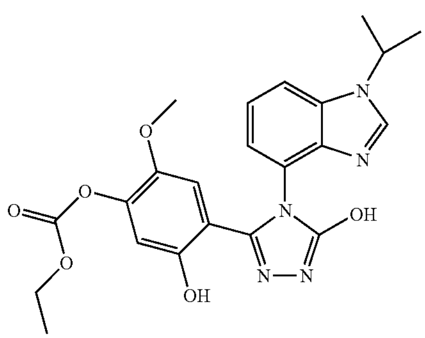 | | 3-(2-Hydroxy-4-ethoxycarbonyoxy-5-methoxy-phenyl)-4-(1-isopropyl-benzoimidazol-4-yl)-5-hydroxy-[1,2,4] triazole |
| 172 | 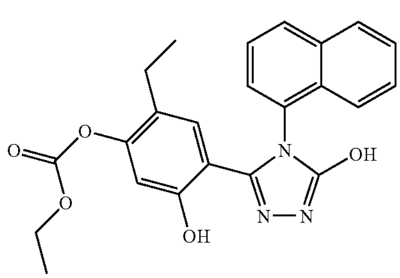 | | 3-(2-Hydroxy-4-ethoxycarbonyoxy-5-ethyl-phenyl)-4-(naphthalin-2-yl)-5-hydroxy-[1,2,4] triazole |

TABLE 1-continued

| No. | Structure | Tautomeric Structure | Name |
|---|---|---|---|
| 173 | 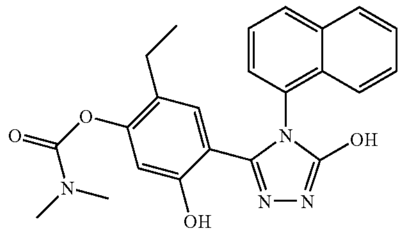 | | 3-[2-Hydroxy-4-(dimethyl-carbamoyoxy)-5-ethyl-phenyl]-4-(naphthalin-2-yl)-5-hydroxy-[1,2,4]triazole |
| 174 | 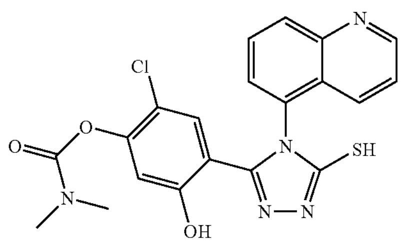 | | 3-[2-Hydroxy-4-(dimethyl-carbomoyoxy)-5-chloro-phenyl]-4-(quinolin-5-yl)-5-mercapto-[1,2,4]triazole |
| 175 | 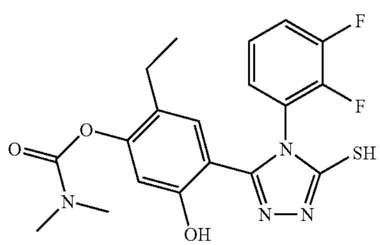 | | 3-[2-Hydroxy-4-(dimethyl-carbomoyoxy)-5-ethyl-phenyl]-4-(2,3-difluoro-phenyl)-5-mercapto-[1,2,4]triazole |
| 176 | 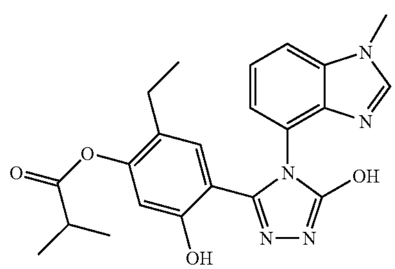 | | 3-[2-Hydroxy-4-isobutyryloxy-5-ethyl-phenyl]-4-(1-methyl-benzo-imidazol-4-yl)-5-hydroxy-[1,2,4]triazole |
| 177 | 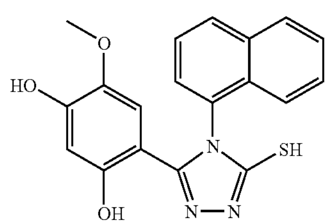 | | 3-(2,4-Dihydroxy-5-methoxy-phenyl)-4-(naphthalen-1-yl)-5-mercapto-[1,2,4]triazole |
| 178 | 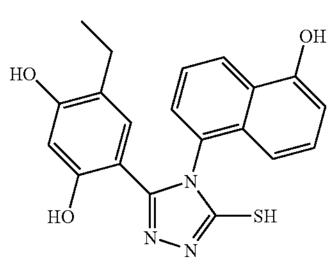 | | 3-(2,4-Dihydroxy-5-ethyl-phenyl)-4-(5-hydroxy-naphthalen-1-yl)-5-mercapto-[1,2,4]triazole |

TABLE 1-continued

| No. | Structure | Tautomeric Structure | Name |
| --- | --- | --- | --- |
| 179 | 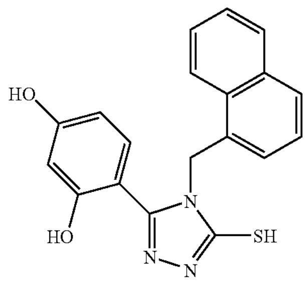 | | 3-(2,4-Dihydroxy-phenyl)-4-(naphthalen-1-ylmethyl)-5-mercapto-[1,2,4]triazole |
| 180 | 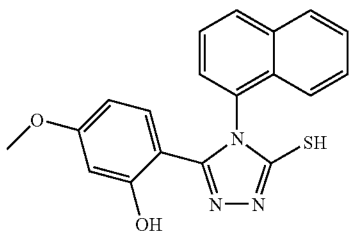 | | 3-(2-Hydroxy-4-methoxyphenyl)-4-(naphthalen-1-yl)-5-mercapto-[1,2,4]triazole |
| 181 | 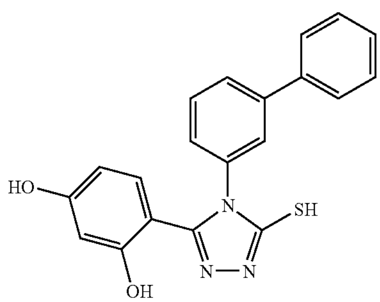 | | 3-(2,4-Dihydroxy-phenyl)-4-(biphenyl-3-yl)-5-mercapto-[1,2,4]triazole |
| 182 | 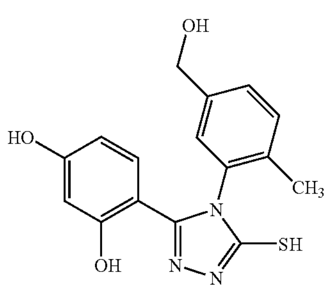 | | 3-(2,4-Dihydroxy-phenyl)-4-(2-methyl-5-hydroxymethyl-phenyl)-5-mercapto-[1,2,4]triazole |
| 183 | 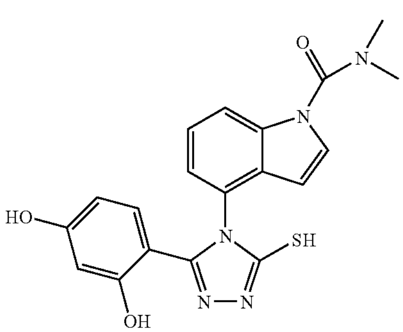 | | 3-(2,4-Dihydroxy-phenyl)-4-(1-dimethylcarbamoyl-indol-4-yl)-5-mercapto-[1,2,4]triazole |

TABLE 1-continued

| No. | Structure | Tautomeric Structure | Name |
|---|---|---|---|
| 184 | 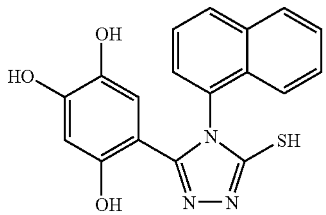 | | 3-(2,4,5-Trihydroxy-phenyl)-4-(naphthalene-1-yl)-5-mercapto-[1,2,4] triazole |
| 185 | 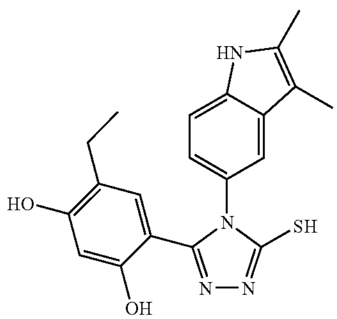 | | 3-(2,4-Dihydroxy-5-ethyl-phenyl)-4-(2,3-dimethyl-indol-5-yl)-5-mercapto-[1,2,4] triazole |
| 186 | 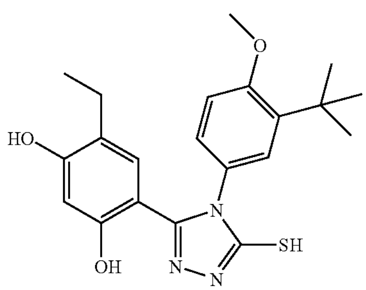 | | 3-(2,4-Dihydroxy-5-ethyl-phenyl)-4-(3-t-butyl-4-methoxy-phenyl)-5-mercapto-[1,2,4] triazole |
| 187 | 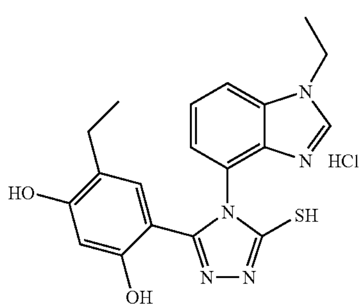 | | 3-(2,4-Dihydroxy-5-ethyl-phenyl)-4-(1-ethyl-1H-benzoimidazol-4-yl)-5-mercapto-[1,2,4] triazole, HCl salt |
| 188 | 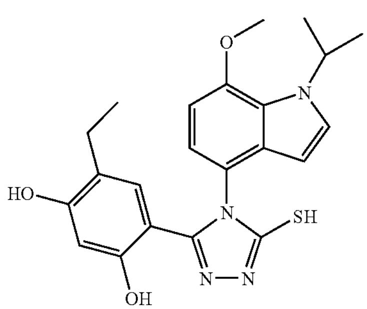 | | 3-(2,4-Dihydroxy-5-ethyl-phenyl)-4-(1-isopropyl-7-methoxy-indol-4-yl)-5-mercapto-[1,2,4] triazole |

TABLE 1-continued

| No. | Structure | Tautomeric Structure | Name |
|---|---|---|---|
| 189 | 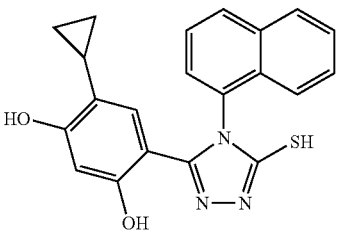 | 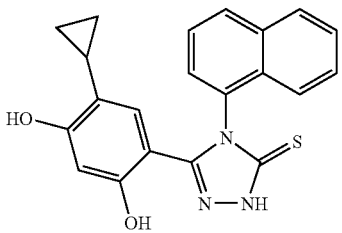 | 3-(2,4-Dihydroxy-5-cyclopropyl)-phenyl)-4-yl)-5-mercapto-[1,2,4] triazole |
| 190 | 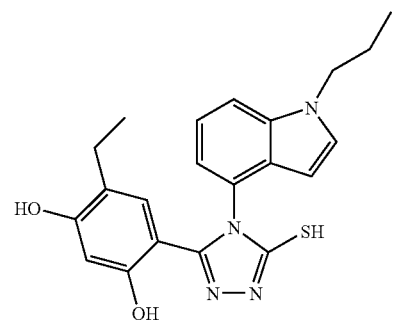 | 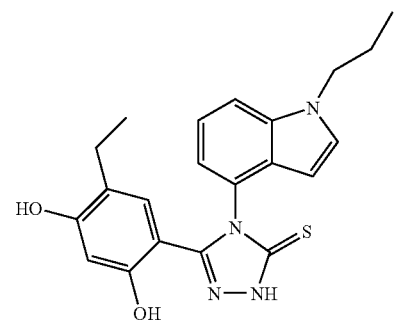 | 3-(2,4-dihydroxy-5-ethyl-phenyl)-4-(1-propyl-indol-4-yl)-5-mercapto-[1,2,4] triazole |
| 191 | 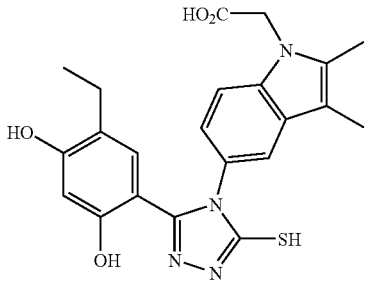 | 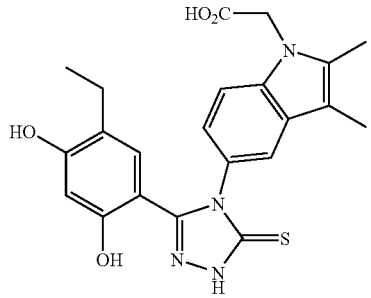 | 3-(2,4-dihydroxy-5-ethyl-phenyl)-4-(1-acetyl-2,3-dimethyl-indol-5-yl)-5-mercapto-[1,2,4] triazole |
| 192 | 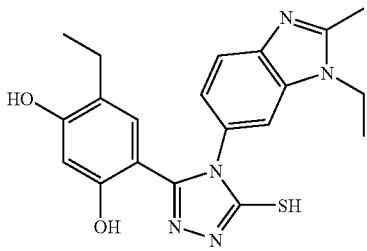 | 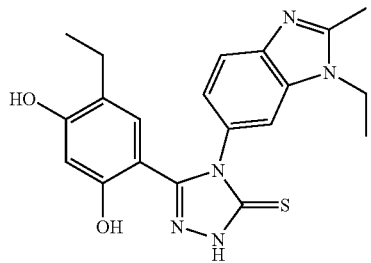 | 3-(2,4-dihydroxy-5-ethyl-phenyl)-4-(2-methyl-3-ethyl-benzimidazol-5-yl)-5-mercapto-[1,2,4] triazole |
| 193 | 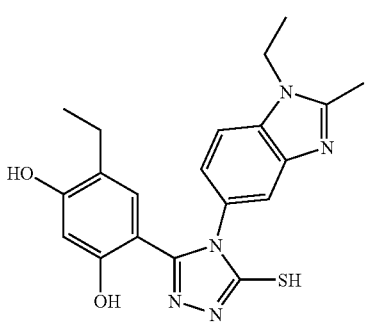 | 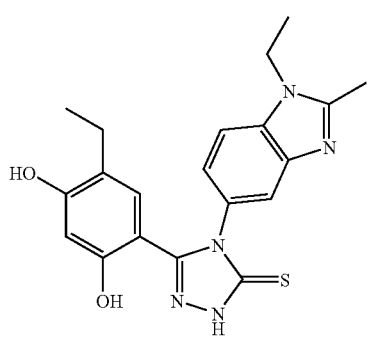 | 3-(2,4-dihydroxy-5-ethyl-phenyl)-4-(1-ethyl-2-methyl-benzimidazol-5-yl)-5-mercapto-[1,2,4] triazole |

TABLE 1-continued

| No. | Structure | Tautomeric Structure | Name |
|---|---|---|---|
| 194 | 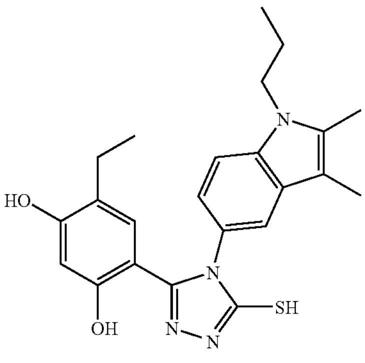 | | 3-(2,4-dihydroxy-5-ethyl-phenyl)-4-(1-propyl-2,3-dimethyl-indol-5-yl)-5-mercapto-[1,2,4] triazole |
| 195 | 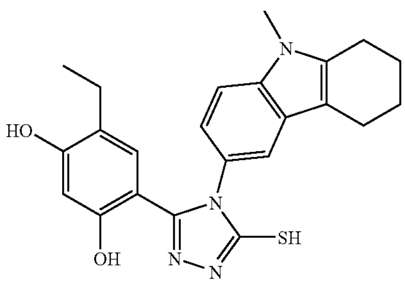 | | 3-(2,4-dihydroxy-5-ethyl-phenyl)-4-(N-methyl-tetrahydrocarbozol-7-yl)-5-mercapto-[1,2,4] triazole |
| 196 | 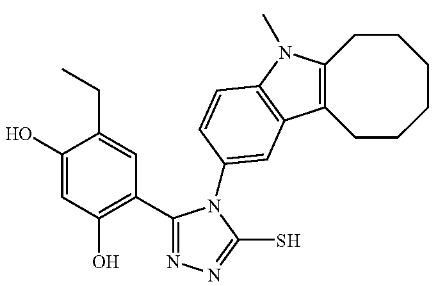 | | 3-(2,4-dihydroxy-5-ethyl-phenyl)-4-(N-methyl-cyclononan[a]indol-5-yl)-5-mercapto-[1,2,4] triazole |
| 197 | 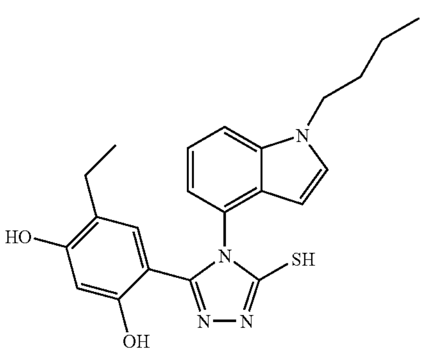 | | 3-(2,4-dihydroxy-5-ethyl-phenyl)-4-(1-n-butyl-indol-4-yl)-5-mercapto-[1,2,4] triazole |

TABLE 1-continued

| No. | Name |
|---|---|
| 198 | 3-(2,4-dihydroxy-5-ethyl-phenyl)-4-(1-n-pentyl-indol-4-yl)-5-mercapto-[1,2,4]triazole |
| 199 | 3-(2,4-dihydroxy-5-ethyl-phenyl)-4-(1-n-hexyl-indol-4-yl)-5-mercapto-[1,2,4]triazole |
| 200 | 3-(2,4-dihydroxy-5-cyclopropyl)-phenyl)-4-(1-(1-methylcyclopropyl)-indol-4-yl)-5-mercapto-[1,2,4]triazole |
| 201 | 3-(2,4-dihydroxy-5-cyclopropyl)-phenyl)-4-(1-isopropyl-7-methoxy)-indol-4-yl)-5-mercapto-[1,2,4]triazole |

TABLE 1-continued

| No. | Structure | Tautomeric Structure | Name |
| --- | --- | --- | --- |
| 202 | 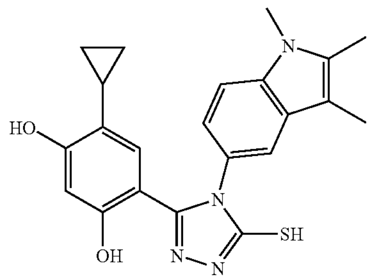 | | 3-(2,4-dihydroxy-5-cyclopropyl-phenyl)-4-(1,2,3-trimethyl-indol-5-yl)-5-mercapto-[1,2,4] triazole |
| 203 | 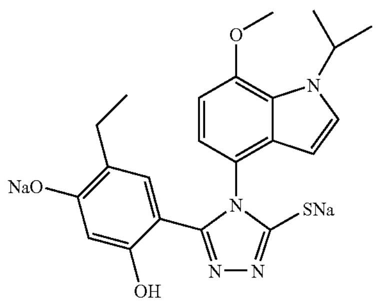 | | 3-(2,4-dihydroxy-5-ethyl-phenyl)-4-(1-isopropyl-7-methoxy-indol-4-yl)-5-mercapto-[1,2,4] triazole disodium salt |
| 204 | 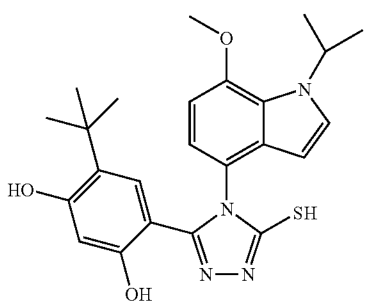 | | 3-(2,4-dihydroxy-5-tert-butyl-phenyl)-4-(1-isopropyl-7-methoxy-indol-4-yl)-5-mercapto-[1,2,4] triazole |
| 205 | 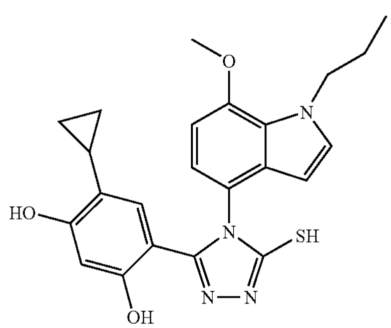 | | 3-(2,4-dihydroxy-5-cyclopropyl-phenyl)-4-(1-propyl-7-methoxy-indol-4-yl)-5-mercapto-[1,2,4] triazole |
| 206 | 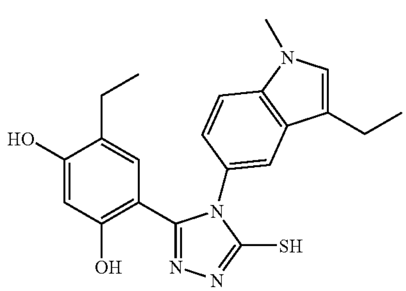 | | 3-(2,4-dihydroxy-5-ethyl-phenyl)-4-(1-methyl-3-ethyl-indol-5-yl)-5-mercapto-[1,2,4] triazole disodium salt |

TABLE 1-continued

| No. | Structure | Tautomeric Structure | Name |
|---|---|---|---|
| 207 | 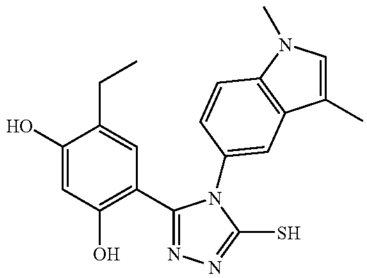 | | 3-(2,4-dihydroxy-5-ethyl-phenyl)-4-(1,3-dimethyl-indol-5-yl)-5-mercapto-[1,2,4]triazole |
| 208 | 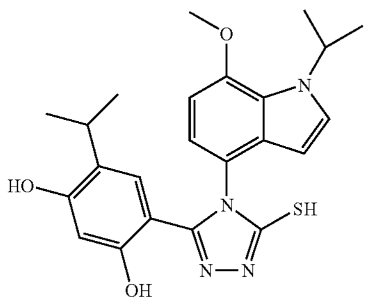 | | 3-(2,4-dihydroxy-5-isopropyl-phenyl)-4-(1-isopropyl-7-methoxy-indol-4-yl)-5-mercapto-[1,2,4]triazole |
| 209 | 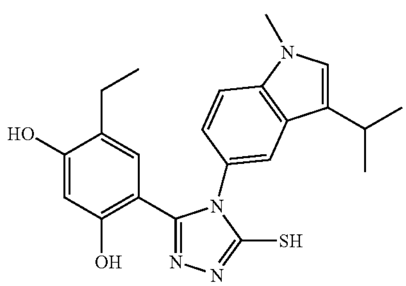 | | 3-(2,4-dihydroxy-5-ethyl-phenyl)-4-(1-methyl-3-isopropyl-indol-5-yl)-5-mercapto-[1,2,4]triazole |
| 210 | 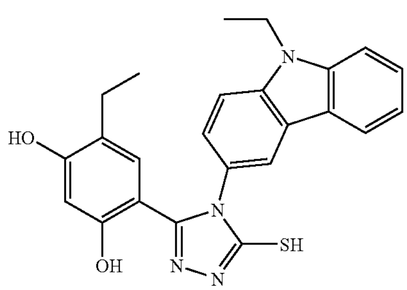 | | 3-(2,4-dihydroxy-5-ethyl-phenyl)-4-(N-ethyl-carbozol-7-yl)-5-mercapto-[1,2,4]triazole |
| 211 | 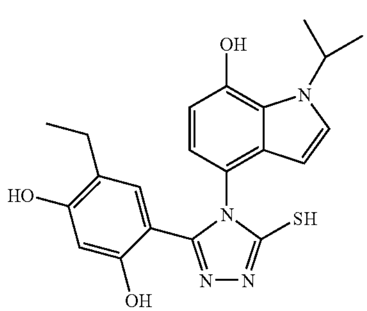 | | 3-(2,4-dihydroxy-5-ethyl-phenyl)-4-(1-isopropyl-7-hydroxy-indol-4-yl)-5-mercapto-[1,2,4]triazole |

TABLE 1-continued

| No. | Structure | Tautomeric Structure | Name |
|---|---|---|---|
| 212 | 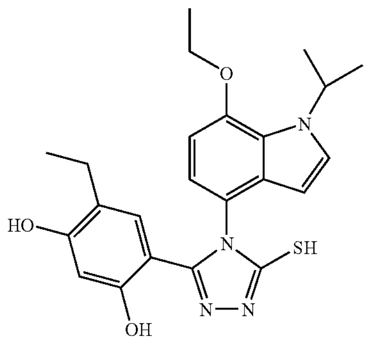 | | 3-(2,4-dihydroxy-5-ethyl-phenyl)-4-(1-isopropyl-7-ethoxy-indol-4-yl)-5-mercapto-[1,2,4] triazole |
| 213 | 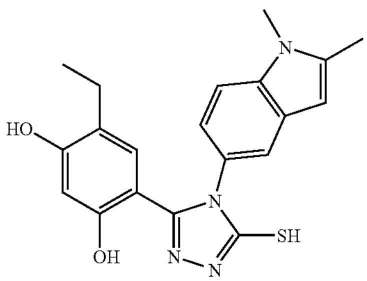 | | 3-(2,4-dihydroxy-5-ethyl-phenyl)-4-(1,2-dimethyl-indol-5-yl)-5-mercapto-[1,2,4] triazole |
| 214 | 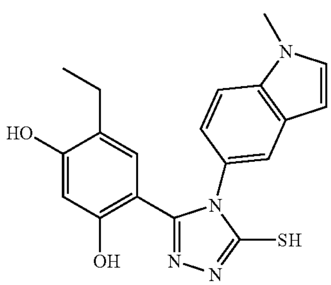 | | 3-(2,4-dihydroxy-5-ethyl-phenyl)-4-(N-methyl-indol-5-yl)-5-mercapto-[1,2,4] triazole |
| 215 | 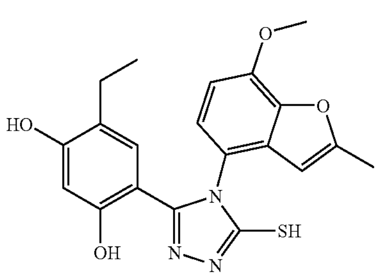 | | 3-(2,4-dihydroxy-5-ethyl-phenyl)-4-(2-methyl-7-methoxy-benzofuran-4-yl)-5-mercapto-[1,2,4] triazole |
| 216 | 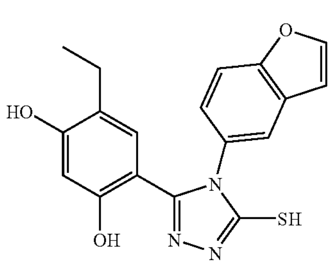 | | 3-(2,4-dihydroxy-5-ethyl-phenyl)-4-(benzofuran-5-yl)-5-mercapto-[1,2,4] triazole |

TABLE 1-continued

| No. | Structure | Tautomeric Structure | Name |
|---|---|---|---|
| 217 | 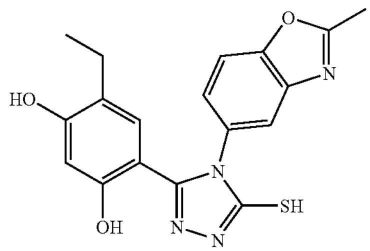 | | 3-(2,4-dihydroxy-5-ethyl-phenyl)-4-(2-methyl-1,3-benzoxaz-5-yl)-5-mercapto-[1,2,4]triazole |
| 218 | 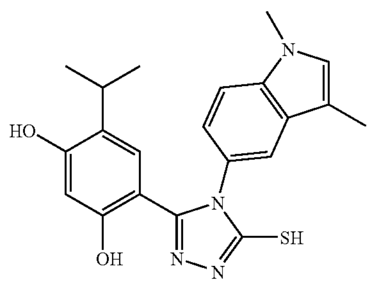 | | 3-(2,4-dihydroxy-5-isopropyl-phenyl)-4-(1,3-dimethyl-indol-5-yl)-5-mercapto-[1,2,4]triazole |
| 219 | 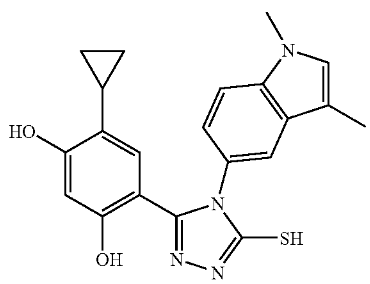 | | 3-(2,4-dihydroxy-5-cyclopropyl-phenyl)-4-(1,3-dimethyl-indol-5-yl)-5-mercapto-[1,2,4]triazole |
| 220 | 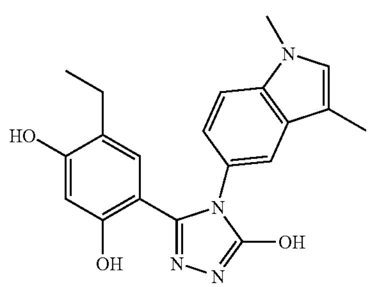 | | 3-(2,4-dihydroxy-5-ethyl-phenyl)-4-(1,3-dimethyl-indol-5-yl)-5-hydroxy-[1,2,4]triazole |
| 221 | 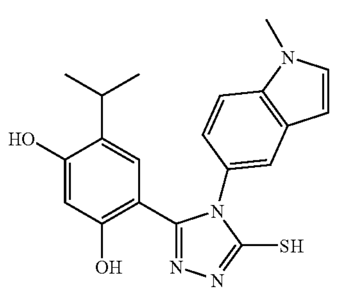 | | 3-(2,4-dihydroxy-5-isopropyl-phenyl)-4-(N-methyl-indol-5-yl)-5-mercapto-[1,2,4]triazole |

TABLE 1-continued

| No. | Structure | Tautomeric Structure | Name |
|---|---|---|---|
| 222 | 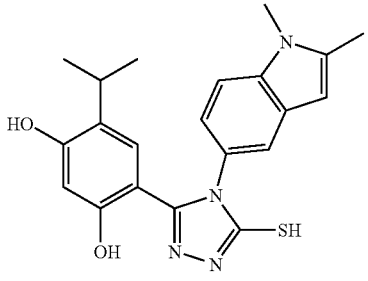 | 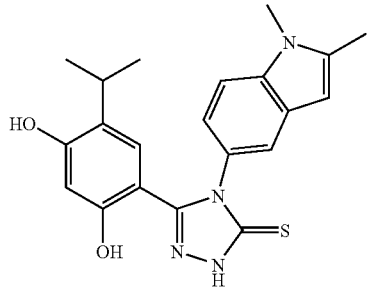 | 3-(2,4-dihydroxy-5-isopropyl-phenyl)-4-(1,2-dimethyl-indol-5-yl)-5-mercapto-[1,2,4] triazole |
| 223 | 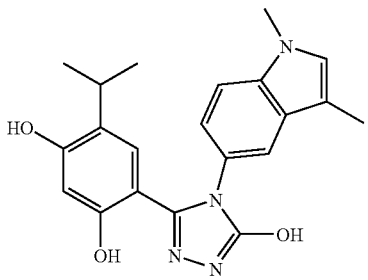 | 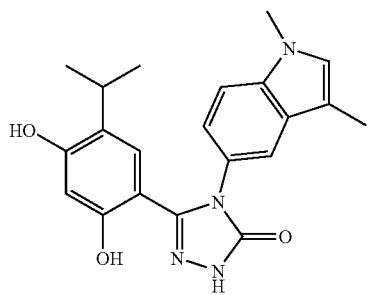 | 3-(2,4-dihydroxy-5-isopropyl-phenyl)-4-(1,3-dimethyl-indol-5-yl)-5-hydroxy-[1,2,4] triazole |
| 224 | 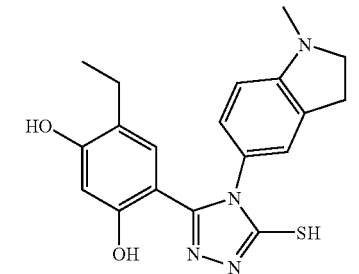 | 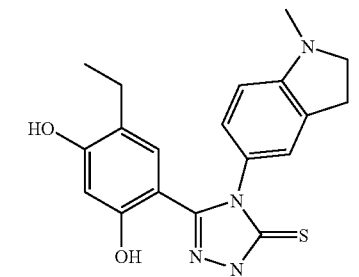 | 3-(2,4-dihydroxy-5-cyclopropyl-phenyl)-4-(1-methyl-indol-5-yl)-5-mercapto-[1,2,4] triazole |
| 225 | 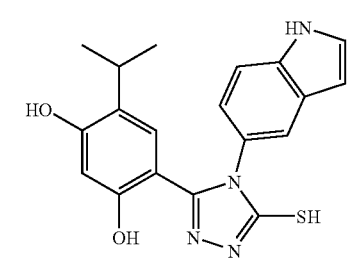 | 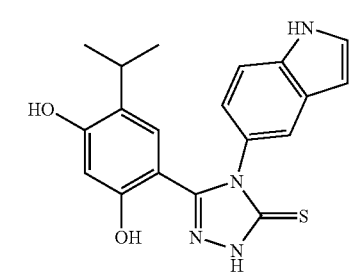 | 3-(2,4-dihydroxy-5-isopropyl-phenyl)-4-(1H-indol-5-yl)-5-mercapto-[1,2,4] triazole |
| 226 | 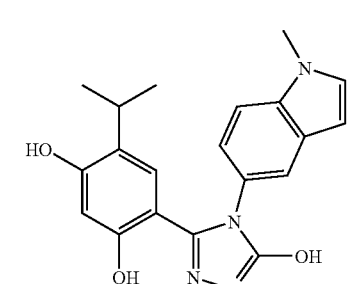 | 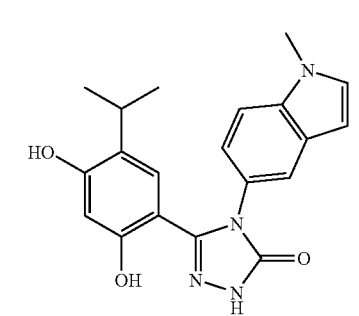 | 3-(2,4-dihydroxy-5-isopropyl-phenyl)-4-(1-methyl-indol-5-yl)-5-hydroxy-[1,2,4] triazole |

TABLE 1-continued

| No. | Structure | Tautomeric Structure | Name |
|---|---|---|---|
| 227 | 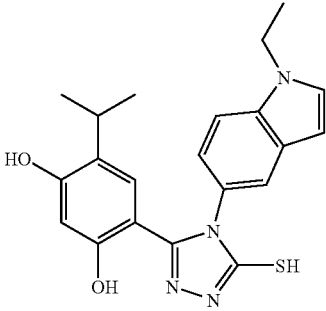 | 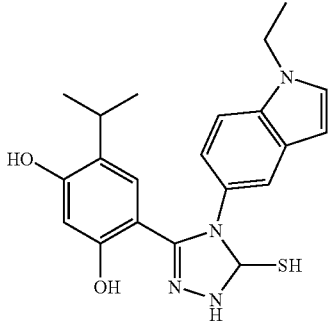 | 3-(2,4-dihydroxy-5-isopropyl-phenyl)-4-(1-ethyl-indol-5-yl)-5-mercapto-[1,2,4] triazole |
| 228 | 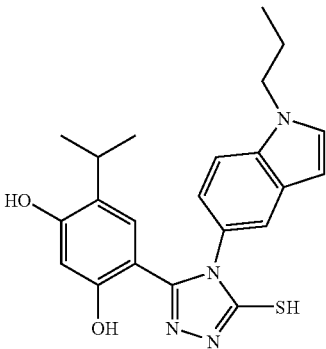 | 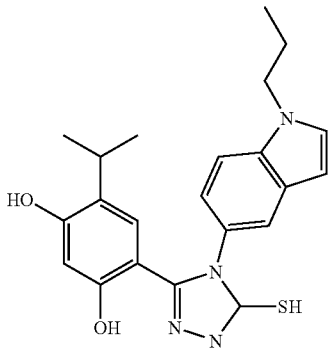 | 3-(2,4-dihydroxy-5-isopropyl-phenyl)-4-(1-propyl-indol-5-yl)-5-mercapto-[1,2,4] triazole |
| 229 | 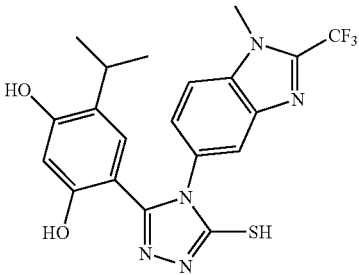 | 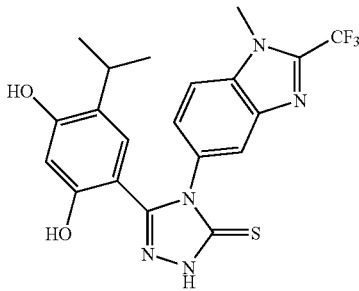 | 3-(2,4-dihydroxy-5-isopropyl-phenyl)-4-(1-methyl-2-trifluoromethyl-benzimidazol-5-yl)-5-mercapto-[1,2,4] triazole |
| 230 | 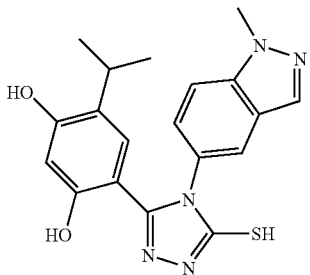 | 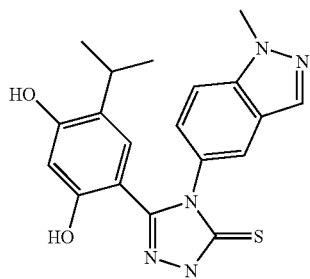 | 3-(2,4-dihydroxy-5-isopropyl-phenyl)-4-(1-methyl-indazol-5-yl)-5-mercapto-[1,2,4] triazole |
| 231 | 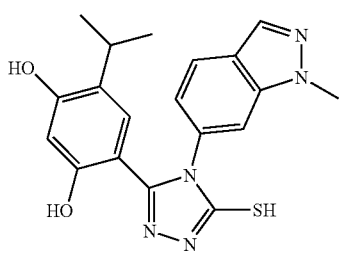 | 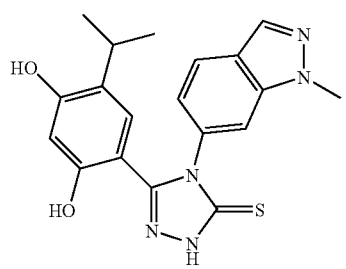 | 3-(2,4-dihydroxy-5-isopropyl-phenyl)-4-(1-methyl-indazol-6-yl)-5-mercapto-[1,2,4] triazole |

TABLE 1-continued

| No. | Name |
|---|---|
| 232 | 3-(2,4-dihydroxy-5-isopropyl-phenyl)-4-(1-isopropyl-indol-4-yl)-5-hydroxy-[1,2,4] triazole |
| 233 | 3-(2,4-dihydroxy-5-isopropyl-phenyl)-4-(1,3-benzodiaxol-5-yl)-5-mercapto-[1,2,4] triazole |
| 234 | 3-(2,4-dihydroxy-5-isopropyl-phenyl)-4-(indan-5-yl)-5-mercapto-[1,2,4] triazole |
| 235 | 3-(2,4-dihydroxy-5-isopropyl-phenyl)-4-(2-methyl-indazol-6-yl)-5-mercapto-[1,2,4] triazole |
| 236 | 3-(2,4-dihydroxy-5-ethyl-phenyl)-4-(3-oxo-benzo[1,4]oxazin-6-yl-(5-mercapto-[1,2,4] triazole |

TABLE 1-continued

| No. | Structure | Tautomeric Structure | Name |
|---|---|---|---|
| 237 | 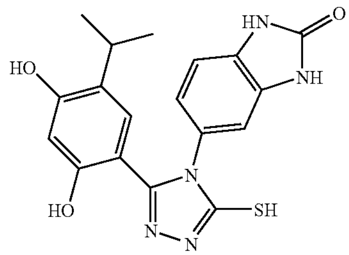 | | 3-(2,4-dihydroxy-5-ethyl-phenyl)-4-(2-oxo-1,3-dihydro-benzoimidazol-5-yl)-5-mercapto-[1,2,4] triazole |
| 238 | 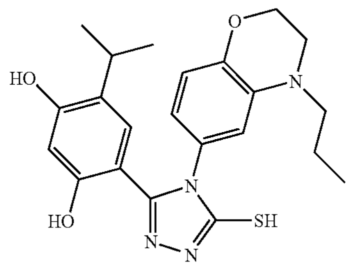 | | 3-(2,4-dihydroxy-5-isopropyl-phenyl)-4-(2H-benzo[1,4]oxazin-6-yl)-5-mercapto-[1,2,4] triazole |
| 239 | 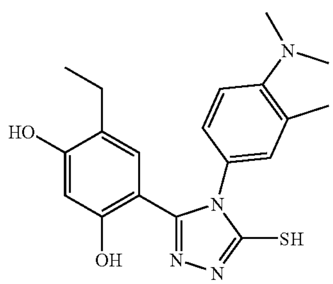 | | 4-Ethyl-6-[5-mercapto-4-(1-methyl-2,3-dihydro-1H-indol-5-yl)-4H-[1,2,4]triazol-3-yl]-benzene-1,3-diol |
| 240 | 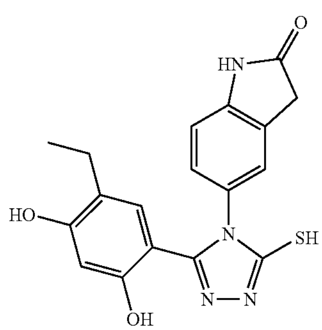 | | 5-(3-(5-ethyl-2,4-dihydroxyphenyl)-5-mercapto-4H-1,2,4-triazol-4-yl)indolin-2-one |
| 241 | 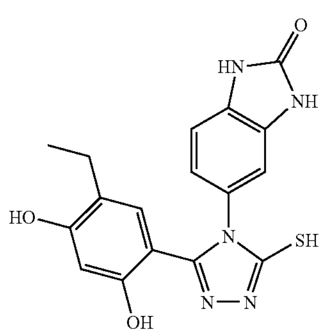 | | 5-(3-(5-ethyl-2,4-dihydroxyphenyl)-5-mercapto-4H-1,2,4-triazol-4-yl)-1H-benzo[d]imidazol-2(3H)-one |

TABLE 1-continued

| No. | Structure | Tautomeric Structure | Name |
|---|---|---|---|
| 242 | 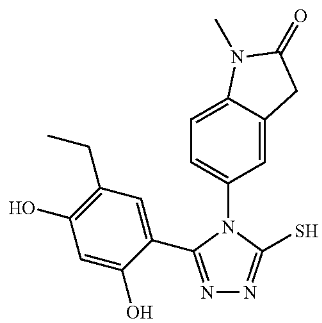 | | 5-(3-(5-ethyl-2,4-dihydroxyphenyl)-5-mercapto-4H-1,2,4-triazol-4-yl)-1-methylindolin-2-one |
| 243 | 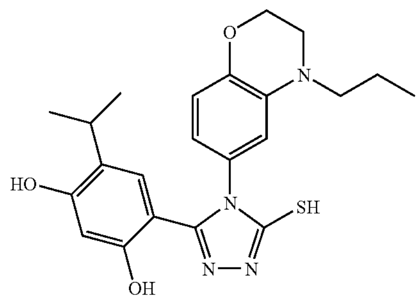 | | 4-isopropyl-6-(5-mercapto-4-(4-propyl-3,4-dihydro-2H-benzo[b][1,4]oxazin-6-yl)-4H-1,2,4-triazol-3-yl)benzene-1,3-diol |
| 244 | 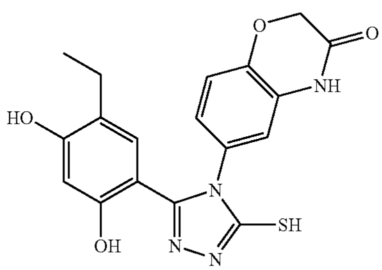 | | 6-(3-(5-ethyl-2,4-dihydroxyphenyl)-5-mercapto-4H-1,2,4-triazol-4-yl)-2H-benzo[b][1,4]oxazin-3(4H)-one |
| 245 | 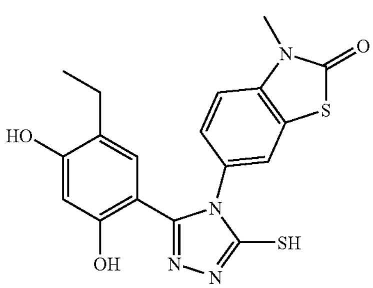 | | 6-(3-(5-ethyl-2,4-dihydroxyphenyl)-5-mercapto-4H-1,2,4-triazol-4-yl)-3-methylbenzo[d]thiazol-2(3H)-one |
| 246 | 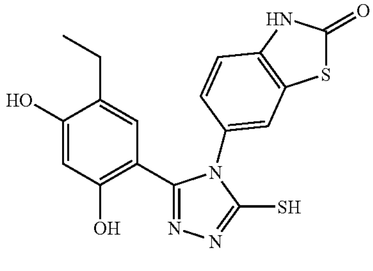 | | 6-(3-(5-ethyl-2,4-dihydroxyphenyl)-5-mercapto-4H-1,2,4-triazol-4-yl)benzo[d]thiazol-2(3H)-one |

Preferred compounds of the invention are those compounds that can form a tautomeric structure as shown below and as exemplified by the tautomeric structures shown in Table 1:

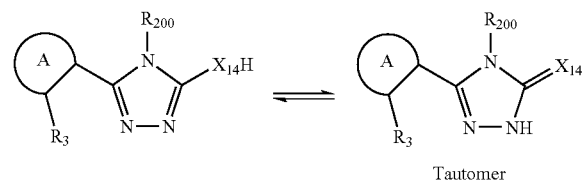

Tautomer $R_{200} = R_2, R_5, $ or $R_{18}$
$X_{14} = O, S, $ or $NR_7$

Similarly, prodrugs, i.e. compounds which can be metabolized or hydrolyzed in vivo to a compound of the present invention are encompassed by the present description. For example, the following embodiments of a compound of the present invention can be produced in vivo in the following reaction:

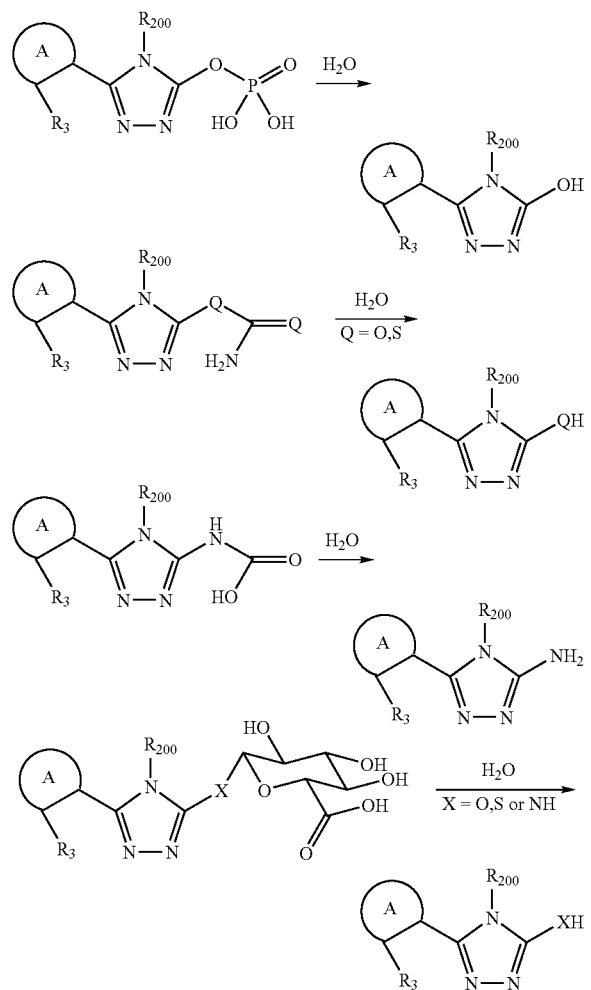

where $R_{200}$ is $R_2$, $R_5$ or $R_{18}$.

One skilled in the art will understand that other hydrolyzable protecting groups can be employed with the compounds of the present invention to obtain prodrugs encompassed by the present description.

Without wishing to be bound by any theory, it is believed that the compounds of the invention preferentially bind to Hsp90 in the tautomeric form shown above, and thereby inhibit the activity of Hsp90.

C. Methods for Making Compounds of the Invention

Compounds of the invention can be obtained via standard, well-known synthetic methodology, see e.g., March, J. Advanced Organic Chemistry; Reactions Mechanisms, and Structure, 4th ed., 1992.

Compounds of the invention can also be made as in the following provisional applications: 60/808,376, filed May 25, 2006; 60/808,342, filed May 25, 2006; and 60/808,375, filed May 25, 2006, which are incorporated by reference herein in their entirety.

In particular, compounds of the invention can be obtained by heating a hydrazide (A) with an isocyanate ($X_{14}$=O), isothiocyanate, ($X_{14}$=S) or carbodiimide ($X_{14}$=$NR_7$) (B) in an alcohol to form intermediate (C). Intermediate (C) can be cyclized to form a triazole core (D) by heating it in an aqueous solution which includes about 2 molar equivalents of NaOH (see Scheme I below). Starting materials useful for preparing compounds of the invention and intermediates therefore, are commercially available or can be prepared from commercially available materials using known synthetic methods and reagents. For example, a hydrazide can be prepared by reacting an ester (such as 2,4-dihydroxybenzoic acid methyl ester) or acid chloride with hydrazine. Isocyanates and isothiocyanates ($X_{14}$ is O or S, respectively) can be formed in a number of ways from compounds that have a primary amine group. For example, a primary amine can be reacted with phosgene or thiophosgene to form an isocyanate or an isothiocyanate, respectively. Alternatively, a cyanate or thiocyanate ion can be reacted with an alkyl halide to form an alkyl isocyanate or an alkyl isothiocyanate. In addition, a isothiocyanate can be prepared by reacting a diazonium salt with a thiocyanate ion. Carbodiimides ($X_{14}$ is $NR_7$) can be prepared by dehydration of ureas using a dehydration agent such as tosyl chloride in pyridine, $POCl_3$, $PCl_5$, $P_2O_5$-pyridine, and $Ph_3PBr_2$-$Et_3N$. Other methods of preparing isocyanates, thioisocyanates, and carbodiimides can be found in March, J. Advanced Organic Chemistry; Reactions Mechanisms, and Structure, 4th ed., 1992, the entire teachings of which are incorporated by reference.

Compounds represented by formulas (IV) and (V) can be made in an analogous fashion as compounds depicted in Scheme I.

Reactive functional groups can be protected during one or more reaction step, then deprotected to restore the original functionality. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

Scheme I: Synthesis of triazole compounds of the invention

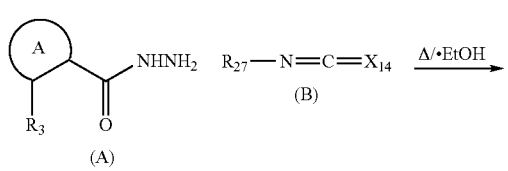

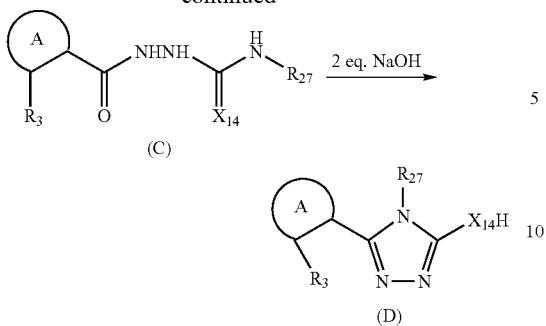

$R_{27} = R_2, R_5, \text{ or } R_{18}$
$X_{14} = O, S, \text{ or } NR_7$

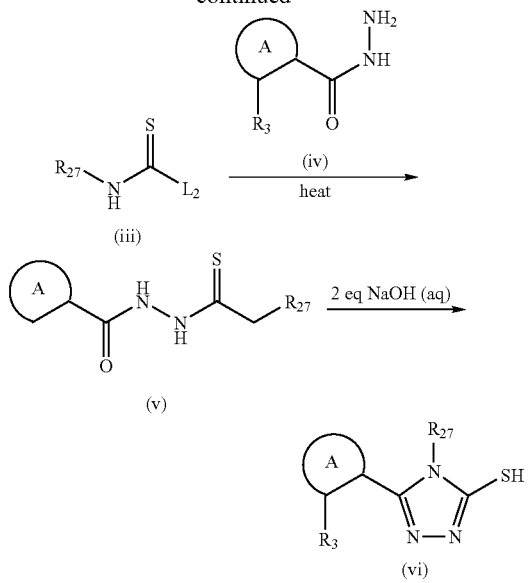

An alternative method of preparing the compounds of the invention is shown in Scheme II. In this method, an aryl, heteroaryl, cycloalkyl, or alkyl amine compound (i) is stirred at about room temperature with a thiocarbonyl (ii) which has two leaving groups, $L_1$ and $L_2$, such as imidazole-1-yl groups, to form compound (iii). Typically, the thiocarbonyl compound is present in a slight molar excess of about 1.05 eq. to about 1.3 eq. compared with compound (i). Compound (iii) is then combined with a hydrazide compound (iv) in a solvent and heated to about 50° C. to about 100° C. for about 0.5 to 5 hrs to form compound (v). Typically, compound (iii) and compound (iv) can be present in about equal molar ratio or a slight excess of compound (iii), such as about 1.01 to about 1.1 molar eq. of compound (iii) compare to compound (iv). Compound (v) can then be cyclized to form a triazole compound of the invention (vi) by suspending it in aqueous solution containing about 2 molar eq. of NaOH and heating the solution to about 75° C. to about 110° C. for about 0.5 hr to about 2 hrs. Typically, the NaOH solution containing compound (v) is degassed before heating by bubbling an inert gas, such as nitrogen or argon, through it.

Scheme II: Alternative synthesis of triazole compounds of the invention

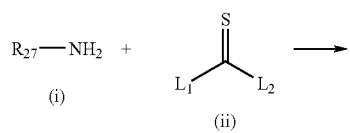

In one embodiment, ring A of the compounds of the invention is a 2,4-dihydroxyphenyl group. In this embodiment, it is sometimes desirable to prepare a prodrug by protecting the 4-hydroxy group with a moiety that can be hydrolyzed in vivo. Protection of 4-hydroxy group is expected to improve the circulating half-life of compound compounds of the invention. In addition, it is desirable that a group added to the 4-hydroxy group increase the water solubility of the compounds of the invention. In one embodiment, 4-methyl-piperizine-1-carbamoyl group is used to protect the 4-hydroxy group (see Scheme III). In this embodiment, a compound of the invention, such as compound (E), is treated with about one molar equivalents of 4-methyl-piperizine-1-carbonyl chloride (F) in the presence of a base to form compound (G) in which the 4-hydroxy group is protected. Alternatively, the mercapto group can be protected first by reacting compound (E) with about one molar equivalent of acyl chloride in the presence of a base to form intermediate (H). Intermediate (H) can them be reacted with about one molar equivalent of 4-methyl-piperizine-1-carbonyl chloride (F) in the presence of a base, then the acetyl group can be removed by treatment with a mild acid to form compound (G).

Scheme III: Preparation of prodrugs in which the 4-hydroxy group of compounds of the invention is protected with 4-methyl-piperizine-1-carbamoyl.

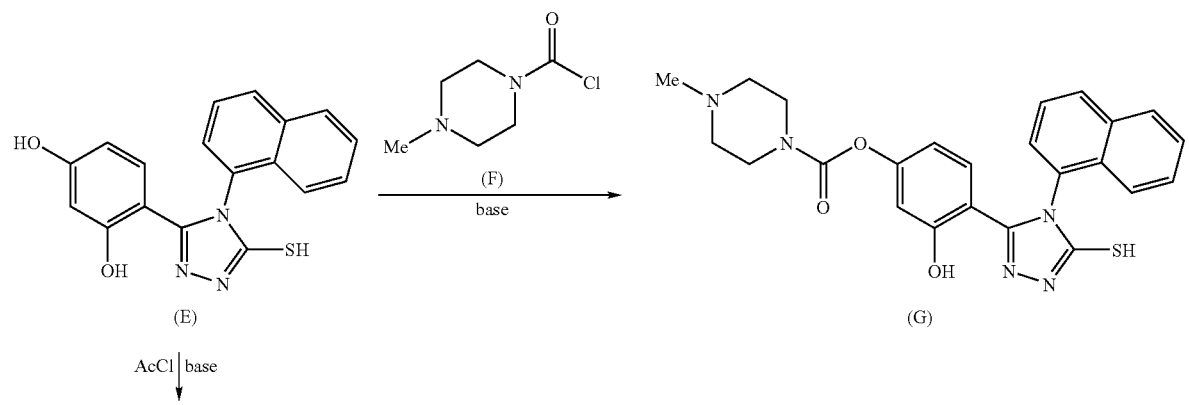

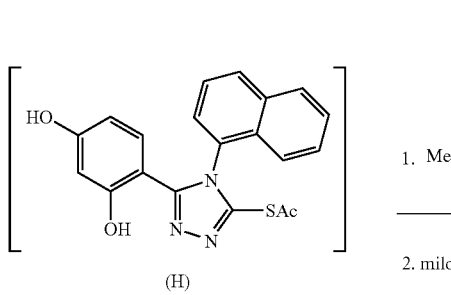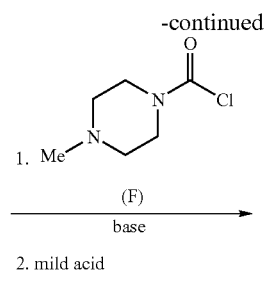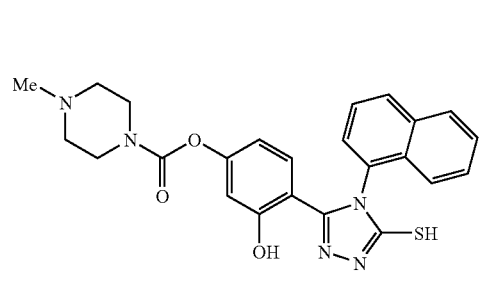

Another prodrug of compounds of the invention can be formed by addition of a phosphate group to the 4-hydroxy group (Scheme IV). In this embodiment, a compound of the invention, such as compound (E), is treated with about one molar equivalent of diisopropyl phosphoramidous acid di-t-butyl ester in the presence of tetrazole to yield compound (J). The phosphorous group is then oxidized with m-CPBA to form a phosphoric acid di-t-butyl ester group of compound K. The t-butyl groups are then hydrolyzed with trifluoroacetic acid (TFA) to yield a phosphoric acid group or compound L.

Scheme IV: Preparation of prodrugs in which the 4-hydroxy group of compounds of the invention is protected with a phosphate group.

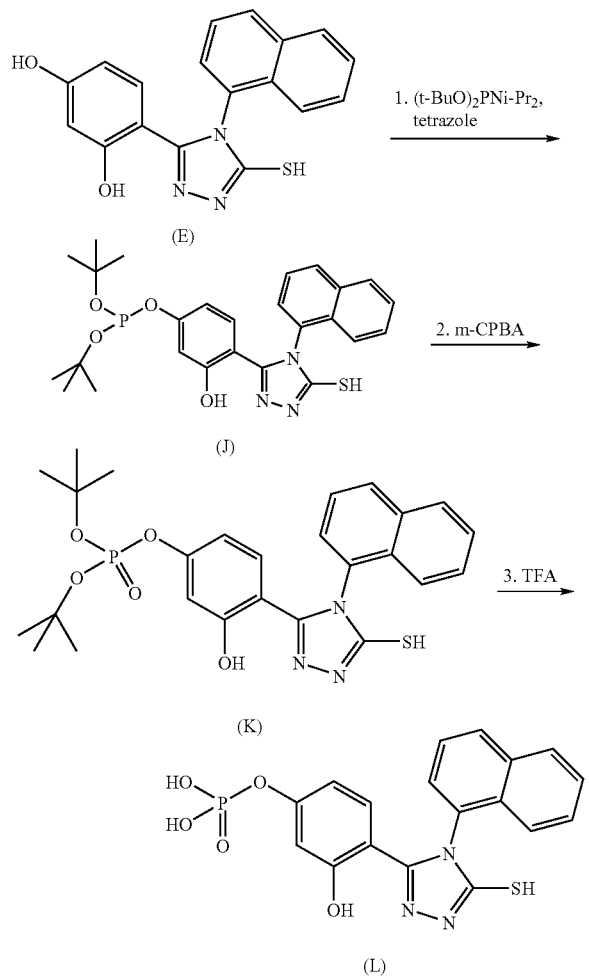

D. Uses of Compounds of the Invention

The present invention provides methods for treating, reducing or inhibiting angiogenesis in a subject in need thereof, comprising administering to the subject an effective amount of a compound represented by formula (I), (II), (III), (IV), (V), (VI), (VII), (VIII), (IX), (X), or any embodiment thereof, or a compound shown in Table 1.

In one aspect, compounds of the invention are used in combination with one or more other therapeutic agents. In one aspect, compounds of the invention are used in combination with one or more other anti-angiogenic agents.

In another aspect, the invention provides methods of reducing, blocking, occluding, or otherwise disrupting blood flow in neovasculature, comprising contacting the neovasculature with an effective amount of a compound represented by formula (I), (II), (III), (IV), (V), (VI), (VII), (VIII), (IX), (X), or any embodiment thereof, or a compound shown in Table 1. In one aspect, the neovasculature is in a subject and blood flow in the neovasculature is reduced, blocked, occluded, or otherwise disrupted in the subject by administering to the subject an effective amount of a compound represented by formula (I), (II), (III), (IV), (V), (VI), (VII), (VIII), (IX), (X), or any embodiment thereof, or a compound shown in Table 1. In one aspect, the subject is human.

2. Agents Useful in Combination with the Compounds of the Invention

Anti-angiogenesis agents that can be co-administered with the compounds of the invention include Dalteparin, Suramin, ABT-510, Combretastatin A4 Phosphate, Lenalidomide, LY317615 (Enzastaurin), Soy Isoflavone (Genistein; Soy Protein Isolate), Thalidomide, AMG-706, Anti-VEGF Antibody (Bevacizumab; Avastin™), AZD2171, Bay 43-9006 (Sorafenib tosylate), PI-88, PTK787/ZK 222584 (Vatalanib), SU11248 (Sunitinib malate), VEGF-Trap, XL184, ZD6474, ATN-161, EMD 121974 (Cilenigtide), Celecoxib, Angiostatin, Endostatin, Regranex, Apligraf, Paclitaxel, tetracyclines, clarithromycin, lasix, captopril, aspirin, Vitamin D3 analogs, retinoids, Imiquomod, Interferon alfa2a, Minocycline, copper peptide containing dressings, Lucentis™, ATG002, Pegaptanib Sodium, Tryptophanyl-tRNA synthetase, squalamine lactate, anecortave acetate, AdPEDF, AG-013958, JSM6427, TG100801, Veglin, ascorbic acid ethers (and their analogs), and Pamidronate.

Anti-cancer agents that can be employed in combination with the compounds of the invention include Taxol™, also referred to as "paclitaxel", is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilization or inhibition of microtubules. Other anti-cancer agents that can be employed in combination with compounds of the invention include Avastin, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide;

bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; inasoprocol; maytansine; mechlorethamine hydrochloride; megestrol acetate; melengestrol acetate; melphalan; menogaril; mercaptopurine; methotrexate; methotrexate sodium; metoprine; meturedepa; initindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be employed in combination with the compounds of the invention include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; anatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimatole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinarnide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A;

placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; virixaltine; vitaxin; vorozole; zanoterone; zeniplatin; zilascorb; and zinostatin stimalamer. Preferred anti-cancer drugs are 5-fluorouracil and leucovorin.

Other chemotherapeutic agents that can be employed in combination with the compounds of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomustine, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with the compounds of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilization or inhibition of microtubules and which can be used in combination with the compounds of the invention include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Haldco), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asia Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-0Y-007 (National Health Research Institutes), and SSR-250411 (Sanofi).

E. Compositions and Methods for Administering Therapies

The present invention provides compositions for the treatment or prevention of angiogenesis related disorders, such as macular degeneration. In a specific embodiment, a composition comprises one or more compounds of the invention, or a pharmaceutically acceptable salt, solvate, clathrate, hydrate or prodrug thereof. In another embodiment, a composition of the invention comprises one or more prophylactic or therapeutic agents other than a compound of the invention, or a pharmaceutically acceptable salt, solvate, clathrate, hydrate, prodrug thereof. In another embodiment, a composition of the invention comprises one or more compounds of the invention, or a pharmaceutically acceptable salt, solvate, clathrate, hydrate or prodrug thereof, and one or more other prophylactic or therapeutic agents. In another embodiment, the composition comprises a compound of the invention, or a pharmaceutically acceptable salt, solvate, clathrate, hydrate, or prodrug thereof, and a pharmaceutically acceptable carrier, diluent or excipient.

In a preferred embodiment, a composition of the invention is a pharmaceutical composition or a single unit dosage form. Pharmaceutical compositions and dosage forms of the invention comprise one or more active ingredients in relative amounts and formulated in such a way that a given pharmaceutical composition or dosage form can be used to treat or prevent angiogenesis related disorders, such as macular degeneration. Preferred pharmaceutical compositions and dosage forms comprise a compound of formula (I), (II), (III), (IV), (V), (VI), (VII), (VIII), (IX), (X), or Table 1, or a pharmaceutically acceptable prodrug, salt, solvate, clathrate, hydrate, or prodrug thereof, optionally in combination with one or more additional active agents.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton, Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmacopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

1) Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton, Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tx.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

2) Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I), (II), (III), (IV), (V), (VI), (VII), (VIII), (IX), (X), or Table 1, or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entirely of which is incorporated herein by reference.

A specific controlled-release formulation of this invention comprises from about 6% to about 40% a compound of formula (I), (II), (III), (IV), (V), (VI), (VII), (VIII), (IX), (X), or Table 1, or a pharmaceutically acceptable salt, solvate, hydrate, clathrate, or prodrug thereof, by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

3) Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4) Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton, Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton, Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone;

various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5) Dosage & Frequency of Administration

The amount of the compound or composition of the invention which will be effective in the prevention, treatment, management, or amelioration of an angiogenesis related disorder, such as macular degeneration, or one or more symptoms thereof, will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases or disorders, as will be readily known by those of ordinary skill in the art. Similarly, amounts sufficient to prevent, manage, treat or ameliorate angiogenesis related disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate angiogenesis related disorders, such as macular degeneration, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate angiogenesis related disorders, such as macular degeneration, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent, treat, manage, or proliferative disorders, such as cancer, or one or more symptoms thereof can be used in the combination therapies of the invention. Preferably, dosages lower than those which have been or are currently being used to prevent, treat, manage, or ameliorate a proliferative disorders, or one or more symptoms thereof, are used in the combination therapies of the invention. The recommended dosages of agents currently used for the prevention, treatment, management, or amelioration of a proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In certain embodiments, when the compounds of the invention are administered in combination with another therapy, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating a proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

F. Other Embodiments

The compounds of the invention may be used as research tools (for example, to evaluate the mechanism of action of new drug agents, to isolate new drug discovery targets using affinity chromatography, as antigens in an ELISA or ELISA-like assay, or as standards in in vitro or in vivo assays). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Example 1

Synthesis of Compound 76

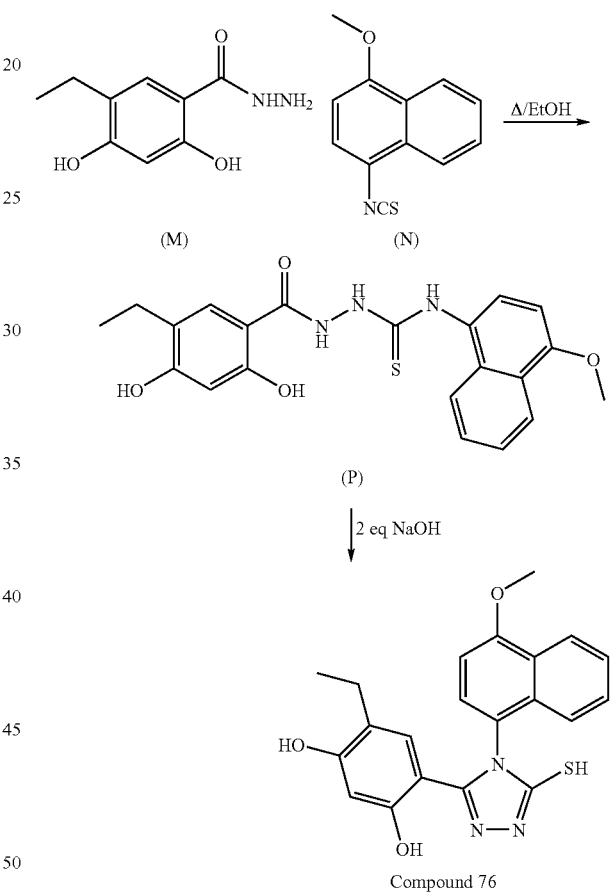

The hydrazide (M) (1.45 g, 7.39 mmol) and the isothiocyanate (N) (1.59 g, 7.39 mmol) were dissolved in ethanol (20 ml) with heating. When the starting materials were dissolved the solution was allowed to cool to room temperature and a precipitate formed. This precipitate was filtered then washed with ether to provide the intermediate (P) as a white solid (2.85 g, 97%). The intermediate (VII) (1.89 g, 4.77 mmol) was heated in a solution of sodium hydroxide (0.38 g, 9.54 mmol) in water (20 mL) at 110° C. for 2 hours. The solution was allowed to cool to room temperature then acidified with conc. HCl. The resulting precipitate was filtered then washed with water (100 mL) and dried. The crude product was recrystallized from ethanol to produce compound 76 as a white solid (1.4 g, 75%).

¹H NMR (DMSO-d₆) δ 9.43-9.53 (bs, 2H),8.11-8.16 (m, 1H), 7.47-7.55 (m, 2H), 7.38 (d, J=8.1 Hz, 1H), 7.31-7.36 (m, 1H), 6.98 (d, J=8.1 Hz, 1H), 6.71 (s, 1H), 6.17 (s, 1H), 3.98 (s, 3H), 2.17 (q, J=7.5 Hz, 2H), 0.73 (t, J=7.5 Hz, 3H);

ESMS calculated for ($C_{21}H_{19}N_3O_3S$) 393.11; Found 394.1 $(M+1)^+$.

Example 2

Synthesis of Compound 124

3-(2,4-Dihydroxy-phenyl)-4-(naphthalen-1-yl)-5-mercapto-triazole (505 mg, 1.5 mmol), which is commercially available from Scientific Exchange, Inc., Center Ossipee, NH 03814, and $Et_3N$ (0.84 ml, 6.0 mmol) in 15 ml $CH_2Cl_2$ were treated dropwise with ethyl isocyanate (360 mg, 5.0 mmol) at 0° C. The mixture was then warmed to room temperature and stirred for 3 h. The reaction mixture was diluted with $CH_2Cl_2$, washed with $H_2O$ and saturated brine, dried with $Na_2SO_4$, and concentrated in vacuo. The residue was chromatographed (Hexane/EtOAc 3:1) to give Compound 124 as a white solid (480 mg, 58%).

¹H-NMR (CDCl₃) δ 10.13 (s, 1H), 7.96 (d, J=9.0 Hz, 2H), 7.61-7.57 (m, 3H), 7.49-7.36(m, 2H), 7.01(s, 1H), 6.88 (d, J=8.4 Hz, 1H), 6.70 (d, J=8.4 Hz, 1H), 4.98-4.96(m, 2H), 3.56(q, J=7.2 Hz, J=12.6 Hz, 2H), 3.28-3.10(m, 4H), 1.33(t, J=7.2 Hz, 3H), 1.13 (q, J=15.0 Hz, J=7.2 Hz, 6H);

ESMS calculated for $C_{27}H_{28}N_6O_5S$: 548.18; Found: 549.1 $(M+1)^+$.

Example 3

Synthesis of Compound 188

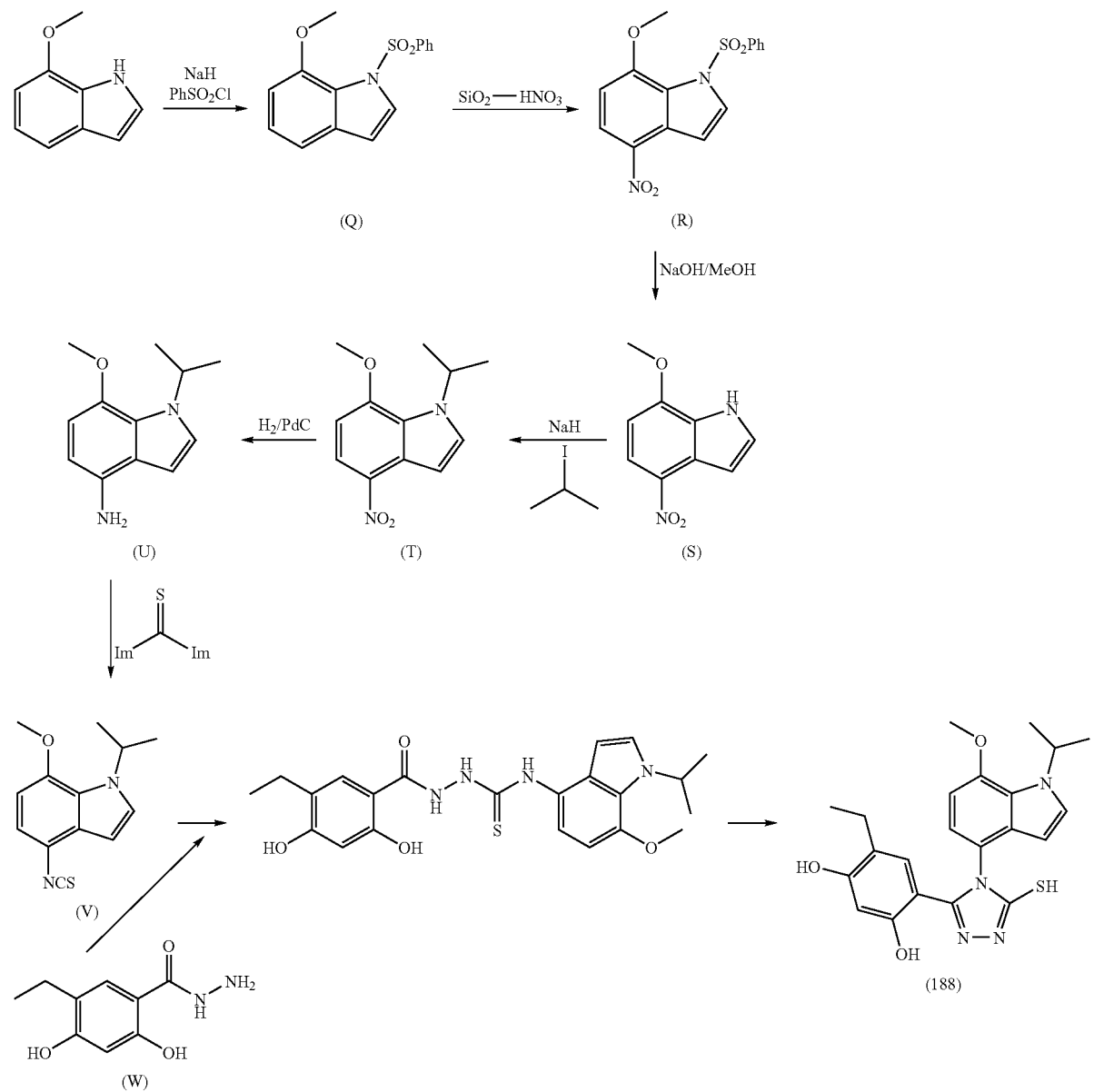

1-Benzenesulfonyl-7-methoxy-1H-indole (Q)

To a solution of 7-methoxyindole (1 eq) in DMF cooled in an ice bath was added NaH (60% dispersion in oil, 1.2 eq). The reaction was stirred for 1 hr at room temperature then recooled in an ice bath. Benzenesulfonyl chloride (1.1 eq) was added then the reaction was stirred for 2 hrs at room temperature. Water/ethyl acetate were added and the ethyl acetate layer was washed repeatedly (3×) with water. The ethyl acetate layer was concentrated and evaporated to dryness.

1-Benzenesulfonyl-7-methoxy-4-nitro-1H-indole (R)

To a solution of 1-benzenesulfonyl-7-methoxy-1H-indole (Q) (1 eq) in dichloromethane cooled in an ice bath was added $SiO_2$—$HNO_3$ (2 wt eq) in small portions. The reaction was stirred for 1 hr at room temperature. Activated carbon (2 wt eq) was added then the entire mixture was stirred for 1 hr. The mixture was then filtered and evaporated to dryness. Separation of the isomers was achieved by column chromatography.

7-Methoxy-4-nitro-1H-indole (S)

To a solution of 1-benzenesulfonyl-7-methoxy-4-nitro-1H-indole (R) (1 eq) in methanol was added a solution of sodium hydroxide (5 eq) in water. The solution was heated to reflux for 3 hrs. Methanol was removed under reduced pressure then water and ethyl acetate were added. The ethyl acetate layer separated and washed repeatedly (3×) with water. The ethyl acetate layer was concentrated and evaporated to dryness to produce the desired product.

1-Isopropyl-7-methoxy-4-nitro-1H-indole (T)

To a solution of 7-methoxy-4-nitro-1H-indole (S) (1 eq) in DMF cooled in an ice bath was added NaH (60% dispersion in oil, 1.2 eq). The reaction was stirred for 1 hr at room temperature then recooled in an ice bath. 2-Iodopropane (1.1 eq) was added then the reaction was stirred for 2 hrs at room temperature. Water and ethyl acetate were added. The ethyl acetate layer was separated and washed repeatedly (3×) with water. The ethyl acetate layer was concentrated then evaporated to dryness. Further purification by column chromatography produced the pure desired product.

1-Isopropyl-7-methoxy-1H-indol-4-ylamine (U)

A solution of 1-isopropyl-7-methoxy-4-nitro-1H-indole (T) (1 eq) and palladium 10% on activated carbon (0.1 wt eq) in methanol/ethyl acetate (1:1) was shaken on a Parr hydrogenation apparatus under hydrogen for 1 hr. The reaction was then filtered through Celite and evaporated to dryness to produce the desired product.

1-Isopropyl-4-isothiocyanato-7-methoxy-1H-indole (V)

To a solution of 1-isopropyl-7-methoxy-1H-indol-4-ylamine (U) (1 eq) in dichloromethane was added 1,1'-thiocarbonyldiimidazole (1.2 eq). The reaction was stirred for 2 hrs at room temperature then evaporated to dryness. Further purification by column chromatography produced the pure desired product.

3-(2,4-Dihydroxy-5-ethyl-phenyl)-4-(1-isopropyl-7-methoxy-indol-4-yl)-5-mercapto-[1,2,4]triazole (Compound 188)

5-Ethyl-2,4-dihydroxy-benzoic acid hydrazide (W) (1 eq) and 1-isopropyl-4-isothiocyanato-7-methoxy-1H-indole (V) (1.01 eq) were heated in ethanol (0.02 M based on isothiocyanate) at 80° C. for 1 hr. The solution was allowed to cool to room temperature overnight. The resulting precipitate was filtered, washed with ether, dried and used without further purification (yield 80%). The precipitate was suspended in aqueous NaOH solution (2 eq NaOH) and nitrogen was bubbled through this suspension for 10 min. The reaction was then heated to 110° C. for 1 hr under a nitrogen atmosphere then allowed to cool to room temperature. Neutralisation with conc. HCl produced a white precipitate which was filtered and washed with water. Repeated recrystallisation from EtOH/water produced the desired product (purity >95%, yield 50-70%)

$^1$H-NMR (DMSO-$d_6$) δ (ppm), 9.52 (s, 1H), 9.42 (s, 1H), 7.40 (d, J=3.3 Hz, 1H), 6.82 (d, J=8.4 Hz, 1H), 6.61 (s, 1H), 6.20 (s, 1H), 6.05 (d, J=3.3 Hz, 1H), 5.30 (qn, J=6.6 Hz, 1H), 3.89 (s, 3H), 2.14 (q, J=7.5 Hz, 2H), 1.41-1.47(m, 6H), 0.68 (t, J=7.5 Hz, 3H);

ESMS CALCULATED. FOR $C_{22}H_{24}N_4O_3S$: 424.16; FOUND: 425.1 $(M+1)^+$.

Example 4

Synthesis of Compound 223

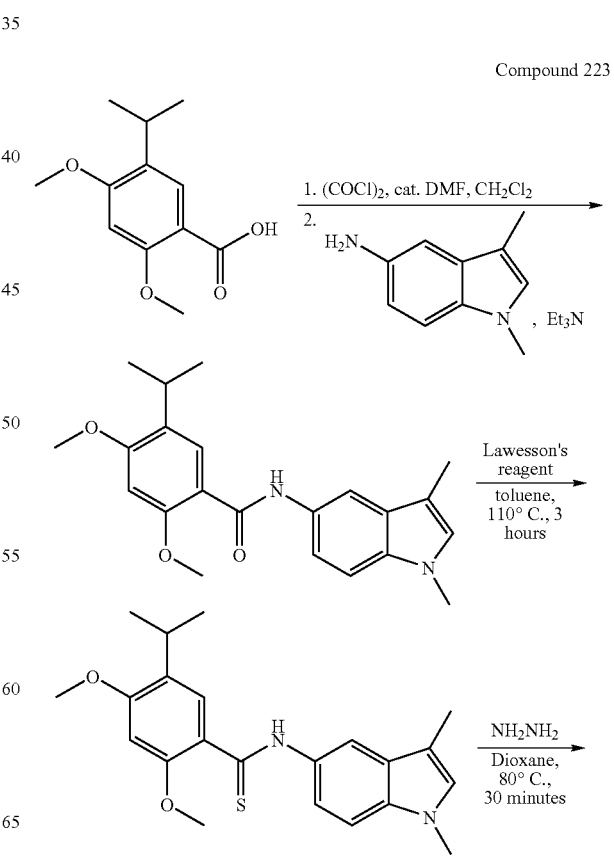

Compound 223

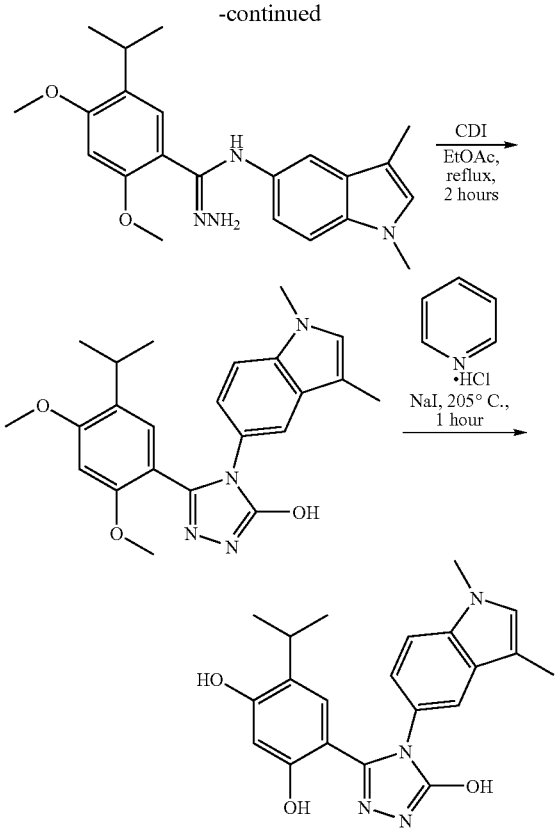

2,4-Dimethoxy-5-isopropylbenzoic acid (2.24 g, 10.0 mmol, 1.00 equiv.) in 50 mL CH$_2$Cl$_2$ at room temperature was treated with (COCl)$_2$ (1.40 g, 11.0 mmol, 1.10 equiv.) and catalytic amount of DMF (0.1 mL) for 1 hour. Solvent and excess (COCl)$_2$ were removed in vacuo. The residue was dissolved in 100 mL CH$_2$Cl$_2$, and treated with 1,3-dimethyl-5-aminoindole (1.60 g, 10.0 mmol, 1.00 equiv.) and triethylamine (1.55 g, 15.0 mmol, 1.50 equiv.) at 0° C. for one hour. Aqueous workup and removal of solvent gave a light brown solid which was washed with ether to yield off-white solid (2.28 g, 6.22 mmol, 62%).

$^1$H NMR (CDCl$_3$) δ (ppm) 9.78 (br s, 1H), 8.21 (s, 1H), 8.09 (d, J=2.1 Hz, 1H), 7.31 (dd, J=8.7 Hz, 2.1 Hz, 1H), 7.22 (d, J=8.7 Hz, 1H), 6.82 (s, 1H), 6.50 (s, 1H), 4.09 (s, 3H), 3.92 (s, 3H), 3.73 (s, 3H), 3.26 (hept, J=6.9 Hz, 1H), 2.32 (s, 3H), 1.24 (d, J=6.9 Hz, 6H).

The off-white solid obtained above was treated with Lawesson's reagent (1.51 g, 3.74 mmol, 0.6 equiv.) in 50 mL toluene at 110° C. for three hours. Toluene was removed on rotary evaporator and vacuum pump, and the residue was treated with hydrazine (anhydrous, 3.0 g, 94 mmol, 15.0 equiv.) in 20 mL dioxane at 80° C. for 30 minutes. The reaction mixture was extracted with ethyl acetate and water to remove excess hydrazine. The organic layer was dried over MgSO$_4$, and filtered to remove drying agent. Carbodiimidazole (CDI) (3.02 g, 18.7 mmol, 3.00 equiv.) was added to the solution, and the solution was refluxed (65° C.) for 2 hours. Solvent was removed, and the residue was treated with 20 mL THF and 10 mL NaOH (2M) to destroy excess CDI. Extraction with ethyl acetate (EtOAc) and water, followed by chromatography purification gave the desired product 3-(2,4-methoxy-5-isopropyl-phenyl)-4-(1,3-dimethyl-indol-5-yl)-5-hydroxy-[1,2,4]triazole as light brown solid (2.20 g, 5.42 mmol, 87%).

$^1$H NMR (CDCl$_3$), δ (ppm) 9.63 (br s, 1H), 7.34 (d, J=2.1 Hz, 1H), 7.20 (s, 1H), 7.18 (d, J=8.4 Hz, 1H), 7.00 (dd, J=8.4 Hz, 2.1 Hz, 1H), 6.80 (s, 1H), 6.19 (s, 1H), 3.76 (s, 3H), 3.69 (s, 3H), 3.40 (s, 3H), 3.15 (hept, J=6.9 Hz, 1H), 2.20 (s, 3H), 1.10 (d, J=6.9 Hz, 6H).

3-(2,4-methoxy-5-isopropyl-phenyl)-4-(1,3-dimethyl-indol-5-yl)-5-hydroxy-[1,2,4]triazole obtained above was treated with pyridine hydrochloride (12.53 g, 108.3 mmol, 20.0 equiv.), NaI (0.812 g, 5.42 mmol, 1.0 equiv.) and 0.5 mL water at 205° C. under nitrogen protection for 1 hour. The reaction mixture was treated with 200 mL water. The solid was collected by filtration, washed with 3×20 mL water, and dissolved in 50 mL 2M NaOH solution. The aqueous solution was extracted with 100 mL EtOAc, and the EtOAc layer was extracted with 2×20 mL 0.5M NaOH. EtOAc layer was discarded. The aqueous layer were combined, neutralized with HCl to PH around 5, and extracted with 3×100 mL EtOAc. The combined EtOAc layer was diluted with 50 mL THF, dried over MgSO$_4$, and filtered through silica gel plug. Most of solvents were removed to form a slurry with around 2 mL of solvent left. Solid was collected by filtration, washed with 2 mL EtOAc, and dried. The desired product 3-(2,4-dihydroxy-5-isopropyl-phenyl)-4-(1,3-dimethyl-indol-5-yl)-5-hydroxy-[1,2,4]triazole (Compound 223) was obtained as an off-white solid (1.75 g, 4.63 mmol, 85%).

$^1$H NMR (CD$_3$OD), δ (ppm) 7.46 (d, J=1.8 Hz, 1H), 7.41 (d, J=8.4 Hz, 1H), 7.04 (dd, J=8.4 Hz, 1.8 Hz, 1H), 7.02 (s, 1H), 6.53 (s, 1H), 6.26 (s, 1H), 3.74 (s, 3H), 2.88 (sept, J=6.9 Hz, 1H), 2.24 (s, 3H), 0.62 (d, J=6.9 Hz, 6H);

ESMS calculated for C$_{21}$H$_{23}$N$_4$O$_3$: 378.1; Found: 379.1 (M+1)$^+$.

The following compounds were prepared as described above in the section entitled "Methods of Making the Compounds of the Invention" and as exemplified in Examples 1 through 4.

Example 5

Compound 1

ESMS calcd for C$_{18}$H$_{13}$N$_3$OS: 319.1; Found: 320.0 (M+1)$^+$.

Example 6

Compound 2

ESMS calcd for C$_{21}$H$_{19}$N$_3$O$_4$S: 409.11; Found: 410.0 (M+H)$^+$.

Example 7

Compound 5

ESMS calcd for C$_{19}$H$_{15}$N$_3$O$_2$S: 365.08; Found: 266.0 (M+H)$^+$.

Example 8

Compound 6

ESMS calcd for C$_{20}$H$_{17}$N$_3$O$_2$S: 379.10; Found: 380.0 (M+H)$^+$.

Example 9

Compound 7

ESMS calcd for $C_{21}H_{19}N_3O_2S$: 393.11; Found: 394.0 (M+H)⁺.

Example 10

Compound 8

ESMS calcd for $C_{21}H_{19}N_3O_3S$: 393.11; Found: 394.0(M+H)⁺.

Example 11

Compound 9

ESMS calcd for $C_{21}H_{19}N_3O_2S$: 393.11; Found: 394.0 (M+H)⁺.

Example 12

Compound 13

¹H-NMR (DMSO-d₆) δ 9.65 (s, 1H), 9.57 (s, 1H), 7.50 (d, J=8.1 Hz, 1H), 7.35 (d, J=3.3 Hz, 1H), 7.14 (t, J=7.8 Hz, 1H), 6.96 (d, J=7.5 Hz, 1H), 6.88 (d, J=8.1 Hz, 1H), 6.09-6.11 (m, 2H), 6.01 (dd, J₁=2.1 Hz, J₂=8.1 Hz, 1H), 4.13-4.22 (m, 2H), 1.36 (t, J=7.2 Hz, 3H);

ESMS calcd for $C_{18}H_{16}N_4O_2S$: 352.10; Found: 353.1 (M+1)⁺.

Example 13

Compound 14

¹NMR (DMSO-d₆) δ 9.72(s, 1H), 9.67(s, 1H), 7.04-7.01 (m, 1H), 6.83-6.78(m, 2H), 6.66-6.63(m, 1H), 6.20-6.19(m, 2H), 4.22(s, 4H);

ESMS calcd for $C_{16}H_{13}N_3O_4S$: 343.06; Found: 344.0 (M+1)⁺.

Example 14

Compound 15

ESMS calcd for $C_{15}H_{13}N_3O_2S$: 299.07; Found: 300.0 (M+H)⁺.

Example 15

Compound 16

ESMS calcd for $C_{15}H_{13}N_3O_2S$: 299.07; Found: 300.0 (M+H)⁺.

Example 16

Compound 17

ESMS calcd for $C_{14}H_{10}ClN_3O_2S$: 319.02; Found: 320.0 (M+H)⁺.

Example 17

Compound 18

ESMS calcd for $C_{14}H_{10}ClN_3O_2S$: 319.02; Found: 320.0 (M+H)⁺.

Example 18

Compound 19

ESMS calcd for $C_{14}H_{10}ClN_3O_2S$: 319.02; Found: 320.1 (M+H)⁺.

Example 19

Compound 20

ESMS calcd for $C_{15}H_{13}N_3O_3S$: 315.07; Found: 316.0 (M+H)⁺.

Example 20

Compound 21

ESMS calcd for $C_{15}H_{13}N_3O_3S$: 315.07; Found: 316.0 (M+H)⁺.

Example 21

Compound 22

ESMS calcd for $C_{15}H_{13}N_3O_3S$: 315.07; Found: 316.0 (M+H)⁺.

Example 22

Compound 23

ESMS calcd for $C_{14}H_{10}FN_3O_2S$: 303.05; Found: 304.0 (M+H)⁺.

Example 23

Compound 23

¹H NMR (DMSO-d₆) δ 9.69 (s, 1H), 9.65 (s, 1H), 7.16 (d, J=7.2 Hz, 1H), 7.05 (t, J=7.2 Hz, 1H), 6.93 (d, J=8.1 Hz, 2H), 6.11-6.16 (m, 2H), 2.21 (s, 3H), 1.89 (s, 3H);

ESMS Calcd $C_{16}H_{15}N_3O_2S$: 313.09, Found 314.1(M+1)⁺.

Example 24

Compound 24

ESMS calcd for $C_{16}H_{15}N_3O_2S$: 313.09; Found: 314.0 (M+H)⁺.

Example 25

Compound 25

¹H NMR (DMSO-d₆) δ 10.44 (m, 1H), 8.00-7.95 (m, 2H), 7.55-7.37 (m, 5H), 6.61 (d, J=7.8 and 1.8 Hz, 1H), 6.51 (t, J=8.6 Hz, 1H), 6.41(d, J=10.8 Hz, 1H);

ESMS calcd for $C_{18}H_{12}FN_3OS$: 337.07; Found: 338.0 (M+1)$^+$.

Example 26

Compound 26

$^1$H NMR (DMSO-d$_6$) δ 9.57 (s, 1H), 7.99 (d, J=8.4 Hz, 1H), 7.96 (d, J=6.9 Hz, 1H), 7.55-7.37 (m, 5H), 6.61 (d, J=8.1 Hz, 1H), 5.83 (d, J=2.1 Hz, 1H), 5.73(dd, J=8.1 and 1.8 Hz, 1H), 5.24 (s, 2H);
ESMS calcd for $C_{18}H_{14}N_4OS$: 334.09; Found: 335.0 (M+1)$^+$.

Example 27

Compound 27

ESMS calcd for $C_{18}H_{19}N_3O_2S$: 341.12; Found: 342.0 (M+H)$^+$.

Example 28

Compound 28

ESMS calcd for $C_{16}H_{15}N_3O_2S$: 313.09; Found: 314.0 (M+H)$^+$.

Example 29

Compound 29

ESMS calcd for $C_{16}H_{15}N_3O_2S$: 313.09; Found: 314.0 (M+H)$^+$.

Example 30

Compound 30

ESMS calcd for $C_{16}H_{15}N_3O_2S$: 313.09; Found: 314.0 (M+H)$^+$.

Example 31

Compound 31

ESMS calcd for $C_{14}H_{10}FN_3O_2S$: 303.05; Found: 304.0 (M+H)$^+$.

Example 32

Compound 32

ESMS calcd for $C_{15}H_{13}N_3O_2S$: 331.04; Found: 332.0 (M+H)$^+$.

Example 33

Compound 33

ESMS calcd for $C_{18}H_{13}N_3O_2S$: 335.07; Found: 336.0 (M+H)$^+$.

Example 34

Compound 34

ESMS calcd for $C_{16}H_{15}N_3O_2S$: 313.09; Found: 314.0 (M+H)$^+$.

Example 35

Compound 35

ESMS calcd for $C_{15}H_{12}FN_3O_2S$: 317.06; Found: 317.0 (M+H)$^+$.

Example 36

Compound 36

ESMS calcd for C20H15N3O2S: 361.1; Found: 362.0 (M+1)$^+$.

Example 37

Compound 37

$^1$H NMR (DMSO-d$_6$) δ 10.03 (s, 1H), 8.00-7.96 (m, 2H), 7.55-7.37 (m, 5H), 7.00 (d, J=8.1 Hz, 1H), 6.20 (m, 2H), 3.57 (s, 3H);
ESMS calcd for $C_{19}H_{15}N_3O_2S$: 349.09; Found: 350.0 (M+1)$^+$.

Example 38

Compound 38

ESMS calcd for $C_{14}H_9Cl_2N_3O_2S$: 352.98; Found: 353.9 (M+H)$^+$.

Example 39

Compound 39

$^1$H NMR (DMSO-d$_6$) δ 9.74 (s, 1H), 9.63 (s, 1H), 8.14 (m, 1H), 7.52-7.48 (m, 2H), 7.37 (d, J=8.4 Hz, 1H), 7.32 (m, 1H), 6.96 (d, =8.1 Hz, 1H), 6.90 (d, =8.4 Hz, 1H), 6.08 (d, =1.9 Hz, 1H), 6.01 (d, =8.4 Hz, 1H), 3.98 (s, 3H);
ESMS calcd for $C_{19}H_{15}N_3O_3S$: 365.08; Found: 366.0 (M+1)$^+$.

Example 40

Compound 40

ESMS calcd for $C_{25}H_{16}N_3O_2S$: 409.09; Found: 410.0 (M+1)$^+$.

Example 41

Compound 42

$^1$H NMR (DMSO-d$_6$) δ 9.75(s, 1H), 9.67(s, 1H), 7.08(s, 2H), 6.96-6.94(m, 2H), 6.18-6.13(m, 2H), 2.72-2.50(m, 3H), 2.35-2.28(m, 1H), 1.64-1.60(m, 4H);
ESMS calcd for $C_{18}H_{17}N_3O_2S$: 339.10; Found: 340.0 (M+1)$^+$.

Example 42

Compound 43

ESMS calcd for $C_{22}H_{15}N_3O_2S$: 385.09; Found: 386.0 (M+1)$^+$.

Example 43

Compound 44

ESMS calcd for $C_{20}H_{15}N_3O_2S$: 361.09; Found: 362.0 (M+1)$^+$.

Example 44

Compound 45

ESMS calcd for $C_{19}H_{15}N_3O_2S$: 349.09; Found: 350.0 (M+1)$^+$.

Example 45

Compound 46

ESMS calcd for $C_{19}H_{21}N_3O_3S$: 371.13; Found: 372.0 (M+1)$^+$.

Example 46

Compound 47

ESMS calcd for $C_{22}H_{27}N_3O_3S$: 413.18; Found: 414.1 (M+1)$^+$.

Example 47

Compound 48

ESMS calcd for $C_{18}H_{12}ClN_3O_2S$: 369.03; Found: 370.0 (M+H)$^+$.

Example 48

Compound 49

$^1$H NMR (DMSO-d$_6$) δ 9.49 (s, 1H), 9.40 (s, 1H), 7.94-7.99 (m, 2H), 7.38-7.56 (m, 5H), 6.70 (s, 1H), 6.13 (s, 1H), 2.12 (q, J=7.2 Hz, 2H), 0.71 (t, J=7.2 Hz, 3H);
ESMS Calcd for $C_{20}H_{17}N_3O_2S$: 363.10, Found 364.1(M+1)$^+$.

Example 49

Compound 50

ESMS calcd for $C_{20}H_{15}N_3O_5S$: 409.07; Found: 410.0 (M+H)$^+$.

Example 50

Compound 51

ESMS calcd for $C_{18}H_{14}N_4O_2S$: 350.08; Found: 351.0 (M+H)$^+$.

Example 51

Compound 52

ESMS calcd for $C_{17}H_{12}N_4OS$: 320.07; Found: 320.9 (M+H)$^+$.

Example 52

Compound 53

$^1$H NMR (CDCl$_3$) δ 12.0 (br s, 1H), 9.87 (br s, 1H), 9.83 (br s, 1H), 7.97 (d, J=8.1 Hz, 2H), 7.41-7.56 (m, 5H), 7.13 (d, J=1.5 Hz, 1H), 7.07 (d, J=8.7 Hz, 1H), 6.71 (dd, J=1.8 Hz, 8.1 Hz, 1H), 1.93 (s, 3H);
ESMS calcd for $C_{20}H_{17}N_4O_2S$: 376.1; Found: 377.0(M+1)$^+$.

Example 53

Compound 56

ESMS calcd for $C_{16}H_{15}N_3O_4S$: 345.08; Found: 346.0 (M+1)$^+$.

Example 54

Compound 57

ESMS calcd for $C_{18}H_{16}N_4O_2S$: 352.10; Found: 353.0 (M+1)$^+$.

Example 55

Compound 61

$^1$H NMR (DMSO-d$_6$) δ 9.66(s, 1H), 9.60(s, 1H), 7.29-7.27 (m, 1H), 7.12-7-10(m, 2H), 7.03-7.00(m, 1H), 6.19-6.17(m, 2H), 1.18(s, 18H);
ESMS calcd for $C_{22}H_{27}N_3O_2S$: 397.18; Found: 398.1 (M+1)$^+$.

Example 56

Compound 64

ESMS calcd for $C_{21}H_{15}N_3O_3S$: 389.08; Found: 390.0 (M+H)$^+$.

Example 57

Compound 65

ESMS calcd for $C_{19}H_{13}N_3O_4S$: 379.06; Found: 380.0 (M+1)$^+$.

Example 58

Compound 66

ESMS calcd for $C_{21}H_{18}N_4O_3S$: 406.11; Found: 407.0 (M+1)$^+$.

Example 59

Compound 67

ESMS calcd for $C_{21}H_{19}N_3O_3S$: 393.11; Found: 394.0 $(M+1)^+$.

Example 60

Compound 68

ESMS calcd for $C_{21}H_{19}N_3O_3S$: 393.11; Found: 394.0 $(M+1)^+$.

Example 61

Compound 69

ESMS calcd for $C_{21}H_{19}N_3O_3S$: 393.11; Found: 394.0 $(M+1)^+$.

Example 62

Compound 70

ESMS calcd for $C_{17}H_{12}N_4O_2S$: 336.07; Found: 337.0 $(M+1)^+$.

Example 63

Compound 71

ESMS calcd for $C_{21}H_{19}N_3O_3S$: 393.11; Found: 394.0 $(M+1)^+$.

Example 64

Compound 72

$^1$H NMR (DMSO-$d_6$) δ 10.3 (br s, 1H), 7.95-8.19 (m, 2H), 7.48-7.72 (m, 5H), 7.17 (d, J=8.4 Hz, 1H), 6.44 (d, J=8.4 Hz, 1H), 5:95 (d, J=2.1 Hz, 1H), 5.73 (dd, J=2.1 Hz, 8.4 Hz, 1H), 5.47 (br s, 1H), 3.62 (s, 3H);
ESMS calcd for $C_{19}H_{17}N_4O_2S_2$: 412.1; Found: 413.0$(M+1)^+$.

Example 65

Compound 73

$^1$H NMR (DMSO-$d_6$) δ 9.37 (s, 1H), 8.94 (s, 1H), 7.94-7.98 (m, 2H), 7.43-7.60 (m, 5H), 5.97 (s, 1H), 1.85 (s, 3H), 1.81 (s, 3H);
ESMS calcd for $C_{20}H_{18}N_3O_2S$: 363.1; Found: 364.0$(M+1)^+$.

Example 66

Compound 74

ESMS calcd for $C_{21}H_{19}N_3O_4S$: 409.11; Found: 410.0 $(M+H)^+$.

Example 67

Compound 75

$^1$H NMR (DMSO-$d_6$) δ 9.46 (s, 1H), 9.45 (s, 1H), 7.95-8.00 (m, 2H), 7.38-7.56 (m, 5H), 6.65 (s, 1H), 6.15 (s, 1H), 2.07-2.14 (m, 2H), 081-1.18 (m, 11H);
ESMS calcd for $C_{24}H_{26}N_3O_2S$: 419.1; Found: 420.1$(M+1)^+$.

Example 68

Compound 76

ESMS calcd for $C_{21}H_{19}N_3O_3S$: 393.11; Found: 394.0 $(M+H)^+$.

Example 69

Compound 77

ESMS calcd for $C_{21}H_{19}N_3O_3S$: 393.11; Found: 394.0 $(M+H)^+$.

Example 70

Compound 78

$^1$H NMR (DMSO-$d_6$) δ 9.71 (s, 1H), 9.35 (s, 1H), 7.98-8.04 (m, 2H), 7.50-7.62 (m, 5H), 6.58 (s, 1H), 2.15 (q, J=7.5 Hz, 2H), 0.58 (t, J=7.5 Hz, 3H);
ESMS calcd for $C_{20}H_{17}ClN_3O_2S$: 397.0; Found: 398.0 $(M+1)^+$.

Example 71

Compound 79

ESMS calcd for $C_{19}H_{21}N_3O_3S$: 371.13; Found: 372.0 $(M+H)^+$.

Example 72

Compound 80

ESMS calcd for $C_{21}H_{19}N_3O_2S$: 393.11; Found: 394.0 $(M+H)^+$.

Example 73

Compound 81

ESMS calcd for $C_{20}H_{17}N_3O_2S$: 379.10; Found: 380.0 $(M+H)^+$.

Example 74

Compound 82

ESMS calcd for $C_{21}H_{19}N_3O_2S$: 393.11; Found: 394.0 $(M+H)^+$.

Example 75

Compound 83

ESMS calcd for $C_{20}H_{17}N_3O_3S$: 379.10; Found: 380.0 $(M+H)^+$.

Example 76

Compound 84

ESMS calcd for $C_{20}H_{17}N_3O_3S$: 379.10; Found: 380.0 $(M+H)^+$.

Example 77

Compound 85

ESMS calcd for $C_{19}H_{15}N_3O_2S$: 365.08; Found: 266.0 $(M+H)^+$.

Example 78

Compound 86

$^1$H NMR (DMSO-$d_6$) δ 9.68 (s, 1H), 9.58 (s, 1H), 8.2 (dd, J=7.0 and 2.4 Hz, 1H), 7.50 (m, 2H), 7.40 (tr, J=8.1 Hz, 1H), 7.32 (m, 1H), 6.97 (d, J=7.5 Hz, 1H), 6.95 (m, 1H), 6.89 (d, = 8.4 Hz, 1H), 6.08 (d, =2.1 Hz, 1H), 6.0 (dd, =7.4 and 2.1 Hz, 1H), 3.96 (s, 3H);
ESMS calcd for $C_{19}H_{15}N_3O_3S$: 365.08; Found: 366.0 $(M+1)^+$.

Example 79

Compound 87

$^1$H NMR (MeOH-$d_4$) δ 8.25 (m, 1H), 7.96 (s, 1H), 7.46-7.44 (m, 2H), 7.26 (d, J=8.4 Hz, 1H), 6.83 (d, J=8.1 Hz, 1H), 6.70 (d, J=8.7 Hz, 1H), 6.17 (d, J=2.1 Hz, 1H), 5.98 (dd, J=8.4 and 2.4 Hz, 1H);
ESMS calcd for $C_{18}H_{13}N_3O_3S$: 351.07; Found: 352.0 $(M+1)^+$.

Example 80

Compound 88

$^1$H-NMR (DMSO-$d_6$) δ 9.69 (s, 1H), 9.59 (s, 1H), 7.54 (d, J=8.1 Hz, 1H), 7.46 (d, J=3 Hz, 1H), 7.14 (t, J=7.8 Hz, 1H), 6.97 (d, J=7.2 Hz, 1H), 6.89 (d, J=8.7 Hz, 1H), 6.12-6.13 (m, 2H), 6.02 (dd, $J_1$=2.4 Hz, $J_2$=8.4 Hz, 1H), 4.74 (qn, J=6.6 Hz, 1H), 1.40-1.46 (m, 6H);
ESMS calcd for $C_{19}H_{18}N_4O_2S$: 366.12; Found: 367.1 $(M+1)^+$.

Example 81

Compound 89

ESMS calcd for $C_{22}H_{21}N_3O_2S$: 391.14; Found: 392.0 $(M+H)^+$.

Example 82

Compound 90

$^1$H NMR (DMSO-$d_6$) δ 9.47 (s, 1H), 9.43 (s, 1H), 7.94-8.00 (m, 2H), 7.39-7.57 (m, 5H), 6.68 (s, 1H), 6.15 (s, 1H), 2.05-2.15 (m, 2H), 1.05-1.17 (m, 2H), 0.50 (t, J=7.5 Hz, 3H);
ESMS calcd for $C_{21}H_{20}N_3O_2S$: 377.1; Found: 378.0$(M+1)^+$.

Example 83

Compound 91

$^1$H NMR (DMSO-$d_6$) δ 9.15 (s, 1H), 8.50 (s, 1H), 8.00-8.07 (m, 2H), 7.47-7.63 (m, 5H), 6.27 (s, 1H), 2.06 (q, J=7.5 Hz, 2H), 1.93 (s, 3H), 0.45 (t, J=7.5 Hz, 3H);
ESMS calcd for $C_{21}H_{20}N_3O_2S$: 377.1; Found: 378.0$(M+1)^+$.

Example 84

Compound 93

ESMS calcd for $C_{16}H_{15}N_3O_4S$: 345.08; Found: 346.0 $(M+H)^+$.

Example 85

Compound 95

ESMS calcd for $C_{16}H_{12}N_4O_2S$: 324.07; Found: 325.0 $(M+H)^+$.

Example 86

Compound 96

ESMS calcd for $C_{19}H_{18}N_4O_3S$: 382.11; Found: 383.0 $(M+H)^+$.

Example 87

Compound 98

ESMS calcd for $C_{17}H_{12}N_4O_2S$: 336.07; Found: 337.0 $(M+H)^+$.

Example 88

Compound 99

ESMS calcd for $C_{19}H_{13}N_3O_4S$: 379.06; Found: 379.9 $(M+H)^+$.

Example 89

Compound 100

$^1$H-NMR (DMSO-$d_6$) δ 9.52 (s, 1H), 9.42 (s, 1H), 7.56 (d, J=8.7 Hz, 1H), 7.49 (d, J=3.3 Hz, 1H), 7.14 (t, J=7.5 Hz, 1H), 6.95 (d, J=8.4 Hz, 1H), 6.61 (s, 1H), 6.21 (s, 1H), 6.14 (dd, J=3.3 Hz, 1H), 4.76 (qn, J=6.6 Hz, 1H), 2.14 (q, J=7.5 Hz, 2H), 1.41-1.47 (m, 6H), 0.66 (t, J=7.5 Hz, 3H);
ESMS calcd for $C_{21}H_{22}N_4O_2S$: 394.15; Found: 395.1 $(M+1)^+$.

Example 90

Compound 101

ESMS calcd for $C_{19}H_{17}N_5O_3S$: 395.11; Found: 396.0 $(M+H)^+$.

Example 91

Compound 102

ESMS calcd. for $C_{19}H_{20}N_5O_2S$: 381.1; Found: 382.0 (M+1)$^+$.

Example 92

Compound 103

$^1$H NMR (DMSO-d$_6$) δ 9.48 (s, 1H), 9.38 (s, 1H), 7.29 (d, J=8.4 Hz, 1H), 7.25 (d, J=1.8 Hz, 1H), 6.85-6.89 (m, 2H), 6.18 (s, 1H), 3.61 (s, 3H), 2.30 (s, 3H), 2.29 (q, J=7.5 Hz, 2H), 2.09 (s, 3H), 0.94 (t, J=7.5 Hz, 3H);
ESMS calcd for $C_{21}H_{23}N_4O_2S$: 394.1; Found: 395.0 (M+1)$^+$.

Example 93

Compound 104

ESMS calcd for $C_{19}H_{15}N_3O_3S$: 365.08; Found: 366.0 (M+H)$^+$.

Example 94

Compound 106

ESMS calcd for $C_{20}H_{17}N_4O_2S$: 377.1; Found: 378.0 (M+H)$^+$.

Example 95

Compound 107

ESMS calcd for $C_{18}H_{13}ClN_3O_2S$: 369.0; Found: 370.0 (M+H)$^+$.

Example 96

Compound 116

$^1$H NMR (DMSO-d$_6$) δ 7.98-7.56 (m, 2H), 7.55-7.30 (m, 6H), 6.43 (dd, J=8.1 and 1.8 Hz, 1H), 6.29 (m, 1H), 3.65 (s, 3H), 3.16 (s, 3H);
ESMS calcd for $C_{20}H_{17}N_3O_2S$: 363.10; Found: 364.0 (M+1)$^+$.

Example 97

Compound 117

$^1$H-NMR (CDCl$_3$) δ 7.83 (d, J=8.1 Hz, 2H), 7.48-7.34 (m, 4H), 7.28-7.20 (m, 1H), 6.99 (d, J=1.8 Hz, 1H), 6.80 (d, J=8.7 Hz, 1H), 6.62-6.58 (m, 1H), 2.94 (s, 3H), 2.89 (s, 3H), 2.84 (s, 3H), 2.81 (s, 3H), 2.75-2.69 (m, 6H);
ESMS calcd for $C_{27}H_{28}N_6O_5S$: 548.18; Found: 549.2 (M+1)$^+$.

Example 98

Compound 122

$^1$H-NMR (CDCl$_3$) δ 7.98 (m, 2H), 7.60-7.55 (m, 3H), 7.51-7.45 (m, 1H), 7.36-7.33 (m, 1H), 6.98-6.97 (m, 1H), 6.86 (d, J=9.9 Hz, 1H), 6.70-6.67 (m, 1H), 2.86 (s, 3H), 2.26 (s, 3H), 2.21 (s, 3H);
ESMS calcd for $C_{24}H_{19}N_3O_5S$: 461.10; Found: 462.0 (M+1)$^+$.

Example 99

Compound 125

ESMS calcd for $C_{20}H_{17}N_3O_3S$: 379.10; Found: 380.0 (M+H)$^+$.

Example 100

Compound 126

ESMS calcd for $C_{10}H_{11}N_3O_2S$: 237.06; Found: 238.0 (M+H)$^+$.

Example 101

Compound 127

ESMS calcd for $C_{11}H_{13}N_3O_2S$: 251.07; Found: 252.0 (M+H)$^+$.

Example 102

Compound 128

ESMS calcd for $C_{11}H_{13}N_3O_2S$: 251.07; Found: 252.0 (M+H)$^+$.

Example 103

Compound 129

ESMS calcd for $C_{11}H_{11}N_3O_2S$: 249.06; Found: 250.0 (M+H)$^+$.

Example 104

Compound 130

ESMS calcd for $C_{12}H_{15}N_3O_2S$: 265.09; Found: 266.0 (M+H)$^+$.

Example 105

Compound 131

ESMS calcd for $C_{20}H_{15}N_3O_4S$: 393.08; Found: 394.1 (M+H)$^+$.

Example 106

Compound 177

$^1$H NMR (DMSO-d$_6$) δ 9.34 (s, 1H), 9.22 (s, 1H), 8.01-7.96 (m, 2H), 7.58-7.44 (m, 5H), 6.56 (s, 1H), 6.14 (s, 1H), 3.29 (s, 3H);
ESMS calcd for $C_{19}H_{15}N_3O_3S$: 365.08; Found: 366.0 (M+1)$^+$.

Example 107

Compound 178

$^1$H NMR (DMSO-d$_6$) δ 10.29 (s, 1H), 9.49 (s, 1H), 9.42 (s, 1H), 8.16 (t, J=5.1 Hz, 1H), 7.45-7.43 (m, 2H), 7.26 (t, J=8.0

Hz, 1H), 6.84 (d, J=7.8 Hz, 1H), 6.75 (d, J=8.7 Hz, 1H), 6.66 (s, 1H), 6.14 (s, 1H), 2.12 (q, J=7.5 Hz, 2H), 0.70 (t, J=7.2 Hz, 3H);

ESMS calcd for $C_{20}H_{17}N_3O_3S$: 379.10; Found: 379.9 $(M+1)^+$.

Example 108

Compound 179

ESMS calcd for $C_{19}H_{15}N_3O_2S$: 349.09; Found: 350.0 $(M+1)^+$.

Example 109

Compound 180

ESMS calcd for $C_{19}H_{15}N_3O_2S$: 349.09; Found: 350.0 $(M+H)^+$.

Example 110

Compound 181

ESMS calcd for C20H15N3O2S: 361.09; Found: 362.0 $(M+H)^+$.

Example 111

Compound 182

ESMS calcd for $C_{16}H_{15}N_3O_3S$: 329.08; Found: 330.0 $(M+H)^+$.

Example 112

Compound 183

ESMS calcd for $C_{20}H_{17}N_3O_2S$: 363.10; Found: 364.0 $(M+H)^+$.

Example 113

Compound 184

ESMS calcd for $C_{18}H_{13}N_3O_3S$: 350.38; Found: 351.9 $(M+H)^+$.

Example 114

Compound 185

ESMS calcd. for $C_{20}H_{21}N_4O_2S$: 380.1; Found: 381.0 $(M+1)^+$.

Example 115

Compound 187

ESMS calcd. for $C_{19}H_{20}N_5O_2S$: 381.1; Found: 382.0 $(M+1)^+$.

Example 116

Compound 190

ESMS CALCD. FOR $C_{21}H_{22}N_4O_2S$: 394.15; FOUND: 395.0 $(M+1)^+$.

Example 117

Compound 191

ESMS calcd. for $C_{22}H_{23}N_4O_4S$: 438.1; Found: 439.0 $(M+1)^+$.

Example 118

Compound 192

ESMS calcd. for $C_{20}H_{22}N_5O_2S$: 395.1; Found: 396.0 $(M+1)^+$.

Example 119

Compound 193

ESMS calcd. for $C_{20}H_{22}N_5O_2S$: 395.1; Found: 396.0 $(M+1)^+$.

Example 120

Compound 194

ESMS calcd. for $C_{23}H_{27}N_4O_2S$: 422.1; Found: 423.0 $(M+1)^+$.

Example 121

Compound 195

ESMS calcd. for $C_{23}H_{25}N_4O_2S$: 420.1; Found: 421.0 $(M+1)^+$.

Example 122

Compound 196

ESMS calcd. for $C_{25}H_{29}N_4O_2S$: 448.1; Found: 449.3 $(M+1)^+$.

Example 123

Compound 197

ESMS calcd. for $C_{22}H_{24}N_4O_2S$: 408.16; Found: 409.2 $(M+1)^+$.

Example 124

Compound 198

ESMS calcd. for $C_{23}H_{26}N_4O_2S$: 422.18; Found: 423.3 $(M+1)^+$.

Example 125

Compound 199

ESMS calcd. for $C_{24}H_{28}N_4O_2S$: 436.19; Found: 437.3 $(M+1)^+$.

Example 126

Compound 200

ESMS calcd. for $C_{22}H_{22}N_4O_2S$: 406.15; Found: 407.2 $(M+1)^+$.

Example 127

Compound 201

ESMS calcd. for $C_{23}H_{24}N_4O_3S$: 436.16; Found: 437.3 $(M+1)^+$.

Example 128

Compound 202

ESMS calcd. for $C_{22}H_{23}N_4O_2S$: 406.1; Found: 407.0 $(M+H)^+$.

Example 129

Compound 204

ESMS calcd. for $C_{24}H_{28}N_4O_3S$: 452.19; Found: 453.2 $(M+1)^+$.

Example 130

Compound 205

ESMS calcd. for $C_{23}H_{24}N_4O_3S$: 436.16; Found: 437.1 $(M+1)^+$.

Example 131

Compound 206

ESMS calcd. for $C_{21}H_{23}N_4O_2S$: 394.1; Found: 395.1 $(M+1)^+$.

Example 132

Compound 207

ESMS calcd. for $C_{20}H_{21}N_4O_2S$: 380.1; Found: 381.1 $(M+1)^+$.

Example 133

Compound 208

ESMS calcd. for $C_{23}H_{26}N_4O_3S$: 438.17; Found: 439.1 $(M+1)^+$.

Example 134

Compound 209

ESMS calcd. for $C_{22}H_{24}N_4O_2S$: 408.1; Found: 409.1 $(M+1)^+$.

Example 135

Compound 210

ESMS calcd. for $C_{24}H_{23}N_4O_2S$: 430.1; Found: 431.1 $(M+1)^+$.

Example 136

Compound 211

ESMS calcd. for $C_{21}H_{22}N_4O_3S$: 410.14; Found: 411.1 $(M+1)^+$.

Example 137

Compound 212

ESMS calcd. for $C_{23}H_{26}N_4O_3S$: 438.17; Found: 439.1 $(M+1)^+$.

Example 138

Compound 213

ESMS calcd. for $C_{20}H_{21}N_4O_2S$: 380.1; Found: 381.1 $(M+1)^+$.

Example 139

Compound 214

ESMS calcd. for $C_{19}H_{19}N_4O_2S$: 366.1; Found: 367.1 $(M+1)^+$.

Example 140

Compound 215

ESMS calcd. for $C_{20}H_{19}N_3O_4S$: 397.1; Found: 398.1 $(M+1)^+$.

Example 141

Compound 216

$^1$H NMR (DMSO-d$_6$): δ (ppm) 9.56 (s, 1H), 9.40 (s, 1H), 8.03 (d, J=2.4 Hz, 1H), 7.58 (d, J=8.4 Hz, 1H), 7.54 (d, J=2.1 Hz, 1H), 7.11 (dd, J=8.4, 2.1 Hz, 1H), 6.97 (d, J=2.4 Hz, 1H), 6.89 (s, 1H), 6.17 (s, 1H), 2.23 (q, J=7.2 Hz, 2H), 0.93 (t, J=7.2 Hz, 3H);

ESMS calcd. for $C_{18}H_{15}N_3O_3S$: 353.08; Found: 354.0 $(M+1)^+$.

Example 142

Compound 217

$^1$H NMR (DMSO-d$_6$): δ (ppm) 9.59 (s, 1H), 9.43 (s, 1H), 7.67 (d, J=8.7 Hz, 1H), 7.54 (d, J=2.1 Hz, 1H), 7.20 (dd, J=8.4, 2.1 Hz, 1H), 6.96 (s, 1H), 6.18 (s, 1H), 2.60 (s, 3H), 2.34 (q, J=7.2 Hz, 2H), 0.98 (t, J=7.2 Hz, 3H);

ESMS calcd. for $C_{18}H_{16}N_4O_3S$: 368.09; Found: 369.0 $(M+1)^+$.

Example 143

Compound 218

ESMS calcd. for $C_{21}H_{23}N_4O_2S$: 394.1; Found: 395.1 $(M+1)^+$.

Example 144

Compound 219

ESMS calcd. for $C_{21}H_{21}N_4O_2S$: 392.1; Found: 393.1 $(M+1)^+$.

Example 145

Compound 220

ESMS calcd. for $C_{20}H_{21}N_4O_3$: 364.1; Found: 365.1 $(M+1)^+$.

Example 146

Compound 221

ESMS calcd. for $C_{20}H_{21}N_4O_2S$: 379.1; Found: 381.1 $(M+1)^+$.

Example 147

Compound 222

ESMS calcd. for $C_{21}H_{23}N_4O_2S$: 394.1; Found: 395.1 $(M+1)^+$.

Example 148

Compound 224

ESMS calcd. for $C_{19}H_{21}N_4O_2S$: 368.1; Found: 369.1 $(M+1)^+$.

Example 149

Compound 225

ESMS calcd. for $C_{19}H_{19}N_4O_2S$: 366.1; Found: 367.1 $(M+1)^+$.

Example 150

Compound 226

ESMS calcd. for $C_{20}H_{21}N_4O_3$: 364.1; Found: 365.1 $(M+1)^+$.

Example 151

Compound 227

ESMS calcd. for $C_{21}H_{22}N_4O_2S$: 394.15; Found: 395.1 $(M+1)^+$.

Example 152

Compound 228

ESMS calcd. for $C_{22}H_{24}N_4O_2S$: 408.16; Found: 409.1 $(M+1)^+$.

Example 153

Compound 229

ESMS calcd. for $C_{20}H_{18}F_3N_5O_2S$: 449.11; Found: 450.1 $(M+1)^+$.

Example 154

Compound 230

ESMS calcd. for $C_{19}H_{19}N_5O_2S$: 381.13; Found: 382.1 $(M+1)^+$.

Example 155

Compound 231

ESMS calcd. for $C_{19}H_{19}N_5O_2S$: 381.13; Found: 382.1 $(M+1)^+$.

Example 156

Compound 232

ESMS calcd. for $C_{22}H_{24}N_4O_3S$: 392.18; Found: 393.1 $(M+1)^+$.

Example 157

Compound 233

ESMS calcd. for $C_{18}H_{17}N_3O_4S$: 371.09; Found: 372.1 $(M+1)+$.

Example 158

Compound 234

ESMS calcd. for $C_{20}H_{21}N_3O_2S$: 367.14; Found: 368.1 $(M+1)+$.

Example 159

Compound 235

ESMS calcd. for $C_{19}H_{19}N_5O_2S$: 381.13; Found: 382.1 $(M+1)^+$.

Example 160

Compound 239

ESMS clcd for $C_{19}H_{21}N_4O_2S$: 368.1; Found: 3.69.1 $(M+H)^+$.

Example 161

Compound 240

ESMS clcd for $C_{18}H_{16}N_4O_3S$: 368.09.10; Found: 369.1 (M+H)⁺.

Example 162

Compound 241

ESMS clcd for $C_{17}H_{15}N_5O_3S$: 369.09; Found: 370.1 (M+H)⁺.

Example 163

Compound 242

ESMS clcd for $C_{19}H_{18}N_4O_3S$: 382.11; Found: 383.1 (M+H)⁺.

Example 164

Compound 243

ESMS clcd for $C_{22}H_{26}N_4O_3S$: 426.17; Found: 427.1 (M+H)⁺.

Example 165

Compound 244

ESMS clcd for $C_{18}H_{16}N_4O_4S$: 384.09; Found: 385.1 (M+H)⁺

Example 166

Compound 245

ESMS clcd for $C_{18}H_{16}N_4O_3S_2$: 400.07; Found: 401.1 (M+H)⁺

Example 167

Compound 245

ESMS clcd for $C_{17}H_{14}N_4O_3S_2$: 386.05; Found: 387.0 (M+H)⁺.

Example 168

Inhibition of HUVEC Cell Migration

Figure 2:
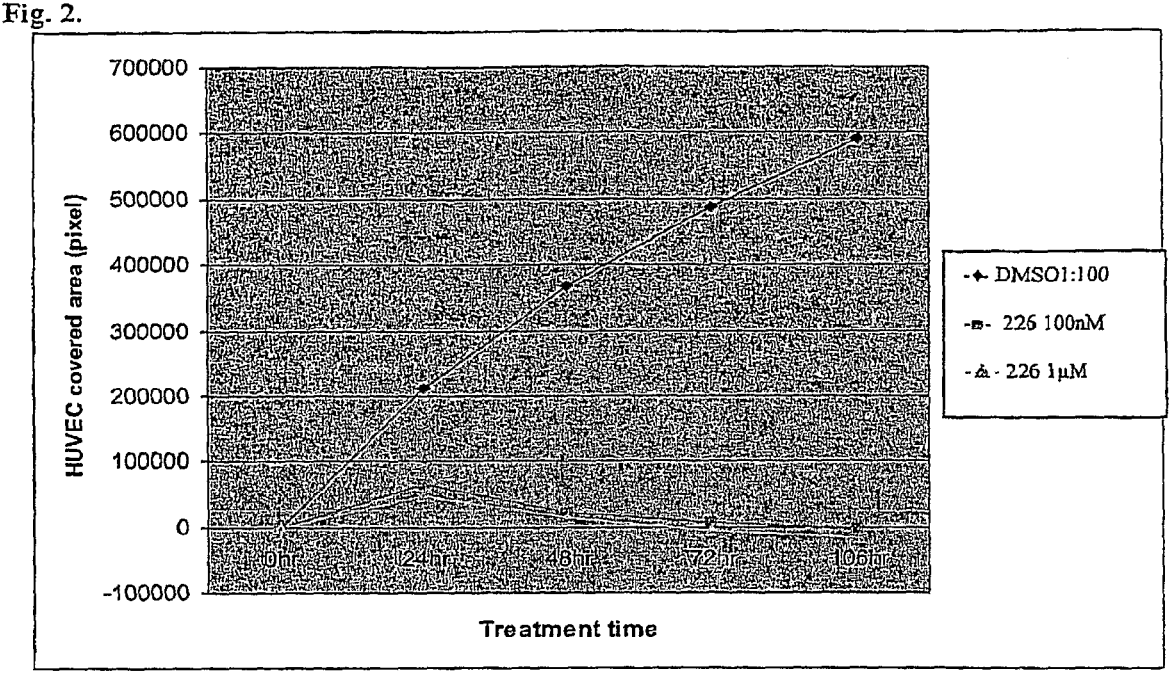
FIG. 2 is a quantification of the effect of Compound 226 on HUVEC migration shown if FIG. 1.
Figure 3:
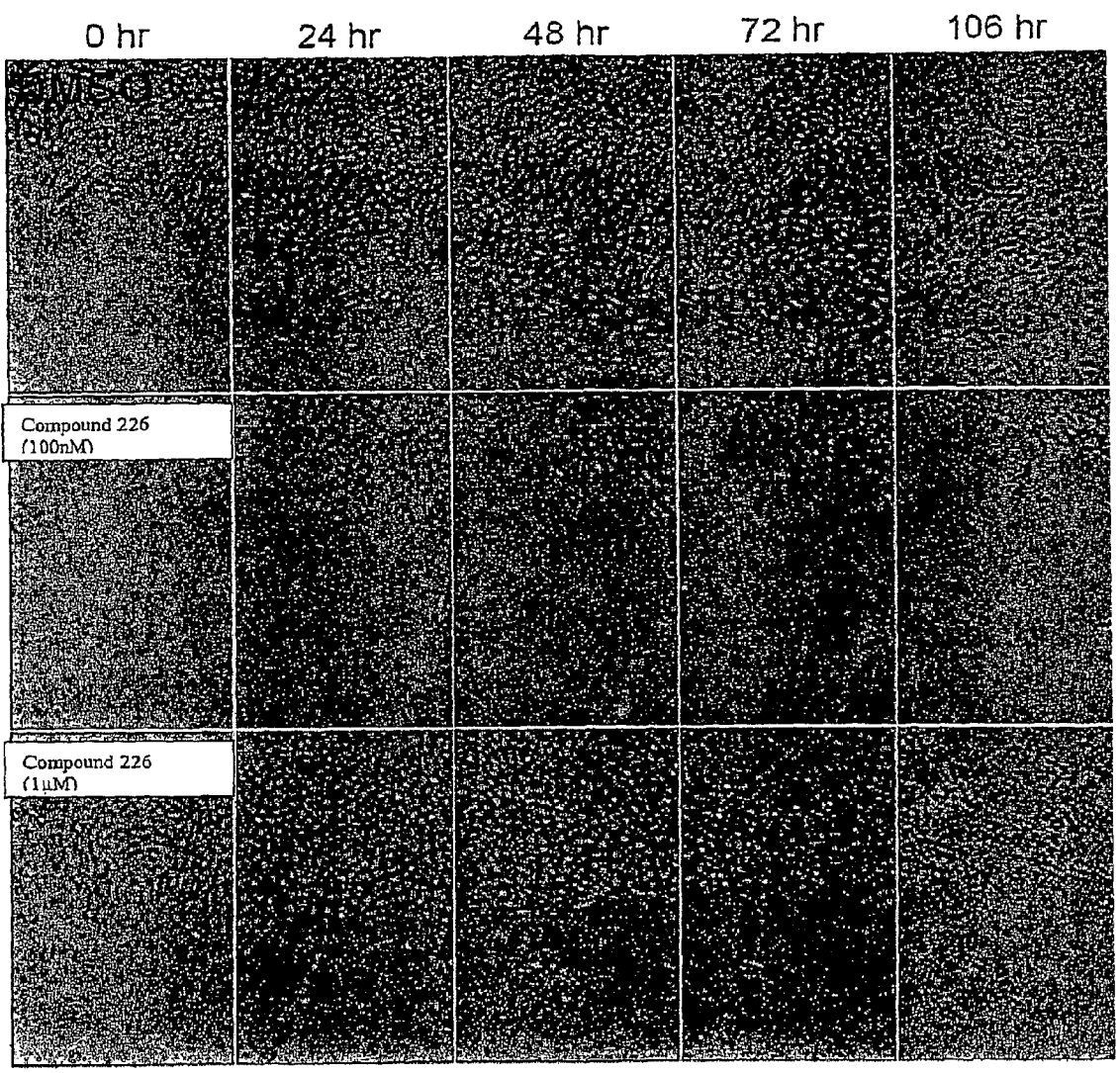
FIG. 3 is a larger magnification of FIG. 1 showing the effect of Compound 226 on HUVEC migration.
Figure 4:
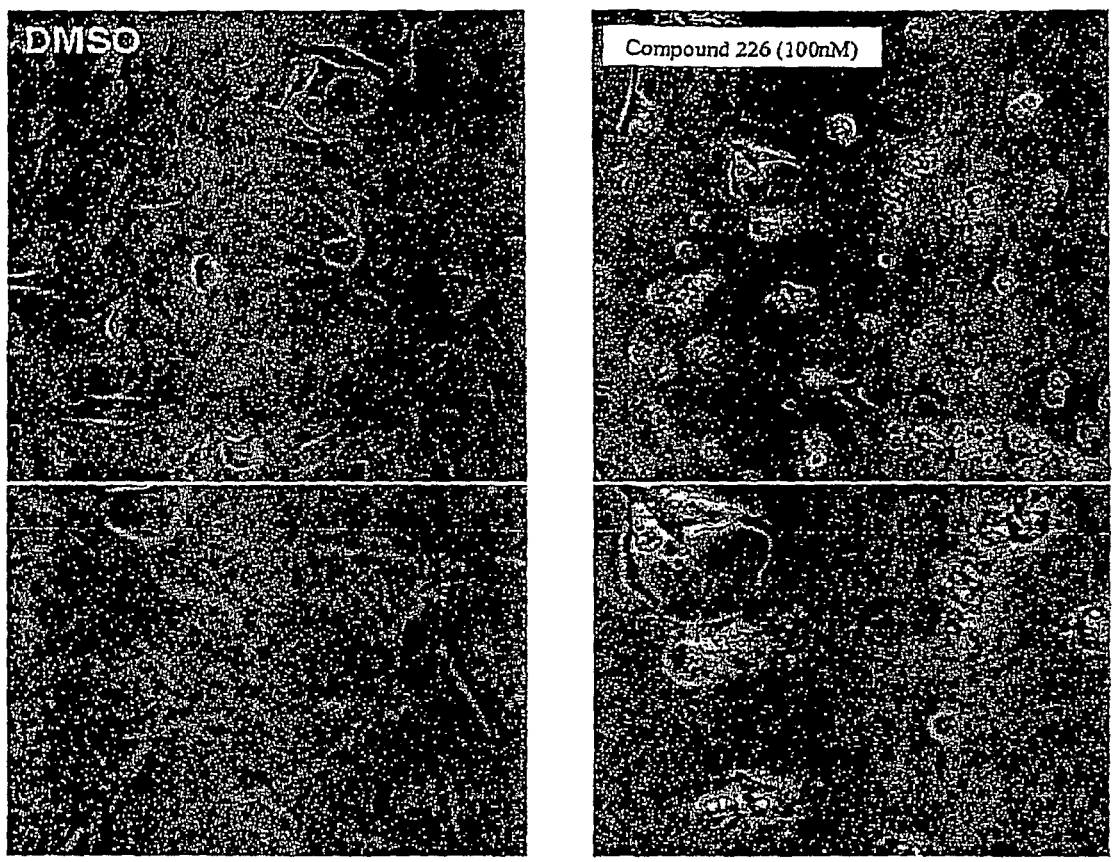
FIG. 4 is an image showing the effect of Compound 226 (100 nM) on HUVEC cell morphology (76 hours after treatment) at 2× and 20× magnification compared to DMSO treated cells.

To examine if the compounds of the invention affect endothelial cell function, an in vitro human umbilical vein endothelial cell (HUVEC) migration assay was performed in the presence of Compound 226. HUVEC cells (ATCC, VA) (passage number 4) were cultured in EGM2 medium (Cambrex, Mass.) on 12-well plates and performed time-lapse imaging with the live cell imaging system on an inverted microscope supplied with 6-7% $CO_2$. The temperature was kept at 37° C. Images were taken every 30 minutes using the 2× objective for up to 106 hr (results in FIGS. 1, 2 and 3), or, every 60 seconds using the 20× objective for 30 min (for FIG. 4). Confluent HUVEC cultures were scraped similarly to make a blank area, followed by culturing in HUVEC medium for 15 hr without treatment. The migration areas, which were imaged as time-lapse sequences for each well, were used as a basis to standardize/correct migration rates. Then, migration of cells under different treatments was imaged at the same time to generate time-lapse image sequences for each well. Time-lapse movies were further analyzed by measuring areas that were covered by migrating cells. FIG. 1 shows cell migration during compound treatment in different time points (0, 24, 48, 72 and 106 hrs). The red lines indicate the front lines of migrating cells. DMSO (1:100) treated cells migrated rapidly and covered the entire blank (wounded) area at 106 hr. However, compared to DMSO, Compound 226 (100 nM and 1 μM) completely blocked migration of HUVEC cells to the blank area. The quantitative analysis of FIG. 1 is shown in FIG. 2. This demonstrates that covered areas were similar between Compound 226, 100 nM and 1 μM treatment, indicating that the IC50 of the inhibition should be below 100 nM. As a reference, a separate experiment was performed and showed that the IC50 of Compound 226 for HUVEC killing was around 800 nM. Images with larger magnification (FIG. 3) showed that no significant cell death was seen at 24 hr, suggesting that the observed migration inhibition was due to the limited motility of HUVEC cells and not due to cell death. During experiments, HUVEC cells were activated by the presence of VEGF (Cambrex, Mass.) and basic FGF (Cambrex, Mass.). Compound 226 possesses potent inhibitory effect on the migration of activated HUVEC cell in vitro induced by VEGF and basic FGF.

In addition to the analysis of HUVEC cell migration, HUVEC behavior was also tracked during above treatments. We found HUVEC cells began to shrink after 24 hr treatment with 100 nM and 1 μM Compound 226. The green arrows in FIG. 2 show that at 48 hr HUVEC cells retracted due to the shrinking of the entire population. However, despite of cell shrinkage, the majority of cells were alive at 48 hr even under 1 μM Compound 226 treatment (see FIG. 3). Careful examination under larger magnification of microscopy (FIG. 4) reveals that HUVEC cells treated with Compound 226 at 100 nM or above appeared to contact to each other tightly. Cell-cell contact lines disappeared in 100 nM Compound 226 treated population in both magnifications in FIG. 4. In time-lapse videos captured with larger magnification objective (20×), significantly reduced movement of HUVEC cells was observed when treated with 100 nM Compound 226, which was distinct from that of DMSO treated cells that moved in rapid speed. These changes of HUVEC cell behavior and morphology suggested that Compound 226 may affect HUVEC cell-cell junction (see Example 169).

Example 169

Compound 226 Enhanced VE-Cadherin Junctions of HUVEC Cells

Figure 5:
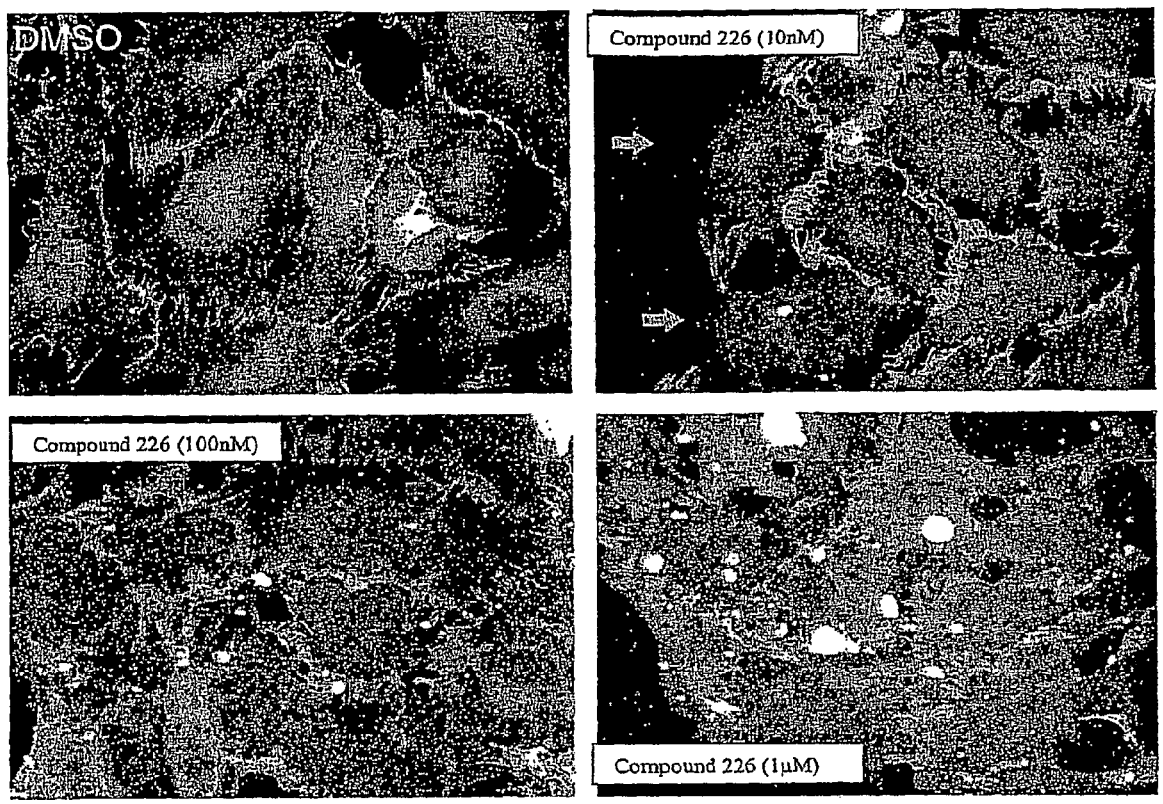
FIG. 5 is an image showing the effect of Compound 226 (10 nM, 100 nM, and 1 µM) on VE-cadherin junction between HUVEC cells in comparison to DMSO treated cells.

An immunofluorescence study was performed by using anti-VE-cadherin antibodies (1:1 mixed, obtained from Amersham Biosciences, NJ, and Santa Cruz Biotechnology, CA) to examine VE-cadherin junctions between HUVEC cells. HUVEC cells were treated with DMSO or Compound 226 (10, 100 and 1000 nM) for 24 hrs and fixed for immunostaining. DMSO concentration was 1:100 for all treatments. To boost the immunofluorescence signal, cells were stained with a mixture of 2 polyclonal anti-human VE-cadherin Abs followed by staining with a mixture of fluorescent secondary antibodies. FIG. 5 shows that VE-cadherin was stained strongly at the cell-cell junctions (red arrows in DMSO), but not the non-contacted regions of cells (green arrows), in the DMSO control. Non-DMSO treated cells gave a similar result to those with DMSO treatment (data not shown). Surprisingly, with 10 nM Compound 226 treatment, VE-cadherin staining was extremely strong in cell-cell junction regions, but not the non-contacted regions (red arrow in Compound 226 10 nM) compared to that in DMSO treated cultures. Increasing the Compound 226 concentration to 100 nM seemed to further increase the VE-cadherin staining areas (red arrows in Compound 226 100 nM). Aggregations of VE-cadherin molecules appeared in wells treated with higher concentration (1 µM). These results strongly suggest that Compound 226 enhances the assembly of cell-cell junctions of activated human endothelial cells, likely through induction of the accumulation of VE-cadherin molecules at the junctions. This effect could result in limited motility of the cells and reducing permeability of the endothelium, thus contributing to the cell migration inhibition and the potential anti-angiogenesis effect of Compound 226.

Example 170

Necrosis in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100× L-glutamine, 1% 100× Penicillin-Streptomycin, 1% 100× sodium pyruvate and 1% 100× MEM non-essential amino acids. FBS is obtained from ATCC and all other reagents are obtained from Invitrogen Corp. (Carlsbad, Calif., USA). Approximately 4-5×10(6) cells that have been cryopreserved in liquid nitrogen are rapidly thawed at 37° C. and transferred to a 175 cm$^2$ tissue culture flask containing 50 ml of growth media and then incubated at 37° C. in a 5% $CO_2$ incubator. The growth media is replaced every 2-3 days until the flask became 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10(6) cells per flask are seeded into 175 cm$^2$ flasks containing 50 ml of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10(6) cells/ml in PBS. Using a 27 gauge needle and 1 cc syringe, 0.1 ml of the cell suspension is injected subcutaneously into the flank of each nude mouse.

Tumors are then permitted to develop in vivo until the majority reached 75-125 mm$^3$ in tumor volume, which typically requires 1 week following implantation. Animals with oblong, very small or large tumors are discarded, and only animals carrying tumors that display consistent growth rates are selected for studies. Tumor volumes (V) are calculated by caliper measurement of the width (W), length (L) and thickness (T) of tumors using the following formula: $V=0.5236 \times (L \times W \times T)$. Animals are randomized into treatment groups so that each group had median tumor volumes of ~100 mm$^3$ at the start of dosing.

To formulate a compound of the invention in DRD, a stock solution of the test article is prepared by dissolving an appropriate amount of the compound in dimethyl sulfoxide (DMSO) by sonication in an ultrasonic water bath. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare a DRD formulation for dosing, the DMSO stock solution is diluted 1:10 with 20% Cremophore RH40. The final DRD formulation for dosing contains 10% DMSO, 18% Cremophore RH40, 3.6% dextrose, 68.4% water and the appropriate amount of test article.

Tumor-bearing animals are given a single intravenous (i.v.) bolus injections of either DRD vehicle or a compound of the invention formulated in DRD, both at 10 mL per kg body weight. Then, 4-24 hr after drug treatment, tumors are excised, cut in half and fixed overnight in 10% neutral-buffered formalin. Each tumor is embedded in paraffin with the cut surfaces placed downwards in the block, and rough cut until a complete section is obtained. From each tumor, 5 µM serial sections are prepared and stained with hematoxylin and eosin. Slides are evaluated manually using light microscopy with a 10×10 square gridded reticle. The percentage of necrosis in a tumor is quantified at 200× magnification by scoring the total number of grid squares containing necrosis and the total number of grid squares containing viable tumor cells.

It is expected that compounds of the invention will result in an increase in necrotic tissue in the center of EMT6 tumors relative to the baseline necrosis observed in vehicle treated tumors. As would be expected for a vascular targeting mechanism of action, rapid onset of necrosis is consistent with there being a loss of blood flow to tumors resulting in hypoxia and tumor cell death.

Example 171

Vascular Disrupting Activities in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100× L-glutamine, 1% 100× Penicillin-Streptomycin, 1% 100× sodium pyruvate and 1% 100× MEM non-essential amino acids. FBS is obtained from ATCC and all other reagents are obtained from Invitrogen Corp. (Carlsbad, Calif., USA). Approximately 4-5×10$^6$ cells that have been cryopreserved in liquid nitrogen are rapidly thawed at 37° C. and transferred to a 175 cm$^2$ tissue culture flask containing 50 mL of growth media and then incubated at 37° C. in a 5% $CO_2$ incubator. The growth media is replaced every 2-3 days until the flask became 90% confluent, typically in 5-7 days. To passage and expand the cell line, a 90% confluent flask is washed with 10 mL of room temperature phosphate buffered saline (PBS) and the cells are disassociated by adding 5 mL 1× Trypsin-EDTA (Invitrogen) and incubating at 37° C. until the cells detach from the surface of the flask. To inactivate the trypsin, 5 mL of growth media is added and then the contents of the flask are centrifuged to pellet the cells. The supernatant is aspirated and the cell pellet is resuspended in 10 mL of growth media and the cell number determined using a hemocytometer. Approximately $1-3 \times 10^6$ cells per flask are seeded into 175 cm² flasks containing 50 mL of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of $10 \times 10^6$ cells/mL in PBS. Using a 27 gauge needle and 1 cc syringe, 0.1 mL of the cell suspension is injected subcutaneously into the flank of each nude mouse.

For the Evans Blue dye assay, tumors are permitted to develop in vivo until the majority reach 40-90 mm³ in tumor volume (to minimize the extent of tumor necrosis), which typically require 4-6 days following implantation. Animals with visibly necrotic, oblong, very small or very large tumors are discarded and only animals carrying tumors that display consistent growth rates are selected for use. Tumor volumes (V) are calculated by caliper measurement of the width (W), length (L) and thickness (T) of tumors using the following formula: $V=0.5236 \times (L \times W \times T)$. Animals are randomized into treatment groups so that at the start of dosing each group have median tumor volumes of ~125 mm³ or ~55 mm³ for the Evans Blue dye assay.

To formulate compounds of the invention for dosing, the appropriate amount of compound is dissolved in 5% dextrose in water (D5W; Abbott Laboratories, North Chicago, Ill., USA). Vehicle-treated animals are dosed with D5W.

To conduct the Evans Blue dye assay, tumor-bearing animals are dosed with vehicle or test article at 0 hr, and then i.v. injected with 100 μL of a 1% (w/v) Evan's Blue dye (Sigma #E-2129; St. Louis, Mo., USA) solution in 0.9%. NaCl at +1 hr. Tumors are excised at +4 hr, weighed and the tissue disassociated by incubation in 50 μL 1 N KOH at 60° C. for 16 hr. To extract the dye, 125 μL of a 0.6 N phosphoric acid and 325 μL acetone are added, and the samples vigorously vortexed and then microcentrifuged at 3000 RPM for 15 min to pellet cell debris. The optical absorbance of 200 μL of supernatant is then measured at 620 nM in a Triad spectrophotometer (Dynex Technologies, Chantilly, Va., USA). Background $OD_{620}$ values from similarly sized groups of vehicle or test article-treated animals that have not been injected with dye are subtracted as background. $OD_{620}$ values are then normalized for tumor weight and dye uptake is calculated relative to vehicle-treated tumors.

To examine the vascular disrupting activity of a compound of the invention, the Evans Blue dye assay is employed as a measurement of tumor blood volume (Graff et al., Eur J Cancer 36:1433-1440, 2000). Evans Blue makes a complex with serum albumin by electrostatic interaction between the sulphonic acid group of the dye and the terminal cationic nitrogens of the lysine residues in albumin. The dye leaves the circulation very slowly, principally by diffusion into extravascular tissues while still bound to albumin. Albumin-dye complex taken up by tumors is located in the extracellular space of non-necrotic tissue, and intracellular uptake and uptake in necrotic regions is negligible. The amount of dye present in a tumor is a measurement of the tumor blood volume and microvessel permeability. Compounds of the invention are expected to result in substantially decreased tumor dye uptake relative to vehicle-treated animals. Such a decrease in dye penetration into the tumor is consistent with there being a loss of blood flow to tumors due to blockage of tumor vasculature, consistent with a vascular disrupting mechanism of action.

All publications, patent applications, patents, and other documents cited herein are incorporated by reference in their entirety. In case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating, reducing or inhibiting a disease associated with angiogenesis in a subject in need thereof, comprising administering to the subject an effective amount of a compound represented by the following structural formula:

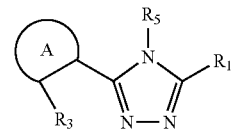

or a tautomer or pharmaceutically acceptable salt thereof, wherein:

ring A is an aryl or a heteroaryl, wherein the aryl or the heteroaryl are optionally further substituted with one or more substituents in addition to $R_3$;

$R_1$ and $R_3$ are, independently, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$OP(O)(OR_7)_2$, or —$SP(O)(OR_7)_2$;

$R_5$ is an optionally substituted heteroaryl or an optionally substituted 8 to 14 membered aryl;

R₇ and R₈, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R₁₀ and R₁₁, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R₁₀ and R₁₁, taken together with the nitrogen to which they are attached, form an optionally substituted heterocyclyl or an optionally substituted heteroaryl;

R₂₆ is a C1-C6 alkyl;

p, for each occurrence, is, independently, 0, 1 or 2; and m, for each occurrence, is independently, 1,2, 3, or 4;

provided that ring A is not a substituted [1,2,3]triazole; and provided that the compound is not 3-(2,4-dihydroxy-phenyl)-4 -(7-naphthalen-1-yl)-5-mercapto-triazole; wherein the disease is selected from ocular neovascular disease; age-related macular degeneration; diabetic retinopathy; retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; marginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment, hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis: ulcerative colitis; Crohn's disease; Bartonellosis; artherosclerosis; Osler-Weber-Rendu-disease; hereditary hemorrhagic telangiectasia; pulmonary hemangiomatosis; pre-eclampsia; endometriosis; fibrosis of the liver and of the kidney; developmental abnormalities (organogenesis); skin discolorations; wound healing; hypertrophic scars; wound granulation; vascular adhesions; cat scratch disease (Rochele ninalia quintosa); ulcers (Helicobacter pylori); keratoconjunctivitis; gingivitis; periodontal disease; epulis; hepatitis; tonsilitis; obesity; rhinitis; laryngitis; tracheitis; bronchitis; bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease.

2. The method of claim 1, wherein R₅ is represented by the following formula:

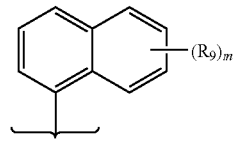

wherein:

R₉, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, or —SP(O)(OR₇)₂;

or two R₉ groups taken together with the carbon atoms to which they are attached form a fused ring; and m is zero or an integer from 1 to 7.

3. The method of claim 1, wherein R₅ is represented by the following structural formula:

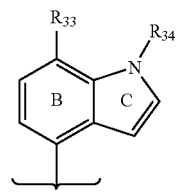

wherein:

R₃₃ is a halo, lower alkyl, a lower alkoxy, a lower haloalkyl, a lower haloalkoxy, and lower alkyl sulfanyl;

R₃₄ is H, a lower alkyl, or a lower alkylcarbonyl; and

Ring B and Ring C are optionally substituted with one or more substituents.

4. The method of claim 1, wherein R₅ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl,an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

5. The method of claim 1, wherein the compound is represented by the following structural formula:

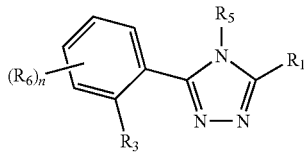

or a tautomer or pharmaceutically acceptable salt thereof, wherein:

$R_6$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, $-NR_{10}R_{11}$, $-OR_7$, $-C(O)R_7$, $-C(O)OR_7$, $-C(S)R_7$, $-C(O)SR_7$, $-C(S)SR_7$, $-C(S)OR_7$, $-C(S)NR_{10}R_{11}$, $-C(NR_8)OR_7$, $-C(NR_8)R_7$, $-C(NR_8)NR_{10}R_{11}$, $-C(NR_8)SR_7$, $-OC(O)R_7$, $-OC(O)OR_7$, $-OC(S)OR_7$, $-OC(NR_8)OR_7$, $-SC(O)R_7$, $-SC(O)OR_7$, $-SC(NR_8)OR_7$, $-OC(S)R_7$, $-SC(S)R_7$, $-SC(S)OR_7$, $-OC(O)NR_{10}R_{11}$, $-OC(S)NR_{10}R_{11}$, $-OC(NR_8)NR_{10}R_{11}$, $-SC(O)NR_{10}R_{11}$, $-SC(NR_8)NR_{10}R_{11}$, $-SC(S)NR_{10}R_{11}$, $-OC(NR_8)R_7$, $-SC(NR_8)R_7$, $-C(O)NR_{10}R_{11}$, $-NR_8C(O)R_7$, $-NR_7C(S)R_7$, $-NR_7C(S)OR_7$, $-NR_7C(NR_8)R_7$, $-NR_7C(O)OR_7$, $-NR_7C(NR_8)OR_7$, $-NR_7C(O)NR_{10}R_{11}$, $-NR_7C(S)NR_{10}R_{11}$, $-NR_7C(NR_8)NR_{10}R_{11}$, $-SR_7$, $-S(O)_pR_7$, $-OS(O)_pR_7$, $-OS(O)_pOR_7$, $-OS(O)_pNR_{10}R_{11}$, $-S(O)_pOR_7$, $-NR_8S(O)_pR_7$, $-NR_7S(O)_pNR_{10}R_{11}$, $-NR_7S(O)_pOR_7$, $-S(O)_pNR_{10}R_{11}$, $-SS(O)_pR_7$, $-SS(O)_pOR_7$, $-SS(O)_pNR_{10}R_{11}$, $-OP(O)(OR_7)_2$, or $-SP(O)(OR_7)_2$; and n is zero of an integer from 1 to 4.

6. A method of treating, reducing or inhibiting a disease associated with angiogenesis in a subject in need thereof, comprising administering to the subject an effective amount of a compound represented by the following structural formula:

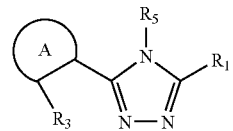

or a tautomer or pharmaceutically acceptable salt thereof,
wherein $R_2$ is a substituted phenyl, wherein the phenyl group is substituted with:
i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxylalkyl, alkoxyalkyl, guanadino, $-NR_{10}R_{11}$, $-O-R_{20}$, $-C(O)R_7$, $-C(O)OR_{20}$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, $-S(O)_pOR_7$, $-OP(O)(OR_7)_2$, or $-SP(O)(OR_7)_2$; or
ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, $-F$, $-Br$, $-I$, cyano, nitro, guanadino, a haloalkyl, a heteroalkyl, $-NR_{10}R_{11}$, $-OR_7$, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, $-OP(O)(OR_7)_2$, or $-SP(O)(OR_7)_2$, $-S(O)_pOR_7$; wherein the disease is selected from ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovulariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin disclolorations; wound healing; hypertrophic scars; wound granulation; vascular adhesions; cat scratch disease (Rochele ninalia quintosa); ulcers (Helicobacter- pylori); keratoconjunctivitis; gingivitis; periodontal disease; epulis; hepatitis; tonsillitis; obesity; rhinitis; laryngitis; tracheitis; bronchitis; bronchiolitis; pneumonia; interstitial pumnonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease.

7. The method of claim 5, wherein the compound is represented by the following structural formula:

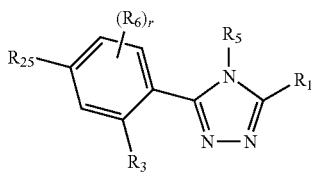

or a tautomer or pharmaceutically acceptable salt thereof, wherein:

$R_{25}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

k is 1, 2, 3, or 4; and
r is zero or an integer from 1 to 3.

8. The method of claim 7 wherein $R_1$, $R_3$ and $R_{25}$ are each independently —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$.

9. The method of claim 7, wherein $R_1$ and $R_3$ are each, independently, —OH, —SH, or —$NHR_7$.

10. The method of claim 9, wherein the compound is represented by the following structural formula:

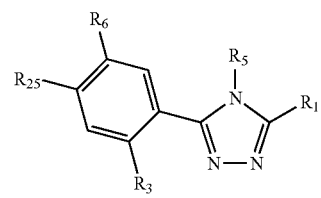

or a tautomer or pharmaceutically acceptable salt thereof;
wherein $R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$.

11. The method of claim 10, wherein:
$R_1$ is —SH or —OH;
$R_3$ and $R_{25}$ are —OH;
$R_6$ is a lower alkyl, C3-C6 cycloalkyl, lower alkoxy, a lower alkyl sulfanyl, or —$NR_{10}R_{11}$; and
$R_9$, for each occurrence, is independently selected from the group consisting of —OH, —SH, halo, a lower haloalkyl, cyano, a lower alkyl, a lower alkoxy, and a lower alkyl sulfanyl.

12. The method of claim 10, wherein $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl, and $R_1$ and $R_3$ are each, independently, —OH, —SH, or —$NHR_7$.

13. The method of claim 12, wherein:
$R_1$ is —SH or —OH;
$R_3$ and $R_{25}$ are —OH;

$R_6$ is a lower alkyl, C3-C6 cycloalkyl, lower alkoxy, a lower alkyl sulfanyl, or —$NR_{10}R_{11}$.

14. The method of claim 1, wherein the compound is selected form the group consisting of:

3-(2-Hydroxyphenyl)-4-(naphthalen-1-yl)-5-mercapto-triazole;
3-(2,4-Dihydroxyphenyl)-4-[4-(2-methoxyethoxy)-naphthalen-1-yl]-5-mercapto-triazole;
3-(2,4-Dihydroxyphenyl)-4-(2-methyl-4-bromophenyl)-5-mercapto-triazole;
3-(3,4-Dihydroxyphenyl)-4-(6-methoxy-naphthalen-1-yl)-5-mercapto-triazole;
3-(3,4-Dihydroxyphenyl)-4-(6-ethoxy-naphthalen-1-yl)-5-mercapto-triazole;
3-(3,4-Dihydroxyphenyl)-4-(6-propoxy-naphthalen-1-yl)-5-mercapto-triazole;
3-(2,4-Dihydroxy-5-ethyl-phenyl)-4-(5-methoxy-naphthalen-1-yl)-5-mercapto-triazole;
3-(3,4-Dihydroxyphenyl)-4-(6-isopropoxy-naphthalen-1-yl)-5-mercapto-triazole;
3-(2,4-Dihydroxyphenyl)-4-(2,6-diethylphenyl)-5-mercapto-triazole;
3-(2,4-Dihydroxyphenyl)-4-(2-methyl-6-ethylphenyl)-5-mercapto-triazole;
3-(2,4-Dihydroxyphenyl)-4-(2,6-diisopropylphenyl)-5-mercapto-triazole;
3-(2,4-Dihydroxyphenyl)-4-(1-ethyl-indol-4-yl)-5-mercapto-triazole;
3-(2,4-Dihydroxyphenyl)-4-(2,3-dihydro-benzo[1,4]dioxin-5-yl)-5-mercapto-triazole;
3-(2,4-Dihydroxyphenyl)-4-(3-methylphenyl)-5-mercapto-triazole;
3-(2,4-Dihydroxyphenyl)-4-(4-methylphenyl)-5-mercapto-triazole;
3-(2,4-Dihydroxyphenyl)-4-(2-Chlorophenyl)-5-mercapto-triazole;
3-(2,4-Dihydroxyphenyl)-4-(3-Chlorophenyl)-5-mercapto-triazole;
3-(2,4-Dihydroxyphenyl)-4-(4-Chlorophenyl)-5-mercapto-triazole;
3-(2,4-Dihydroxyphenyl)-4-(2-methoxyphenyl)-5-mercapto-triazole;
3-(2,4-Dihydroxyphenyl)-4-(3-methoxyphenyl)-5-mercapto-triazole;
3-(2,4-Dihydroxyphenyl)-4-(3-fluorophenyl)-5-mercapto-triazole;
3-(2,4-Dihydroxyphenyl)-4-(2-ethylphenyl)-5-mercapto-triazole;
3-(2-Hydroxy-4-fluorophenyl)-4-(naphthalen-1-yl)-5-mercapto-triazole;
3-(2-Hydroxy-4-aminophenyl)-4-(naphthalen-1-yl)-5-mercapto-triazole;
3-(2,4-Dihydroxyphenyl)-4-(2-methyl-4-butyl-phenyl)-5-mercapto-triazole;
3-(2,4-Dihydroxyphenyl)-4-(2,4-dimethyl-phenyl)-5-mercapto-triazole;
3-(2,4-Dihydroxyphenyl)-4-(2,6-dimethyl-phenyl)-5-mercapto-triazole;
3-(2,4-Dihydroxyphenyl)-4-(2,6-dimethyl-phenyl)-5-mercapto-triazole;
3-(2,4-Dihydroxyphenyl)-4-(4-fluorophenyl)-5-mercapto-triazole;
3-(2,4-Dihydroxyphenyl)-4-(2-methylsulfanylphenyl)-5-mercapto-triazole;
3-(2,4-Dihydroxyphenyl)-4-(naphthalene-2-yl)-5-mercapto-triazole;
3-(2,4-Dihydroxyphenyl)-4-(2,3-dimethylphenyl)-5-mercapto-triazole;
3-(2,4-Dihydroxyphenyl)-4-(2-methyl-4-fluorophenyl)-5-mercapto-triazole;
3-(2,4-Dihydroxyphenyl)-4-(acenaphthalen-5-yl)-5-mercapto-triazole;
3-(2-Hydroxy-4-methoxy-phenyl)-4-(naphthalen-1-yl)-5-mercapto-triazole;
3-(2,4-Dihydroxyphenyl)-4-(2,3-dichlorophenyl)-5-mercapto-triazole;
3-(2,4-Dihydroxyphenyl)-4-(5-methoxynaphthalen-1-yl)-5-mercapto-triazole;
3-(2,4-Dihydroxyphenyl)-4-(pyren-1-yl)-5-mercapto-triazole;
3-(2,4-Dihydroxyphenyl)-4-(quinolin-5-yl)-5-mercapto-triazole;
3-(2,4-Dihydroxyphenyl)-4-(1,2,3,4-tetrahydronaphthalen-5-yl)-5-mercapto-triazole;
3-(2,4-Dihydroxyphenyl)-4-(anthracen-1-yl)-5-mercapto-triazole;
3-(2,4-Dihydroxyphenyl)-4-(biphenyl-2-yl)-5-mercapto-triazole;
3-(2,4-Dihydroxy-6-methyl-phenyl)-4-(naphthalene-1-yl)-5-mercapto-triazole;
3-(2,4-Dihydroxyphenyl)-4-(4-pentyloxyphenyl)-5-mercapto-triazole;
3-(2,4-Dihydroxyphenyl)-4-(4-octyloxyphenyl)-5-mercapto-triazole;
3-(2,4-Dihydroxyphenyl)-4-(4-chloronaphthalen-1-yl)-5-mercapto-triazole;
3-(2,4-Dihydroxy-5-ethyl-phenyl)-4-(naphthalen-1-yl)-5-mercapto-triazole;
3-(2,4-Dihydroxy-5-ethyl-phenyl)-4-(7-carboxymethoxy-naphthalen-1-yl)-5-mercapto-triazole;
3-(2,4-Dihydroxyphenyl)-4-(2-methyl-quinolin-4-yl)-5-mercapto-triazole;
3-(3-Hydroxypyridin-4-yl)-4-(naphthalen-1-yl)-5-mercapto-triazole;
3-(2-Hydroxy-4-acetylamino-phenyl)-4-(naphthalen-1-yl)-5-mercapto-triazole;
3-(2,4-Dihydroxy-phenyl)-4-(1,2,3,4-tetrahydronaphthalen-1-yl)-5-mercapto-triazole;
3-(2,4-Dihydroxy-phenyl)-4-(2,3-dihydro-benzo[1,4]dioxin-5-yl)-5-mercapto-triazole;
3-(2,4-Dihydroxyphenyl)-4-(3,5-dimethoxyphenyl)-5-mercapto-triazole;
3-(2,4-Dihydroxy-phenyl)-4-(2,3-dimethyl-1H-indol-4-yl)-5-mercapto-triazole;
3-(2,4-Dihydroxy-3-propyl-phenyl)-4-(naphthalen-1-yl)-5-mercapto-triazole;
3-(4,6-Dihydroxy-1-ethyl-pyridin-3-yl)-4-(naphthalen-1-yl)-5-mercapto-triazole;
3-(4,6-Dihydroxy-1-methyl-pyridin-3-yl)-4-(naphthalen-1-yl)-5-mercapto-triazole;
3-(2,4-Dihydroxy-phenyl)-4-(3,5-di-tert-butylphenyl)-5-mercapto-triazole;
3-(2,6-Dihydroxy5-fluoro-pyridin-3-yl) 4-(naphthalen-1-yl)-5-mercapto-triazole;
3-(2,4-Dihydroxy-5-methyl-phenyl)-4-(naphthalene-1-yl)-5-mercapto-triazole;
3-[2,4-Dihydroxy-phenyl]-4-(3-benzoylphenyl)-5-mercapto-triazole;
3-(2,4-Dihydroxy-phenyl)-4-(4-carboxy-naphthalen-1-yl)-5-mercapto-triazole;
3-(2,4-Dihydroxy-phenyl)-4-[4-(N,N-dimethylcarbamoyl)-naphthalen-1-yl]-5-mercapto-triazole;

3-(2,4-Dihydroxy-phenyl)-4-(4-propoxy-naphthalen-1-yl)-5-mercapto-triazole;
3-(2,4-Dihydroxy-phenyl)-4-(4-isopropoxy-naphthalen-1-yl)-5-mercapto-triazole;
3-(2,4-Dihydroxy-phenyl)-4-(5-isopropoxy-naphthalen-1-yl)-5-mercapto-triazole;
3-(2,4-Dihydroxy-phenyl)-4-(isoquinolin-5-yl)-5-mercapto-triazole;
3-(2,4-Dihydroxy-phenyl)-4-(5-propoxy-naphthalen-1-yl)-5-mercapto-triazole;
3-(2-Hydroxy-4-methanesulfonamino-phenyl)-4-(naphthalen-1-yl)-5-mercapto-triazole;
3-(2,4-Dihydroxy-3,6-dimethyl-phenyl)-4-(naphthalen-1-yl)-5-mercapto-triazole;
3-(2,4-Dihydroxy-phenyl)-4-[7-(2-methoxyethoxy)-naphthalen-1-yl]-5-mercapto-triazole;
3-(2,4-Dihydroxy-5-hexyl-phenyl)-4-(naphthalen-1-yl)-5-mercapto-triazole;
3-(2,4-Dihydroxy-5-ethyl-phenyl)-4-(4-methoxy-naphthalen-1-yl)-5-mercapto-triazole;
3-(2,4-Dihydroxy-5-ethyl-phenyl)-4-(6-methoxy-naphthalin-1-yl)-5-mercapto-triazole;
3-(2,4-Dihydroxy-3-Chloro-5-ethyl-phenyl)-4-(naphthalen-1-yl)-5-mercapto-triazole;
3-(2,4-Dihydroxy-5-ethyl-phenyl)-4-(2,3-dimethyl-4-methoxy-phenyl)-5-mercapto-triazole;
3-(2,4-Dihydroxy-phenyl)-4-(7-isopropoxy-naphthalen-1-yl)-5-mercapto-triazole;
3-(2,4-Dihydroxy-phenyl)-4-(7-ethoxy-naphthalen-1-yl)-5-mercapto-triazole;
3-(2,4-Dihydroxy-phenyl)-4-(7-propoxy-naphthalen-1-yl)-5-mercapto-triazole;
3-(2-Hydroxy-4-methoxymethyoxy-phenyl)-4-(naphthalen-1-yl)-5-mercapto-triazole;
3-[2-Hydroxy-4-(2-hydroxy-ethoxy)-phenyl]-4-(naphthalen-1-yl)-5-mercapto-triazole;
3-(2,4-Dihydroxyphenyl)-4-(7-methoxy-naphthalen-1-yl)-5-mercapto-triazole;
3-(2,4-Dihydroxyphenyl)-4-(5-methoxy-naphthalen-1-yl)-5-mercapto-triazole;
3-(2,4-Dihydroxyphenyl)-4-(4-hydroxy-naphthalen-1-yl)-5-mercapto-triazole;
3-(2,4-Dihydroxyphenyl)-4-(1-isopropyl-indol-4-yl)-5-mercapto-triazole;
3-(2,4-Dihydroxy-5-tert-butyl-phenyl)-4-(naphthalen-1-yl)-5-mercapto-triazole;
3-(2,4-Dihydroxy-5-propyl-phenyl)-4-(naphthalen-1-yl)-5-mercapto-triazole;
3-(2,4-Dihydroxy-3-methyl-5-ethyl-phenyl)-4-(naphthalen-1-yl)-5-mercapto-triazole;
3-(2,4-Dihydroxy-5-isobutyl-phenyl)-4-(naphthalen-1-yl)-5-mercapto-triazole;
3-(2,4-Dihydroxy-phenyl)-4-(2,3-dimethoxy-phenyl)-5-mercapto-triazole;
3-(2,4-Dihydroxy-phenyl)-4-(2-methoxy-3-Chloro-phenyl)-5-mercapto-triazole;
3-(2,4-Dihydroxy-phenyl)-4-(indol-4-yl)-5-mercapto-triazole;
3-(2,4-Dihydroxy-phenyl)-4-[1-(2-methoxyethoxy)-indol-4-yl]-5-mercapto-triazole;
3-(2,4-Dihydroxy-phenyl)-4-(naphthalen-1-yl)-5-hydroxy-triazole;
3-(1-Oxo-3-hydroxy-pyridin-4-yl)-4-(naphthalen-1-yl)-5-mercapto-triazole;
3-(2,5-Dihydroxy-4-carboxy)-4-(naphthalen-1-yl)-5-mercapto-triazole;
3-(2,4-Dihydroxy-5-ethyl-phenyl)-4-(1-isopropyl-indol-4-yl)-5-mercapto-triazole;
3-(2,4-Dihydroxy-5-ethyl-phenyl)-4-[1-(dimethyl-carbamoyl)-indol-4-yl]-5-mercapto-triazole;
3-(2,4-Dihydroxy-5-ethyl-phenyl)-4-(1-ethyl-benzoimidazol-4-yl)-5-mercapto-triazole;
3-(2,4-Dihydroxy-5-ethyl-phenyl)-4-(1,2,3-trimethyl-indol-5-yl)-5-mercapto-triazole;
3-(2,5-Dihydroxy-4-hydroxymethyl-phenyl)-4-(naphthalen-1-yl)-5-mercapto-triazole;
3-(2-Hydroxy-4-amino-phenyl)-4-(naphthalen-1-yl)-5-mercapto-triazole;
3-(2-Hydroxy-4-acetylamino-phenyl)-4-(naphthalen-1-yl)-5-mercapto-triazole;
3-(2,4-Dihydroxy-3-Chloro-phenyl)-4-(naphthalen-1-yl)-5-mercapto-triazole;
3-(2,4-Dihydroxy-5-ethyl-phenyl)-4-(3-methoxy-phenyl)-5-hydroxy-triazole;
3-(2,4-Dihydroxy-5-ethyl-phenyl)-4-(naphthalen-1-yl)-5-hydroxy-triazole;
3-(2,4-Dihydroxy-5-ethyl-phenyl)-4-(1-isopropyl-indol-3-yl)-5-hydroxy-triazole;
3-(2,4-Dihydroxy-5-ethyl-phenyl)-4-(1-isopropyl-indol-4-yl)-5-amino-triazole;
3-(2,4-Dihydroxy-5-ethyl-phenyl)-4-(3-methoxy-phenyl)-5-amino-triazole;
3-(2,4-Dihydroxy-5-ethyl-phenyl)-4-(naphthalen-1-yl)-5-amino-triazole;
3-(2-Hydroxy-5-ethyloxy-phenyl)-4-(naphthalen-1-yl)-5-hydroxy-triazole;
3-(2-Hydroxy-5-isopropyl-phenyl)-4-(naphthalen-1-yl)-5-hydroxy-triazole;
3-(2-Dihydroxy-phenyl)-4-(7-fluoro-naphthalen-1-yl)-5-hydroxy-triazole;
3-(2,4-Dihydroxy-phenyl)-4-(2,3-difluorophenyl)-5-hydroxy-triazole;
3-(2,4-Dihydroxy-phenyl)-4-[2-(1H-tetrazol-5-yl)-phenyl]-5-hydroxy-triazole;
3-(2,4-Dihydroxy-phenyl)-4-(benzothiazol-4-yl)-5-hydroxy-triazole;
3-(2,4-Dihydroxy-phenyl)-4-(9H-purin-6-yl)-5-hydroxy-triazole;
3-(2,4-Dihydroxy-phenyl)-4-{4-[2-(morpholin-1-yl)-ethoxy]-phenyl}-5-hydroxy-triazole;
3-(2,4-Dihydroxy-phenyl)-4-cyclopentyl-5-hydroxy-triazole;
3-(2,4-Dihydroxy-phenyl)-4-phenyl-5-(sulfamoylamino)-triazole;
3-(2,4-Dihydroxy-5-methoxy-phenyl)-4-(naphthalene-1-yl)-5-ureido-triazole;
3-(2,4-Dihydroxy-5-methoxy-phenyl)-4-(2,3-difluorophenyl)-5-ureido-triazole;
3-(2,4-Dihydroxy-5-ethyl-phenyl)-4-(1-isopropyl-indol-4-yl)-5-ureido-triazole;
3-(2,4-Dihydroxy-5-ethyl-phenyl)-4-(quinolin-5-yl)-5-ureido-triazole;
3-(2,4-Dihydroxy-5-methoxy-phenyl)-4-(naphthalene-1-yl)-5-carbamoyloxy-triazole;
3-(2,4-Dihydroxy-5-ethyl-phenyl)-4-(3-trifluoromethyl-phenyl)-5-carbamoyloxy-triazole;
3-(2,4-Dihydroxy-5-ethyl-phenyl)-4-(1-methyl-indol-4-yl)-5-carbamoyloxy-triazole;
3-(2,4-Dihydroxy-5-methoxy-phenyl)-4-(8-methoxy-quinolin-5-yl)-5-carbamoyloxy-triazole;
3-(2,4-Dihydroxy-5-isopropyl-phenyl)-4-(3-methyl-quinolin-5-yl)-5-carboxyamino-triazole;

3-(2,4-Dihydroxy-phenyl)-4-(1-methyl-2-Chloro-indol-4-yl)-5-carbamoyloxy-triazole;
3-(2,4-Dihydroxy-5-methoxy-phenyl)-4-[3,5-di-(trifluoromethyl)-phenyl]-5-carbamoyloxy-triazole;
3-(2,4-Dihydroxy-5-methoxy-phenyl)-4-(3-trifluoromethyl-phenyl)-5-(sulfamoylamino)-triazole;
3-(2,4-Dihydroxy-5-methoxy-phenyl)-4-(naphthalene-1-yl)-5-(sulfamoylamino)-triazole;
3-(2,4-Dihydroxy-5-methoxy-phenyl)-4-(1-isopropyl-benzoimidazol-4-yl)-5-(sulfamoylamino)-triazole;
3-(2,4-Dihydroxy-5-methoxy-phenyl)-4-(3-isopropylphenyl)-5-(thiocarboxyamino)-triazole;
3-(2,4-Dihydroxy-5-methoxy-phenyl)-4-(3-isopropyloxy-phenyl)-5-(sulfamoyloxy)-triazole;
3-(2,4-Dihydroxy-5-methoxy-phenyl)-4-(naphthalene-1-yl)-5-(sulfamoyloxy)-triazole;
3-(2,4-Dihydroxy-5-methoxy-phenyl)-4-(naphthalen-1-yl)-5-mercapto-triazole;
3-(2,4-Dihydroxy-5-ethyl-phenyl)-4-(5-hydroxy-naphthalen-1-yl)-5-mercapto-triazole;
3-(2,4-Dihydroxy-phenyl)-4-(naphthalen-1-ylmethyl)-5-mercapto-triazole;
3-(2-Hydroxy-4-methoxyphenyl)-4-(naphthalen-1-yl)-5-mercapto-triazole;
3-(2,4-Dihydroxy-phenyl)-4-(biphenyl-3-yl)-5-mercapto-triazole;
3-(2,4-Dihydroxy-phenyl)-4-(2-methyl-5-hydroxymethyl-phenyl)-5-mercapto-triazole;
3-(2,4-Dihydroxy-phenyl)-4-(1-dimethylcarbamoyl-indol-4-yl)-5-mercapto-triazole;
3-(2,4,5-Trihydroxy-phenyl)-4-(naphthalene-1-yl)-5-mercapto-triazole;
3-(2,4-Dihydroxy-5-ethyl-phenyl)-4-(2,3-dimethyl-indol-5-yl)-5-mercapto-triazole;
3-(2,4-Dihydroxy-5-ethyl-phenyl)-4-(3-t-butyl-4-methoxy-phenyl)-5-mercapto-triazole;
3-(2,4-Dihydroxy-5-ethyl-phenyl)-4-(1-ethyl-1H-benzoimidazol-4-yl)-5-mercapto-triazole, HCl salt;
3-(2,4-Dihydroxy-5-ethyl-phenyl)-4-(1-isopropyl-7-methoxy-indol-4-yl)-5-mercapto-triazole; and
3-(2,4-Dihydroxy-5-cyclopropyl-phenyl)-4-(naphthalene-1-yl)-5-mercapto-triazole or a tautomer or pharmaceutically acceptable salt thereof.

15. A method of treating or inhibiting a disease associated with angiogenesis in a subject in need thereof, comprising administering to the subject an effective amount of a compound represented by the following structural formula:

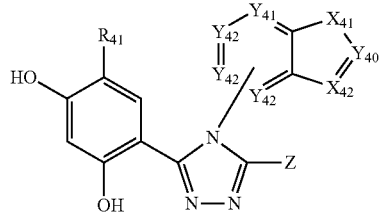

or a tautomer or pharmaceutically acceptable salt thereof, wherein:
$X_{41}$ is O, S, or $NR_{42}$;
$X_{42}$ is $CR_{44}$ or N;
$Y_{40}$ is N or $CR_{43}$;
$Y_{41}$ is N or $CR_{45}$;
$Y_{42}$, for each occurrence, is independently N, C or $CR_{46}$;
Z is OH, SH, or $NHR_7$;

$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NIZ_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$,

—NR₇C(S)R₇, —OC(S)OR₇, —SC(S)OR₇, —NR₇C(S)OR₇, —OC(S)NR₁₀R₁₁, —SC(S)NR₁₀R₁₁, —NR₇C(S)NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, or —NR₇C(NR₈)NR₁₀R₁₁;

R₄₆, for each occurrence, is independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁;

R₇ and R₈, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R₁₀ and R₁₁, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R₁₀ and R₁₁, taken together with the nitrogen to which they are attached, form an optionally substituted heterocyclyl or an optionally substituted heteroaryl;

R₂₆, for each occurrence is, is independently, a lower alkyl; p, for each occurrence, is, independently, 1 or 2; and m, for each occurrence, is, independently, 1, 2, 3, or 4; wherein the disease is selected from ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency, contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial Ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vritritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis ulcerative colitis; Crohn's disease; Bartonellosis; atherosclerosis; Osler-Weber- Rendu disease; hereditary hernoniagictelangiectasia; pulmonary heniangiomatosis; pre- eclampsia; endometriosis; fibrosis of the liver and of the kidney; developmental abnormalities, (organogenesis); skin discolorations; wound healing; hypertrophic scars; wound granulation; vascular adhesions; cat scratch disease (Rochele ninalia quintosa); ulcers (Helicohacter pylori); keratoconjunctivitis; gingivitis; periodontal disease; epulis; hepatitis; tonsillitis; obesity; rhinitis; laryngitis; tracheitis; bronchitis; bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease.

16. The method of claim 15, wherein $X_{41}$ is $NR_{42}$ and $X_{42}$ is $CR_{44}$.

17. The method of claim 15, wherein $X_{41}$ is $NR_{42}$, and $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH₂)ₘC(O)OH, —CH₂OCH₃, —CH₂CH₂OCH₃, and —C(O)N(CH₃)₂.

18. The method of claim 15, wherein $R_{43}$ and $R_{44}$ are, independently, selected from the group consisting of —H, methyl, ethyl, propyl, isopropyl, cyclopropyl, methoxy, ethoxy, propoxy, and cyclopropoxy; and Z is —OH or —SH.

19. The method of claim 15, wherein the compound is selected from the group consisting of:
3-(2,4-dihydroxy-5-ethyl-phenyl)-4-(2-methyl-7-methoxy-benzofuran-4-yl)-5-mercapto-[1,2,4]triazole,
3-(2,4-dihydroxy-5-ethyl-phenyl)-4-(benzofuran-5-yl)-5-mercapto-[1,2,4]triazole, and
3-(2,4-dihydroxy-5-ethyl-phenyl)-4-(2-methyl-1,3-benzoxaz-5-yl)-5-mercapto-[1,2,4]triazole.

20. The method of claim 15 wherein the compound is represented by the following structural formula:

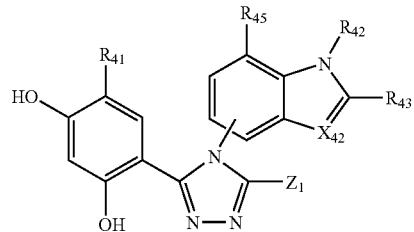

or a tautomer or pharmaceutically acceptable salt thereof, wherein $Z_1$ is —OH or —SH.

21. The method of claim 20, wherein $X_{42}$ is $CR_{44}$, and $R_{43}$ and $R_{44}$ are, independently, selected from the group consisting of —H, methyl, ethyl, propyl, isopropyl, cyclopropyl, methoxy, ethoxy, propoxy, and cyclopropoxy.

22. The method of claim 20, wherein:
$X_{45}$ is $CR_{54}$ or N;
$R_{56}$ is selected from the group consisting of —H, methyl, ethyl, isopropyl, and cyclopropyl;
$R_{52}$ is selected from the group consisting of —H, methyl, ethyl, n-propyl, isopropyl, n-butyl, n-pentyl, n-hexyl, —(CH₂)₂OCH₃, —CH₂C(O)OH, and —C(O)N(CH₃)₂;

$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring; and $R_{55}$ is selected from the group consisting of —H, —OH, —OCH$_3$, and —OCH$_2$CH$_3$.

23. The method of claim 15, wherein the compound is selected from the group consisting of:
- 3-(2,4-dihydroxy-5-ethyl-phenyl)-4-(1,3-dimethyl-indol-5-yl)-5-hydroxy-[1,2,4]triazole,
- 3-(2,4-dihydroxy-5-isopropyl-phenyl)-4-(1,3-dimethyl-indol-5-yl)-5-hydroxy-[1,2,4]triazole,
- 3-(2,4-dihydroxy-5-isopropyl-phenyl)-4-(1-methyl-indol-5-yl)-5-hydroxy-[1,2,4]triazole,
- 3-(2,4-dihydroxy-5-isopropyl-phenyl)-4-(1-isopropyl-indol-4-yl)-5-hydroxy-[1,2,4]triazole;
- 3-(2,4-dihydroxy-5-isopropyl-phenyl)-4-(1-methyl-indazol-5-yl)-5-mercapto-[1,2,4]triazole;
- 3-(2,4-dihydroxy-5-isopropyl-phenyl)-4-(1-methyl-indazol-6-yl)-5-mercapto-[1,2,4]triazole;
- 3-(2,4-dihydroxyphenyl)-4-(1-ethyl-indol-4-yl)-5-mercapto-[1,2,4]triazole,
- 3-(2,4-dihydroxyphenyl)-4-(1-isopropyl-indol-4-yl)-5-mercapto-[1,2,4]triazole,
- 3-(2,4-dihydroxyphenyl)-4-(indol-4-yl)-5-mercapto-[1,2,4]triazole,
- 3-(2,4-dihydroxyphenyl)-4-(1-methoxyethyl-indol-4-yl)-5-mercapto-[1,2,4]triazole,
- 3-(2,4-dihydroxy-5-ethyl-phenyl)-4-(1-isopropyl-indol-4-yl)-5-mercapto-[1,2,4]triazole,
- 3-(2,4-dihydroxyphenyl)-4-(1-dimethylcarbamoyl-indol-4-yl)-5-mercapto-[1,2,4]triazole,
- 3-(2,4-dihydroxy-5-ethylphenyl)-4-(1-propyl-indol-4-yl)-5-mercapto-[1,2,4]triazole,
- 3-(2,4-dihydroxy-5-ethyl-phenyl)-4-(1,2,3-trimethyl-indol-5-yl)-5-mercapto-[1,2,4]triazole,
- 3-(2,4-dihydroxy-5-ethyl-phenyl)-4-(2,3-dimethyl-indol-5-yl)-5-mercapto-[1,2,4]triazole,
- 3-(2,4-dihydroxy-5-ethyl-phenyl)-4-(1-acetyl-2,3-dimethyl-indol-5-yl)-5-mercapto-[1,2,4]triazole,
- 3-(2,4-dihydroxy-5-ethyl-phenyl)-4-(1-isopropyl-7-methoxy-indol-4-yl)-5-mercapto-[1,2,4]triazole,
- 3-(2,4-dihydroxy-5-ethyl-phenyl)-4-(1-propyl-2,3-dimethyl-indol-5-yl)-5-mercapto-[1,2,4]triazole,
- 3-(2,4-dihydroxy-5-ethyl-phenyl)-4-(N-methyl-tetrahydrocarbozol-7-yl)-5-mercapto-[1,2,4]triazole,
- 3-(2,4-dihydroxy-5-ethyl-phenyl)-4-(N-methyl-cyclononan[a]indol-5-yl)-5-mercapto-[1,2,4]triazole,
- 3-(2,4-dihydroxy-5-ethyl-phenyl)-4-(1-n-butyl-indol-4-yl)-5-mercapto-[1,2,4]triazole,
- 3-(2,4-dihydroxy-5-ethyl-phenyl)-4-(1-n-pentyl-indol-4-yl)-5-mercapto-[1,2,4]triazole,
- 3-(2,4-dihydroxy-5-ethyl-phenyl)-4-(1-n-hexyl-indol-4-yl)-5-mercapto-[1,2,4]triazole,
- 3-(2,4-dihydroxy-5-cyclopropyl-phenyl)-4-(1-(1-methyl-cyclopropyl)-indol-4-yl)-5-mercapto-[1,2,4]triazole,
- 3-(2,4-dihydroxy-5-cyclopropyl-phenyl)-4-(1-isopropyl-7-methoxy-indol-4-yl)-5-mercapto-[1,2,4]triazole,
- 3-(2,4-dihydroxy-5-cyclopropyl-phenyl)-4-(1,2,3-trimethyl-indol-5-yl)-5-mercapto-[1,2,4]triazole,
- 3-(2,4-dihydroxy-5-ethyl-phenyl)-4-(1-isopropyl-7-methoxy-indol-4-yl)-5-mercapto-[1,2,4]triazole disodium salt,
- 3-(2,4-dihydroxy-5-tert-butyl-phenyl)-4-(1-isopropyl-7-methoxy-indol-4-yl)-5-mercapto-[1,2,4]triazole,
- 3-(2,4-dihydroxy-5-cyclopropyl-phenyl)-4-(1-propyl-7-methoxy-indol-4-yl)-5-mercapto-[1,2,4]triazole,
- 3-(2,4-dihydroxy-5-ethyl-phenyl)-4-(1-methyl-3-ethyl-indol-5-yl)-5-mercapto-[1,2,4]triazole,
- 3-(2,4-dihydroxy-5-ethyl-phenyl)-4-(1,3-dimethyl-indol-5-yl)-5-mercapto-[1,2,4]triazole,
- 3-(2,4-dihydroxy-5-isopropyl-phenyl)-4-(1-isopropyl-7-methoxy-indol-4-yl)-5-mercapto-[1,2,4]triazole,
- 3-(2,4-dihydroxy-5-ethyl-phenyl)-4-(1-methyl-3-isopropyl-indol-5-yl)-5-mercapto-[1,2,4]triazole,
- 3-(2,4-dihydroxy-5-ethyl-phenyl)-4-(N-ethyl-carbozol-7-yl)-5-mercapto-[1,2,4]triazole,
- 3-(2,4-dihydroxy-5-ethyl-phenyl)-4-(1-isopropyl-7-hydroxy-indol-4-yl)-5-mercapto-[1,2,4]triazole,
- 3-(2,4-dihydroxy-5-ethyl-phenyl)-4-(1-isopropyl-7-ethoxy-indol-4-yl)-5-mercapto-[1,2,4]triazole,
- 3-(2,4-dihydroxy-5-ethyl-phenyl)-4-(1,2-dimethyl-indol-5-yl)-5-mercapto-[1,2,4]triazole,
- 3-(2,4-dihydroxy-5-ethyl-phenyl)-4-(N-methyl-indol-5-yl)-5-mercapto-[1,2,4]triazole,
- 3-(2,4-dihydroxy-5-isopropyl-phenyl)-4-(1,3-dimethyl-indol-5-yl)-5-mercapto-[1,2,4]triazole,
- 3-(2,4-dihydroxy-5-cyclopropyl-phenyl)-4-(1,3-dimethyl-indol-5-yl)-5-mercapto-[1,2,4]triazole,
- 3-(2,4-dihydroxy-5-cyclopropyl-phenyl)-4-(1-methyl-indol-5-yl)-5-mercapto-[1,2,4]triazole,
- 3-(2,4-dihydroxy-5-isopropyl-phenyl)-4-(1H-indol-5-yl)-5-mercapto-[1,2,4]triazole,
- 3-(2,4-dihydroxy-5-ethyl-phenyl)-4-(1,2-dimethyl-indol-5-yl)-5-mercapto-[1,2,4]triazole,
- 3-(2,4-dihydroxy-5-isopropyl-phenyl)-4-(1-ethyl-indol-5-yl)-5-mercapto-[1,2,4]triazole,
- 3-(2,4-dihydroxy-5-isopropyl-phenyl)-4-(1-propyl-indol-5-yl)-5-mercapto-[1,2,4]triazole,
- 3-(2,4-dihydroxy-5-ethyl-phenyl)-4-(1-ethyl-benzimidazol-4-yl)-5-mercapto-[1,2,4]triazole,
- 3-(2,4-dihydroxy-5-ethyl-phenyl)-4-(1-ethyl-benzimidazol-4-yl)-5-mercapto-[1,2,4]triazole HCL salt,
- 3-(2,4-dihydroxy-5-ethyl-phenyl)-4-(2-methyl-3-ethyl-benzimidazol-5-yl)-5-mercapto-[1,2,4]triazole,
- 3-(2,4-dihydroxy-5-ethyl-phenyl)-4-(1-ethyl-2-methyl-benzimidazol-5-yl)-5-mercapto-[1,2,4]triazole,
- 3-(2,4-dihydroxy-5-isopropyl-phenyl)-4-(1-methyl-2-trifluoromethyl-benzimidazol-5-yl)-5-mercapto-[1,2,4]triazole; and
- 3-(2,4-dihydroxy-5-isopropyl-phenyl)-4-(N-methyl-indol-5-yl)-5-mercapto-[1,2,4]triazole;

or tautomers or pharmaceutically acceptable salts thereof.

24. A method of blocking, occluding, or otherwise disrupting blood flow in a disease associated with neovasculature, comprising contacting the neovasculature with an effective amount of a compound represented by the following structural formula:

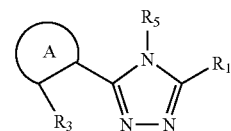

or a tautomer or pharmaceutically acceptable salt thereof, wherein:

ring A is an aryl or a heteroaryl, wherein the aryl or the heteroaryl are optionally further substituted with one or more substituents in addition to $R_3$;

$R_1$ and $R_3$ are, independently, —OH, —SH, —NR$_7$H, —OR$_{26}$, —SR$_{26}$, —NHR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_5$ is an optionally substituted heteroaryl or an optionally substituted 8 to 14 membered aryl;

R$_7$ and R$_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a C1-C6 alkyl;

p, for each occurrence, is, independently, 0, 1 or 2; and m, for each occurrence, is independently, 1, 2, 3, or 4;

provided that ring A is not a substituted [1,2,3]triazole; and provided that the compound is not 3-(2,4-dihydroxy-phenyl)-4-(7-naphthalen-1-yl)-5-mercapto-triazole, wherein the neovasculature is in a subject in need of treatment to block, occlude or otherwise disrupt blood flow in the neovasculature; wherein the disease is selected from infectious diseases; autoimmune disorders; benign tumors; artheroscleric plaques; ocular angiogenic diseases; rheumatoid arthritis; psoriasis; warts; allergic dermatitis; blistering disease; Katposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; HHT; transplant arteriopathy; restinosis; obesity; myocardial angiogenesis; coronary collaterals; cerebral collaterals; arteriovenous malformations; ischemic limb angiogenesis; primary pulmonary hypertension; pulmonary edema; asthma; nasal polyps; inflammatory bowel disease; periodontal disease; ascites; peritoneal adhesions; Osler-Webber Syndrome; plaque neovascularization; telangiectasia; hemophiliac joints; synovitis; osteomyelitis; osteophyte formation; angiofibroma; fibromuscular dysplasia; wound granulation; Crohn's disease; and atherosclerosis.

25. The method of claim 24, wherein R$_5$ is represented by the following formula:

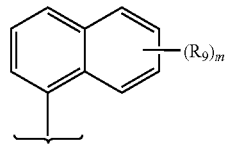

wherein:

R$_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanadino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, or —SP(O)(OR$_7$)$_2$;

or two R$_9$ groups taken together with the carbon atoms to which they are attached form a fused ring; and m is zero or an integer from 1 to 7.

26. The method of claim 24, wherein R$_5$ is represented by the following structural formula:

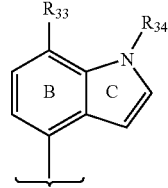

wherein:

R$_{33}$ is a halo, lower alkyl, a lower alkoxy, a lower haloalkyl, a lower haloalkoxy, and lower alkyl sulfanyl;

R$_{34}$ is H, a lower alkyl, or a lower alkylcarbonyl; and

Ring B and Ring C are optionally substituted with one or more substituents.

27. The method of claim 24, wherein R$_5$ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b] pyridinyl, an optionally substituted 1H-imidazo[4,5-c] pyridinyl, an optionally substituted 3H-imidazo[4,5-c] pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

28. The method of claim 24, wherein the compound is represented by the following structural formula:

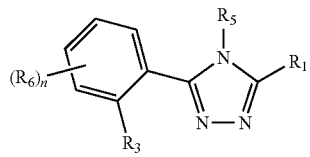

or a tautomer or pharmaceutically acceptable salt thereof; wherein:

$R_6$, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, $-NR_{10}R_{11}$, $-OR_7$, $-C(O)R_7$, $-C(O)OR_7$, $-C(S)R_7$, $-C(O)SR_7$, $-C(S)SR_7$, $-C(S)OR_7$, $-C(S)NR_{10}R_{11}$, $-C(NR_8)OR_7$, $-C(NR_8)R_7$, $-C(NR_8)NR_{10}R_{11}$, $-C(NR_8)SR_7$, $-OC(O)R_7$, $-OC(O)OR_7$, $-OC(S)OR_7$, $-OC(NR_8)OR_7$, $-SC(O)R_7$, $-SC(O)OR_7$, $-SC(NR_8)OR_7$, $-OC(S)R_7$, $-SC(S)R_7$, $-SC(S)OR_7$, $-OC(O)NR_{10}R_{11}$, $-OC(S)NR_{10}R_{11}$, $-OC(NR_8)NR_{10}R_{11}$, $-SC(O)NR_{10}R_{11}$, $-SC(NR_8)NR_{10}R_{11}$, $-SC(S)NR_{10}R_{11}$, $-OC(NR_8)R_7$, $-SC(NR_8)R_7$, $-C(O)NR_{10}R_{11}$, $-NR_8C(O)R_7$, $-NR_7C(S)R_7$, $-NR_7C(S)OR_7$, $-NR_7C(NR_8)R_7$, $-NR_7C(O)OR_7$, $-NR_7C(NR_8)OR_7$, $-NR_7C(O)NR_{10}R_{11}$, $-NR_7C(S)NR_{10}R_{11}$, $-NR_7C(NR_8)NR_{10}R_{11}$, $-SR_7$, $-S(O)_pR_7$, $-OS(O)_pR_7$, $-OS(O)_pOR_7$, $-OS(O)_pNR_{10}R_{11}$, $-S(O)_pOR_7$, $-NR_8S(O)_pR_7$, $-NR_7S(O)_pNR_{10}R_{11}$, $-NR_7S(O)_pOR_7$, $-S(O)_pNR_{10}R_{11}$, $-SS(O)_pR_7$, $-SS(O)_pOR_7$, $-SS(O)_pNR_{10}R_{11}$, $-OP(O)(OR_7)_2$, or $-SP(O)(OR_7)_2$; and n is zero of an integer from 1 to 4.

29. A method of blocking, occluding, or otherwise disrupting blood flow in a disease associated with the neovasculature of a subject in need of such treatment, comprising administering to the subject an effective amount of a compound represented by the following structural formula:

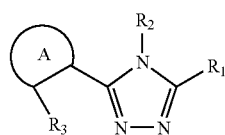

or a tautomer or pharmaceutically acceptable salt thereof;

wherein $R_2$ is a substituted phenyl, wherein the phenyl group is substituted with:
i) one substituent selected from nitro, cyano, a haloalkoxy, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkalkyl, hydroxylalkyl, alkoxyalkyl, guanadino, $-O13$ $R_{20}$, $-C(O)R_7$, $-C(O)OR_{20}$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, $-S(O)_pOR_7$, $-OP(O)(OR_7)_2$, or $-SP(O)(OR_7)_2$; or
ii) two to five substituents selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, $-F$, $-Br$, $-I$, cyano, nitro, guanadino, a haloalkyl, a heteroalkyl, $-NR_{10}R_{11}$, $-OR_7$, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, $-S(O)_pNR_{10}R_{11}$, $-OP(O)(OR_7)_2$, or $-SP(O)(OR_7)_2$, $-S(O)_pOR_7$; wherein the disease is selected from infectious diseases; autoimmune disorders; benign tumors; artheroscleric plaques; ocular angiogenic diseases; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; HHT; transplant arteriopathy; restinosis; obesity; myocardial angiogenesis; coronary collaterals; cerebral collaterals; arteriovenous malformations; ischemic limb angiogenesis; primary pulmonary hypertension; pulmonary edema; asthma; nasal polyps; inflammatory bowel disease; periodontal disease; ascites; peritoneal. adhesions; Osler-Webber Syndrome; plaque neovascularization; telangiectasia; hemophiliac joints; synovitis; osteomyelitis; osteophyte formation: angiofibroma; fibromuscular dysplasia; wound granulation; Crohn's disease; and atherosclerosis.

30. The method of claim 28, wherein the compound is represented by the following structural formula:

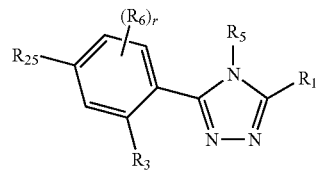

or a tautomer or pharmaceutically acceptable salt thereof, wherein:

$R_{25}$ is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$;

k is 1, 2, 3, or 4; and r is zero or an integer from 1 to 3.

31. The method of claim 30, wherein R$_1$, R$_3$ and R$_{25}$ are each independently —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$R$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$.

32. The compound of claim 25, wherein R$_1$ and R$_3$ are each, independently, —OH, —SH, or —NHR$_7$.

33. The method of claim 32, wherein the compound is represented by the following structural formula:

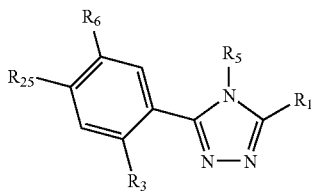

or a tautomer or pharmaceutically acceptable salt thereof;
wherein R$_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$.

34. The method of claim 33, wherein:
R$_1$ is —SH or —OH;
R$_3$ and R$_{25}$ are —OH;
R$_6$ is a lower alkyl, C3-C6 cycloalkyl, lower alkoxy, a lower alkyl sulfanyl, or —NR$_{10}$R$_{11}$; and
R$_9$, for each occurrence, is independently selected from the group consisting of —OH, —SH, halo, a lower haloalkyl, cyano, a lower alkyl, a lower alkoxy, and a lower alkyl sulfanyl.

35. The method of claim 31, wherein the compound is represented by the following structural formula:

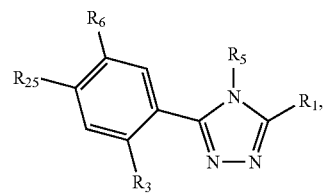

or a tautomer or pharmaceutically acceptable salt thereof;
wherein R$_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl, and R$_1$ and R$_3$ are each, independently, —OH, —SH, or —NHR$_7$.

36. The method of claim 35, wherein:
R$_1$ is —SH or —OH;
R$_3$ and R$_{25}$ are —OH;
R$_6$ is a lower alkyl, C3-C6 cycloalkyl, lower alkoxy, a lower alkyl sulfanyl, or —NR$_{10}$R$_{11}$.

37. The method of claim 24, wherein the compound is selected form the group consisting of:
3-(2-Hydroxyphenyl)-4-(naphthalen-1-yl)-5-mercapto-triazole;
3-(2,4-Dihydroxyphenyl)-4-[4-(2-methoxyethoxy)-naphthalen-1-yl]-5-mercapto-triazole;
3-(2,4-Dihydroxyphenyl)-4-(2-methyl-4-bromophenyl)-5-mercapto-triazole;
3-(3,4-Dihydroxyphenyl)-4-(6-methoxy-naphthalen-1-yl)-5-mercapto-triazole;
3-(3,4-Dihydroxyphenyl)-4-(6-ethoxy-naphthalen-1-yl)-5-mercapto-triazole;
3-(3,4-Dihydroxyphenyl)-4-(6-propoxy-naphthalen-1-yl)-5-mercapto-triazole;
3-(2,4-Dihydroxy-5-ethyl-phenyl)-4-(5-methoxy-naphthalen-1-yl)-5-mercapto-triazole;
3-(3,4-Dihydroxyphenyl)-4-(6-isopropoxy-naphthalen-1-yl)-5-mercapto-triazole;
3-(2,4-Dihydroxyphenyl)-4-(2,6-diethylphenyl)-5-mercapto-triazole;
3-(2,4-Dihydroxyphenyl)-4-(2-methyl-6-ethylphenyl)-5-mercapto-triazole;
3-(2,4-Dihydroxyphenyl)-4-(2,6-diisopropylphenyl)-5-mercapto-triazole;

3-(2,4-Dihydroxyphenyl)-4-(1-ethyl-indol-4-yl)-5-mercapto-triazole;
3-(2,4-Dihydroxyphenyl)-4-(2,3-dihydro-benzo [1,4]dioxin-5-yl)-5-mercapto-triazole;
3-(2,4-Dihydroxyphenyl)-4-(3-methylphenyl)-5-mercapto-triazole;
3-(2,4-Dihydroxyphenyl)-4-(4-methylphenyl)-5-mercapto-triazole;
3-(2,4-Dihydroxyphenyl)-4-(2-Chlorophenyl)-5-mercapto-triazole;
3-(2,4-Dihydroxyphenyl)-4-(3-Chlorophenyl)-5-mercapto-triazole;
3-(2,4-Dihydroxyphenyl)-4-(4-Chlorophenyl)-5-mercapto-triazole;
3-(2,4-Dihydroxyphenyl)-4-(2-methoxyphenyl)-5-mercapto-triazole;
3-(2,4-Dihydroxyphenyl)-4-(3-methoxyphenyl)-5-mercapto-triazole;
3-(2,4-Dihydroxyphenyl)-4-(3-fluorophenyl)-5-mercapto-triazole;
3-(2,4-Dihydroxyphenyl)-4-(2-ethylphenyl)-5-mercapto-triazole;
3-(2-Hydroxy-4-fluorophenyl)-4-(naphthalen-1-yl)-5-mercapto-triazole;
3-(2-Hydroxy-4-aminophenyl)-4-(naphthalen-1-yl)-5-mercapto-triazole;
3-(2,4-Dihydroxyphenyl)-4-(2-methyl-4-butyl-phenyl)-5-mercapto-triazole;
3-(2,4-Dihydroxyphenyl)-4-(2,4-dimethyl-phenyl)-5-mercapto-triazole;
3-(2,4-Dihydroxyphenyl)-4-(2,6-dimethyl-phenyl)-5-mercapto-triazole;
3-(2,4-Dihydroxyphenyl)-4-(2,6-dimethyl-phenyl)-5-mercapto-triazole;
3-(2,4-Dihydroxyphenyl)-4-(4-fluorophenyl)-5-mercapto-triazole;
3-(2,4-Dihydroxyphenyl)-4-(2-methylsulfanylphenyl)-5-mercapto-triazole;
3-(2,4-Dihydroxyphenyl)-4-(naphthalene-2-yl)-5-mercapto-triazole;
3-(2,4-Dihydroxyphenyl)-4-(2,3-dimethylphenyl)-5-mercapto-triazole;
3-(2,4-Dihydroxyphenyl)-4-(2-methyl-4-fluorophenyl)-5-mercapto-triazole;
3-(2,4-Dihydroxyphenyl)-4-(acenaphthalen-5-yl)-5-mercapto-triazole;
3-(2-Hydroxy-4-methoxy-phenyl)-4-(naphthalen-1-yl)-5-mercapto-triazole;
3-(2,4-Dihydroxyphenyl)-4-(2,3-dichlorophenyl)-5-mercapto-triazole;
3-(2,4-Dihydroxyphenyl)-4-(5-methoxynaphthalen-1-yl)-5-mercapto-triazole;
3-(2,4-Dihydroxyphenyl)-4-(pyren-1-yl)-5-mercapto-triazole;
3-(2,4-Dihydroxyphenyl)-4-(quinolin-5-yl)-5-mercapto-triazole;
3-(2,4-Dihydroxyphenyl)-4-(1,2,3,4-tetrahydronaphthalen-5-yl)-5-mercapto-triazole;
3-(2,4-Dihydroxyphenyl)-4-(anthracen-1-yl)-5-mercapto-triazole;
3-(2,4-Dihydroxyphenyl)-4-(biphenyl-2-yl)-5-mercapto-triazole;
3-(2,4-Dihydroxy-6-methyl-phenyl)-4-(naphthalene-1-yl)-5-mercapto-triazole;
3-(2,4-Dihydroxyphenyl)-4-(4-pentyloxyphenyl)-5-mercapto-triazole;
3-(2,4-Dihydroxyphenyl)-4-(4-octyloxyphenyl)-5-mercapto-triazole;
3-(2,4-Dihydroxyphenyl)-4-(4-Chloronaphthalen-1-yl)-5-mercapto-triazole;
3-(2,4-Dihydroxy-5-ethyl-phenyl)-4-(naphthalen-1-yl)-5-mercapto-triazole;
3-(2,4-Dihydroxy-5-ethyl-phenyl)-4-(7-carboxymethoxy-naphthalen-1-yl)-5-mercapto-triazole;
3-(2,4-Dihydroxyphenyl)-4-(2-methyl-quinolin-4-yl)-5-mercapto-triazole;
3-(3-Hydroxypyridin-4-yl)-4-(naphthalen-1-yl)-5-mercapto-triazole;
3-(2-Hydroxy-4-acetylamino-phenyl)-4-(naphthalen-1-yl)-5-mercapto-triazole;
3-(2,4-Dihydroxy-phenyl)-4-(1,2,3,4-tetrahydronaphthalen-1-yl)-5-mercapto-triazole;
3-(2,4-Dihydroxy-phenyl)-4-(2,3-dihydro-benzo[1,4]dioxin-5-yl)-5-mercapto-triazole;
3-(2,4-Dihydroxy-phenyl)-4-(3,5-dimethoxyphenyl)-5-mercapto-triazole;
3-(2,4-Dihydroxy-phenyl)-4-(2,3-dimethyl-1H-indol-4-yl)-5-mercapto-triazole;
3-(2,4-Dihydroxy-3-propyl-phenyl)-4-(naphthalen-1-yl)-5-mercapto-triazole;
3-(4,6-Dihydroxy-1-ethyl-pyridin-3-yl)-4-(naphthalen-1-yl)-5-mercapto-triazole;
3-(4,6-Dihydroxy-1-methyl-pyridin-3-yl)-4-(naphthalen-1-yl)-5-mercapto-triazole;
3-(2,4-Dihydroxy-phenyl)-4-(3,5-di-tert-butylphenyl)-5-mercapto-triazole;
3-(2,6-Dihydroxy5-fluoro-pyridin-3-yl) 4-(naphthalen-1-yl)-5-mercapto-triazole;
3-(2,4-Dihydroxy-5-methyl-phenyl)-4-(naphthalene-1-yl)-5-mercapto-triazole;
3-[2,4-Dihydroxy-phenyl]-4-(3-benzoylphenyl)-5-mercapto-triazole;
3-(2,4-Dihydroxy-phenyl)-4-(4-carboxy-naphthalen-1-yl)-5-mercapto-triazole;
3-(2,4-Dihydroxy-phenyl)-4-[4-(N,N-dimethylcarbamoyl)-naphthalen-1-yl]-5-mercapto-triazole;
3-(2,4-Dihydroxy-phenyl)-4-(4-propoxy-naphthalen-1-yl)-5-mercapto-triazole;
3-(2,4-Dihydroxy-phenyl)-4-(4-isopropoxy-naphthalen-1-yl)-5-mercapto-triazole;
3-(2,4-Dihydroxy-phenyl)-4-(5-isopropoxy-naphthalen-1-yl)-5-mercapto-triazole;
3-(2,4-Dihydroxy-phenyl)-4-(isoquinolin-5-yl)-5-mercapto-triazole;
3-(2,4-Dihydroxy-phenyl)-4-(5-propoxy-naphthalen-1-yl)-5-mercapto-triazole;
3-(2-Hydroxy-4-methanesulfonamino-phenyl)-4-(naphthalen-1-yl)-5-mercapto-triazole;
3-(2,4-Dihydroxy-3,6-dimethyl-phenyl)-4-(naphthalen-1-yl)-5-mercapto-triazole;
3-(2,4-Dihydroxy-phenyl)-4-[7-(2-methoxyethoxy)-naphthalen-1-yl]-5-mercapto-triazole;
3-(2,4-Dihydroxy-5-hexyl-phenyl)-4-(naphthalen-1-yl)-5-mercapto-triazole;
3-(2,4-Dihydroxy-5-ethyl-phenyl)-4-(4-methoxy-naphthalen-1-yl)-5-mercapto-triazole;
3-(2,4-Dihydroxy-5-ethyl-phenyl)-4-(6-methoxy-naphthalin-1-yl)-5-mercapto-triazole;
3-(2,4-Dihydroxy-3-Chloro-5-ethyl-phenyl)-4-(naphtha-len-1-yl)-5-mercapto-triazole;
3-(2,4-Dihydroxy-5-ethyl-phenyl)-4-(2,3-dimethyl-4-methoxy-phenyl)-5-mercapto-triazole;

3-(2,4-Dihydroxy-phenyl)-4-(7-isopropoxy-naphthalen-1-yl)-5-mercapto-triazole;
3-(2,4-Dihydroxy-phenyl)-4-(7-ethoxy-naphthalen-1-yl)-5-mercapto-triazole;
3-(2,4-Dihydroxy-phenyl)-4-(7-propoxy-naphthalen-1-yl)-5-mercapto-triazole;
3-(2-Hydroxy-4-methoxymethyoxy-phenyl)-4-(naphthalen-1-yl)-5-mercapto-triazole;
3-[2-Hydroxy-4-(2-hydroxy-ethoxy)-phenyl]-4-(naphthalen-1-yl)-5-mercapto-triazole;
3-(2,4-Dihydroxyphenyl)-4-(7-methoxy-naphthalen-1-yl)-5-mercapto-triazole;
3-(2,4-Dihydroxyphenyl)-4-(5-methoxy-naphthalen-1-yl)-5-mercapto-triazole;
3-(2,4-Dihydroxyphenyl)-4-(4-hydroxy-naphthalen-1-yl)-5-mercapto-triazole;
3-(2,4-Dihydroxyphenyl)-4-(1-isopropyl-indol-4-yl)-5-mercapto-triazole;
3-(2,4-Dihydroxy-5-tert-butyl-phenyl)-4-(naphthalen-1-yl)-5-mercapto-triazole;
3-(2,4-Dihydroxy-5-propyl-phenyl)-4-(naphthalen-1-yl)-5-mercapto-triazole;
3-(2,4-Dihydroxy-3-methyl-5-ethyl-phenyl)-4-(naphthalen-1-yl)-5-mercapto-triazole;
3-(2,4-Dihydroxy-5-isobutyl-phenyl)-4-(naphthalen-1-yl)-5-mercapto-triazole;
3-(2,4-Dihydroxy-phenyl)-4-(2,3-dimethoxy-phenyl)-5-mercapto-triazole;
3-(2,4-Dihydroxy-phenyl)-4-(2-methoxy-3-Chloro-phenyl)-5-mercapto-triazole;
3-(2,4-Dihydroxy-phenyl)-4-(indol-4-yl)-5-mercapto-triazole;
3-(2,4-Dihydroxy-phenyl)-4-[1-(2-methoxyethoxy)-indol-4-yl]-5-mercapto-triazole;
3-(2,4-Dihydroxy-phenyl)-4-(naphthalen-1-yl)-5-hydroxy-triazole;
3-(1-Oxo-3-hydroxy-pyridin-4-yl)-4-(naphthalen-1-yl)-5-mercapto-triazole;
3-(2,5-Dihydroxy-4-carboxy)-4-(naphthalen-1-yl)-5-mercapto-triazole;
3-(2,4-Dihydroxy-5-ethyl-phenyl)-4-(1-isopropyl-indol-4-yl)-5-mercapto-triazole;
3-(2,4-Dihydroxy-5-ethyl-phenyl)-4-[1-(dimethyl-carbamoyl)-indol-4-yl]-5-mercapto-triazole;
3-(2,4-Dihydroxy-5-ethyl-phenyl)-4-(1-ethyl-benzoimidazol-4-yl)-5-mercapto-triazole;
3-(2,4-Dihydroxy-5-ethyl-phenyl)-4-(1,2,3-trimethyl-indol-5-yl)-5-mercapto-triazole;
3-(2,5-Dihydroxy-4-hydroxymethyl-phenyl)-4-(naphthalen-1-yl)-5-mercapto-triazole;
3-(2-Hydroxy-4-amino-phenyl)-4-(naphthalen-1-yl)-5-mercapto-triazole;
3-(2-Hydroxy-4-acetylamino-phenyl)-4-(naphthalen-1-yl)-5-mercapto-triazole;
3-(2,4-Dihydroxy-3-Chloro-phenyl)-4-(naphthalen-1-yl)-5-mercapto-triazole;
3-(2,4-Dihydroxy-5-ethyl-phenyl)-4-(3-methoxy-phenyl)-5-hydroxy-triazole;
3-(2,4-Dihydroxy-5-ethyl-phenyl)-4-(naphthalen-1-yl)-5-hydroxy-triazole;
3-(2,4-Dihydroxy-5-ethyl-phenyl)-4-(1-isopropyl-indol-3-yl)-5-hydroxy-triazole;
3-(2,4-Dihydroxy-5-ethyl-phenyl)-4-(1-isopropyl-indol-4-yl)-5-amino-triazole;
3-(2,4-Dihydroxy-5-ethyl-phenyl)-4-(3-methoxy-phenyl)-5-amino-triazole;
3-(2,4-Dihydroxy-5-ethyl-phenyl)-4-(naphthalen-1-yl)-5-amino-triazole;
3-(2-Hydroxy-5-ethyloxy-phenyl)-4-(naphthalen-1-yl)-5-hydroxy-triazole;
3-(2-Hydroxy-5-isopropyl-phenyl)-4-(naphthalen-1-yl)-5-hydroxy-triazole;
3-(2-Dihydroxy-phenyl)-4-(7-fluoro-naphthalen-1-yl)-5-hydroxy-triazole;
3-(2,4-Dihydroxy-phenyl)-4-(2,3-difluorophenyl)-5-hydroxy-triazole;
3-(2,4-Dihydroxy-phenyl)-4-[2-(1H-tetrazol-5-yl)-phenyl]-5-hydroxy-triazole;
3-(2,4-Dihydroxy-phenyl)-4-(benzothiazol-4-yl)-5-hydroxy-triazole;
3-(2,4-Dihydroxy-phenyl)-4-(9H-purin-6-yl)-5-hydroxy-triazole;
3-(2,4-Dihydroxy-phenyl)-4-{4-[2-(moropholin-1-yl)-ethoxy]-phenyl}-5-hydroxy-triazole;
3-(2,4-Dihydroxy-phenyl)-4-cyclopentyl-5-hydroxy-triazole;
3-(2,4-Dihydroxy-phenyl)-4-phenyl-5-(sulfamoylamino)-triazole;
3-(2,4-Dihydroxy-5-methoxy-phenyl)-4-(naphthalene-1-yl)-5-ureido-triazole;
3-(2,4-Dihydroxy-5-methoxy-phenyl)-4-(2,3-difluorophenyl)-5-ureido-triazole;
3-(2,4-Dihydroxy-5-ethyl-phenyl)-4-(1-isopropyl-indol-4-yl)-5-ureido-triazole;
3-(2,4-Dihydroxy-5-ethyl-phenyl)-4-(quinolin-5-yl)-5-ureido-triazole;
3-(2,4-Dihydroxy-5-methoxy-phenyl)-4-(naphthalene-1-yl)-5-carbamoyloxy-triazole;
3-(2,4-Dihydroxy-5-ethyl-phenyl)-4-(3-trifluoromethyl-phenyl)-5-carbamoyloxy-triazole;
3-(2,4-Dihydroxy-5-ethyl-phenyl)-4-(1-methyl-indol-4-yl)-5-carbamoyloxy-triazole;
3-(2,4-Dihydroxy-5-methoxy-phenyl)-4-(8-methoxy-quinolin-5-yl)-5-carbamoyloxy-triazole;
3-(2,4-Dihydroxy-5-isopropyl-phenyl)-4-(3-methyl-quinolin-5-yl)-5-carboxyamino-triazole;
3-(2,4-Dihydroxy-phenyl)-4-(1-methyl-2-Chloro-indol-4-yl)-5-carbamoyloxy-triazole;
3-(2,4-Dihydroxy-5-methoxy-phenyl)-4-[3,5-di-(trifluoromethyl)-phenyl]-5-carbamoyloxy-triazole;
3-(2,4-Dihydroxy-5-methoxy-phenyl)-4-(3-trifluoromethyl-phenyl)-5-(sulfamoylamino)-triazole;
3-(2,4-Dihydroxy-5-methoxy-phenyl)-4-(naphthalene-1-yl)-5-(sulfamoylamino)-triazole;
3-(2,4-Dihydroxy-5-methoxy-phenyl)-4-(1-isopropyl-benzoimidazol-4-yl)-5-(sulfamoylamino)-triazole;
3-(2,4-Dihydroxy-5-methoxy-phenyl)-4-(3-isopropylphenyl)-5-(thiocarboxyamino)-triazole;
3-(2,4-Dihydroxy-5-methoxy-phenyl)-4-(3-isopropyloxy-phenyl)-5-(sulfamoyloxy)-triazole;
3-(2,4-Dihydroxy-5-methoxy-phenyl)-4-(naphthalene-1-yl)-5-(sulfamoyloxy)-triazole;
3-(2,4-Dihydroxy-5-methoxy-phenyl)-4-(naphthalen-1-yl)-5-mercapto-triazole;
3-(2,4-Dihydroxy-5-ethyl-phenyl)-4-(5-hydroxy-naphthalen-1-yl)-5-mercapto-triazole;
3-(2,4-Dihydroxy-phenyl)-4-(naphthalen-1-ylmethyl)-5-mercapto-triazole;
3-(2-Hydroxy-4-methoxyphenyl)-4-(naphthalen-1-yl)-5-mercapto-triazole;
3-(2,4-Dihydroxy-phenyl)-4-(biphenyl-3-yl)-5-mercapto-triazole;

3-(2,4-Dihydroxy-phenyl)-4-(2-methyl-5-hydroxymethyl-phenyl)-5-mercapto-triazole;

3-(2,4-Dihydroxy-phenyl)-4-(1-dimethylcarbamoyl-indol-4-yl)-5-mercapto-triazole;

3-(2,4,5-Trihydroxy-phenyl)-4-(naphthalene-1-yl)-5-mercapto-triazole;

3-(2,4-Dihydroxy-5-ethyl-phenyl)-4-(2,3-dimethyl-indol-5-yl)-5-mercapto-triazole;

3-(2,4-Dihydroxy-5-ethyl-phenyl)-4-(3-t-butyl-4-methoxy-phenyl)-5-mercapto-triazole;

3-(2,4-Dihydroxy-5-ethyl-phenyl)-4-(1-ethyl-1H-benzoimidazol-4-yl)-5-mercapto-triazole, HCl salt;

3-(2,4-Dihydroxy-5-ethyl-phenyl)-4-(1-isopropyl-7-methoxy-indol-4-yl)-5-mercapto-triazole; and 3-(2,4-Dihydroxy-5-cyclopropyl-phenyl)-4-(naphthalene-1-yl)-5-mercapto-triazole or a tautomer or pharmaceutically acceptable salt thereof.

38. A method of blocking, occluding, or otherwise disrupting blood flow in a disease associated with neovasculature, comprising contacting the neovasculature with an effective amount of a compound represented by the following structural formula:

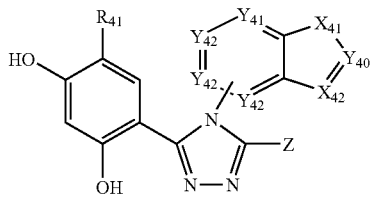

or a tautomer or pharmaceutically acceptable salt thereof, wherein:

$X_{41}$ is O, S, or $NR_{42}$;

$X_{42}$ is $CR_{44}$ or N;

$Y_{40}$ is N or $CR_{43}$;

$Y_{41}$ is N or $CR_{45}$;

$Y_{42}$, for each occurrence, is independently N, C or $CR_{46}$;

Z is OH, SH, or $NHR_7$;

$R_{41}$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, halo, cyano, nitro, guanadino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$;

$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, hydroxyalkyl, alkoxyalkyl, halo, cyano, nitro, guanadino, a haloalkyl, a heteroalkyl, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, —$S(O)_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;

$R_{45}$ is —H, —OH, —SH, —$NR_7H$, —$OR_{26}$, —$SR_{26}$, —$NHR_{26}$, —$O(CH_2)_mOH$, —$O(CH_2)_mSH$, —$O(CH_2)_mNR_7H$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$;

$R_{46}$, for each occurrence, is independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteralkyl, halo, cyano, nitro, guanadino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$, for each occurrence is, is independently, a lower alkyl;

p, for each occurrence, is, independently, 1 or 2; and m, for each occurrence, is independently, 1, 2, 3, or 4, wherein the neovasculature is in a subject in need of treatment to block, occlude or otherwise disrupt blood flow in the neovasculature; wherein the disease is selected rom infectious diseases; autoimmune disorders; benign tumors; artheroscleric plaques; Ocular angiogenic diseases; rheumatoid arthritis; psoriasis; warts; allergic dermatitis; blistering disease; Karposi sarcoma; delayed wound healing; endometriosis; Uterine bleeding; ovarian cysts; ovarian hyperstimulation; vasculogenesis; granulations; hypertrophic scars. (keloids); nonunion fractures; scleroderma: trachoma; vascular adhesions; vascular malformations; DiGeorge syndrome; HHT; transplant arteriopathy; restinosis; obesity; myocardial angiogenesis; coronary collaterals; cerebral collaterals; arteriovenous. malformations; ischemic limb angiogenesis; primary pulmonary hypertension; pulmonary edema; asthma; nasal polyps; inflammatory bowel disease; periodontal disease; ascites; peritoneal adhesions; Osler-Webber Syndrome; plaque neovascularization; telangiectasia; hemophiliac joints; synovitis; osteomyelitis; osteophyte formation; angiofibroma; fibromuscular dysplasia; wound granulation; Crohn's disease; and atherosclerosis.

39. The method of claim 38, wherein $X_{41}$ is $NR_{42}$ and $X_{42}$ is $CR_{44}$.

40. The method of claim 38, wherein $X_{41}$ is $NR_{42}$, and $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

41. The method of claim 38, wherein $R_{43}$ and $R_{44}$ are, independently, selected from the group consisting of —H, methyl, ethyl, propyl, isopropyl, cyclopropyl, methoxy, ethoxy, propoxy, and cyclopropoxy; and Z is —OH or —SH.

42. The method of claim 38, wherein the compound is selected from the group consisting of:

3-(2,4-dihydroxy-5-ethyl-phenyl)-4-(2-methyl-7-methoxy-benzofuran-4-yl)-5-mercapto-[1,2,4]triazole, 3-(2,4-dihydroxy-5-ethyl-phenyl)-4-(benzofuran-5-yl)-5-mercapto-[1,2,4]triazole, and 3-(2,4-dihydroxy-5-ethyl-phenyl)-4-(2-methyl-1,3-benzoxaz-5-yl)-5-mercapto-[1,2,4]triazole; or a tautomer or pharmaceutically acceptable salt thereof.

43. The method of claim 38, wherein the compound is represented by the following structural formula:

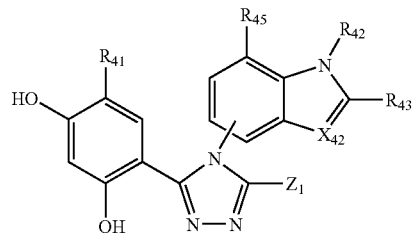

or a tautomer or pharmaceutically acceptable salt thereof, wherein $Z_1$ is —OH or —SH.

44. The method of claim 43, wherein $X_{42}$ is $CR_{44}$, and $R_{43}$ and $R_{44}$ are, independently, selected from the group consisting of —H, methyl, ethyl, propyl, isopropyl, cyclopropyl, methoxy, ethoxy, propoxy, and cyclopropoxy.

45. The method of claim 43, wherein:

$X_{45}$ is $CR_{54}$ or N;

$R_{56}$ is selected from the group consisting of —H, methyl, ethyl, isopropyl, and cyclopropyl;

$R_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;

$R_{53}$ and $R_{54}$ are each, independently, —H, methyl, ethyl, or isopropyl; or $R_{53}$ and $R_{54}$ taken together with the carbon atoms to which they are attached form a phenyl, cyclohexenyl, or cyclooctenyl ring; and $R_{55}$ is selected from the group consisting of —H, —OH, —OCH$_3$, and —OCH$_2$CH$_3$.

46. The method of claim 38, wherein the compound is selected from the group consisting of:

3-(2,4-dihydroxy-5-ethyl-phenyl)-4-(1,3-dimethyl-indol-5-yl)-5-hydroxy-[1,2,4]triazole, 3-(2,4-dihydroxy-5-isopropyl-phenyl)-4-(1,3-dimethyl-indol-5-yl)-5-hydroxy-[1,2,4]triazole, 3-(2,4-dihydroxy-5-isopropyl-phenyl)-4-(1-methyl-indol-5-yl)-5-hydroxy-[1,2,4]triazole, 3-(2,4-dihydroxy-5-isopropyl-phenyl)-4-(1-isopropyl-indol-4-yl)-5-hydroxy-[1,2,4]triazole;

3-(2,4-dihydroxy-5-isopropyl-phenyl)-4-(1-methyl-indazol-5-yl)-5-mercapto-[1,2,4]triazole;

3-(2,4-dihydroxy-5-isopropyl-phenyl)-4-(1-methyl-indazol-6-yl)-5-mercapto-[1,2,4]triazole;

3-(2,4-dihydroxyphenyl)-4-(1-ethyl-indol-4-yl)-5-mercapto-[1,2,4]triazole, 3-(2,4-dihydroxyphenyl)-4-(1-isopropyl-indol-4-yl)-5-mercapto-[1,2,4]triazole, 3-(2,4-dihydroxyphenyl)-4-(indol-4-yl)-5-mercapto-[1,2,4]triazole, 3-(2,4-dihydroxyphenyl)-4-(1-methoxyethyl-indol-4-yl)-5-mercapto-[1,2,4]triazole, 3(2,4-dihydroxy-5-ethyl-phenyl)-4-(1-isopropyl-indol-4-yl)-5-mercapto-[1,2,4]triazole, 3-(2,4-dihydroxyphenyl)-4-(1-dimethylcarbamoyl-indol-4-yl)-5-mercapto-[1,2,4]triazole, 3-(2,4-dihydroxy-5-ethyl-phenyl)-4-(1-propyl-indol-4-yl)-5-mercapto-[1,2,4]triazole, 3-(2,4-dihydroxy-5-ethyl-phenyl)-4-(1,2,3-trimethyl-indol-5-yl)-5-mercapto-[1,2,4]triazole, 3-(2,4-dihydroxy-5-ethyl-phenyl)-4-(2,3-dimethyl-indol-5-yl)-5-mercapto-[1,2,4]triazole, 3-(2,4-dihydroxy-5-ethyl-phenyl)-4-(1-acetyl-2,3-dimethyl-indol-5-yl)-5-mercapto-[1,2,4]triazole, 3-(2,4-dihydroxy-5-ethyl-phenyl)-4-(1-isopropyl-7-methoxy-indol-4-yl)-5-mercapto-[1,2,4]triazole, 3-(2,4-dihydroxy-5-ethyl-phenyl)-4-(1-propyl-2,3-dimethyl-indol-5-yl)-5-mercapto-[1,2,4]triazole,
3-(2,4-dihydroxy-5-ethyl-phenyl)-4-(N-methyl-tetrahydrocarbozol-7-yl)-5-mercapto-[1,2,4]triazole,
3-(2,4-dihydroxy-5-ethyl-phenyl)-4-(N-methyl-cyclononan[a]indol-5-yl)-5-mercapto-[1,2,4]triazole,
3-(2,4-dihydroxy-5-ethyl-phenyl)-4-(1-n-butyl-indol-4-yl)-5-mercapto-[1,2,4]triazole,
3-(2,4-dihydroxy-5-ethyl-phenyl)-4-(1-n-pentyl-indol-4-yl)-5-mercapto-[1,2,4]triazole,
3-(2,4-dihydroxy-5-ethyl-phenyl)-4-(1-n-hexyl-indol-4-yl)-5-mercapto-[1,2,4]triazole,
3-(2,4-dihydroxy-5-cyclopropyl-phenyl)-4-(1-(1-methylcyclopropyl)-indol-4-yl)-5-mercapto-[1,2,4]triazole,
3-(2,4-dihydroxy-5-cyclopropyl-phenyl)-4-(1-isopropyl-7-methoxy-indol-4-yl)-5-mercapto-[1,2,4]triazole,
3-(2,4-dihydroxy-5-cyclopropyl-phenyl)-4-(1,2,3-trimethyl-indol-5-yl)-5-mercapto-[1,2,4]triazole,
3-(2,4-dihydroxy-5-ethyl-phenyl)-4-(1-isopropyl-7-methoxy-indol-4-yl)-5-mercapto-[1,2,4]triazole disodium salt,
3-(2,4-dihydroxy-5-tert-butyl-phenyl)-4-(1-isopropyl-7-methoxy-indol-4-yl)-5-mercapto-[1,2,4]triazole,
3-(2,4-dihydroxy-5-cyclopropyl-phenyl)-4-(1-propyl-7-methoxy-indol-4-yl)-5-mercapto-[1,2,4]triazole,
3-(2,4-dihydroxy-5-ethyl-phenyl)-4-(1-methyl-3-ethyl-indol-5-yl)-5-mercapto-[1,2,4]triazole,
3-(2,4-dihydroxy-5-ethyl-phenyl)-4-(1,3-dimethyl-indol-5-yl)-5-mercapto-[1,2,4]triazole,
3-(2,4-dihydroxy-5-isopropyl-phenyl)-4-(1-isopropyl-7-methoxy-indol-4-yl)-5-mercapto-[1,2,4]triazole,
3-(2,4-dihydroxy-5-ethyl-phenyl)-4-(1-methyl-3-isopropyl-indol-5-yl)-5-mercapto-[1,2,4]triazole,
3-(2,4-dihydroxy-5-ethyl-phenyl)-4-(N-ethyl-carbozol-7-yl)-5-mercapto-[1,2,4]triazole,
3-(2,4-dihydroxy-5-ethyl-phenyl)-4-(1-isopropyl-7-hydroxy-indol-4-yl)-5-mercapto-[1,2,4]triazole,
3-(2,4-dihydroxy-5-ethyl-phenyl)-4-(1-isopropyl-7-ethoxy-indol-4-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-ethyl-phenyl)-44N-methyl-indol-5-yl)-5-mercapto-[1,2,4]triazole,
3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole,
3-(2,4-dihydroxy-5-isopropyl-phenyl)-4-(1-propyl-indol-5-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole HCL salt,
3-(2,4-dihydroxy-5-ethyl-phenyl)-4-(2-methyl-3-ethyl-benzimidazol-5-yl)-5-mercapto-[1,2,4]triazole,
3-(2,4-dihydroxy-5-ethyl-phenyl)-4-(1-ethyl-2-methyl-benzimidazol-5-yl)-5-mercapto-[1,2,4]triazole,
3-(2,4-dihydroxy-5-isopropyl-phenyl)-4-(1-methyl-2-trifluoromethyl-benzimidazol-5-yl)-5-mercapto-[1,2,4]triazole; and
3-(2,4-dihydroxy-5-isopropyl-phenyl)-4-(N-methyl-indol-5-yl)-5-mercapto-[1,2,4]triazole;
or tautomers or pharmaceutically acceptable salts thereof.

* * * * *